United States Patent
Ochiai et al.

(10) Patent No.: US 10,626,430 B2
(45) Date of Patent: Apr. 21, 2020

(54) METHOD FOR PREPARING MOGROSIDE HAVING NO β-1,6-GLUCOSIDE BOND

(71) Applicant: SUNTORY HOLDINGS LIMITED, Osaka (JP)

(72) Inventors: Misa Ochiai, Kyoto (JP); Eiichiro Ono, Kyoto (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 47 days.

(21) Appl. No.: 15/544,316

(22) PCT Filed: Jan. 19, 2016

(86) PCT No.: PCT/JP2016/051416
§ 371 (c)(1),
(2) Date: Jul. 18, 2017

(87) PCT Pub. No.: WO2016/117549
PCT Pub. Date: Jul. 28, 2016

(65) Prior Publication Data
US 2018/0010160 A1    Jan. 11, 2018

(30) Foreign Application Priority Data
Jan. 20, 2015 (JP) .................... 2015-008508

(51) Int. Cl.
| C12P 19/44 | (2006.01) |
| C12N 9/42 | (2006.01) |
| C12N 15/09 | (2006.01) |
| C12N 9/24 | (2006.01) |

(52) U.S. Cl.
CPC ............ *C12P 19/44* (2013.01); *C12N 9/2445* (2013.01); *C12N 15/09* (2013.01); *C07K 2319/02* (2013.01); *C12N 9/24* (2013.01)

(58) Field of Classification Search
None
See application file for complete search history.

(56) References Cited

U.S. PATENT DOCUMENTS

| 4,084,010 A | 4/1978 | Takemoto |
| 7,413,888 B2 | 8/2008 | Fidantsef |
| 8,772,010 B2 | 7/2014 | Zhang |
| 2004/0253702 A1 | 12/2004 | Fidantsef et al. |
| 2007/0117186 A1 | 5/2007 | Sahara et al. |
| 2012/0232166 A1 | 9/2012 | Finley et al. |
| 2014/0235537 A1 | 8/2014 | Meehl |
| 2016/0002692 A1 | 1/2016 | McBride et al. |

FOREIGN PATENT DOCUMENTS

| JP | 2002-383868 A | 7/2005 |
| JP | 2005-212327 A | 2/2007 |
| JP | 2007-028912 A | 2/2007 |
| JP | 2007-167062 | 7/2007 |
| WO | 2004/099228 | 11/2004 |
| WO | 2011/046768 | 4/2011 |
| WO | 2012/068832 A1 | 5/2012 |
| WO | 2014/150127 | 9/2014 |
| WO | 2014/151805 A2 | 9/2014 |
| WO | 2013/076577 | 5/2015 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AEX89467. May 17, 2007 (Year: 2007).*
Accession P01149. Jul. 21, 1986 (Year: 1986).*
Zhou et al., "Insulin secretion stimulating effects of mogroside V and fruit extract of Luo Han Kuo (*Siraitia grosvenori* Swingle) fruit extract", Acta Pharmaceutica Sinica, vol. 44, No. 11, pp. 1252-1257 (2009).
Suzuki et al., "Triterpene Glycosides of *Siraitia grosvenori* Inhibit Rat Intestinal Maltase and Suppress the Rise in Blood Glucose Level after a Single Oral Administration of Maltose in Rats", J. Agric. Food Chem., vol. 53, No. 8, pp. 2941-2946 (2005).
Langston et al., "Substrate specificity of *Aspergillus oryzae* family 3 β-glucosidase", Biochimica et Biophysica Acta, vol. 1764, No. 5, pp. 972-978 (2006).
Database GenBank, "beta-glucosidase F [Aspergillus oryzae RIB40]", NCBI Reference Sequence: XP_001819055.1, (2 pages), Mar. 3, 2011.
Database GenBank, "beta glucosidase, putative [Aspergillus flavus NRRL3357]", NCBI Reference Sequence: XP_002382041.1, (2 pages), Jan. 19, 2010.
Database GenBank, "beta-glucosidase-related glycosidase [Aspergillus oryzae 3.042]", GenBank: EIT73097.1, (2 pages), Jun. 18, 2012.
Chiu et al., "Biotransformation of Mogrosides from *Siraitia grosvenorii* Swingle by *Saccharomyces cerevisiae*", J. Agric. Food Chem., vol. 61, pp. 7127-7134 (2013).
International Search Report issued in PCT/JP2016/051416, dated Apr. 26, 2016.
Extended European Search Report issued in EP Patent Application No. 16740156.1, dated Oct. 10, 2018.
Partial Supplementary European Search Report issued in EP Patent Application No. 16740156.1, dated Jun. 1, 2018.

* cited by examiner

*Primary Examiner* — Christian L Fronda
(74) *Attorney, Agent, or Firm* — Greenblum & Bernstein, P.L.C.

(57) ABSTRACT

The present invention provides a method for preparing a mogroside having no β-1,6-glucoside bond comprising the step of reacting glycosidase ASBGL2, AOBGL2, AOBGL1, ASBGL1, or a variant thereof with a mogroside having at least one β-1,6-glucoside bond, thereby cleaving said β-1, 6-glucoside bond.

21 Claims, 6 Drawing Sheets
Specification includes a Sequence Listing.

MF(ALPHA)1 signal peptide

5' ATGAGATTTC CTTCAATTTT TACTGCAGTT TTATTCGCAG CATCCTCCGC ATTAGCT 3'
   M  R  F  P  S  I  F  T  A  V  L  F  A  A  S  S  A  L  A

B

PHO5 signal peptide

5' ATGTTTAAAT CTGTTGTTTA TTCAATTTTA GCCGCTTCTT TGGCCAATGC A 3'
   M  F  K  S  V  V  Y  S  I  L  A  A  S  L  A  N  A

C

SUC2 signal peptide

5' ATGCTTTTGC AAGCTTTCCT TTTCCTTTTG GCTGGTTTTG CAGCCAAAAT ATCTGCA 3'
   M  L  L  Q  A  F  L  F  L  L  A  G  F  A  A  K  I  S  A

[Figure 2]
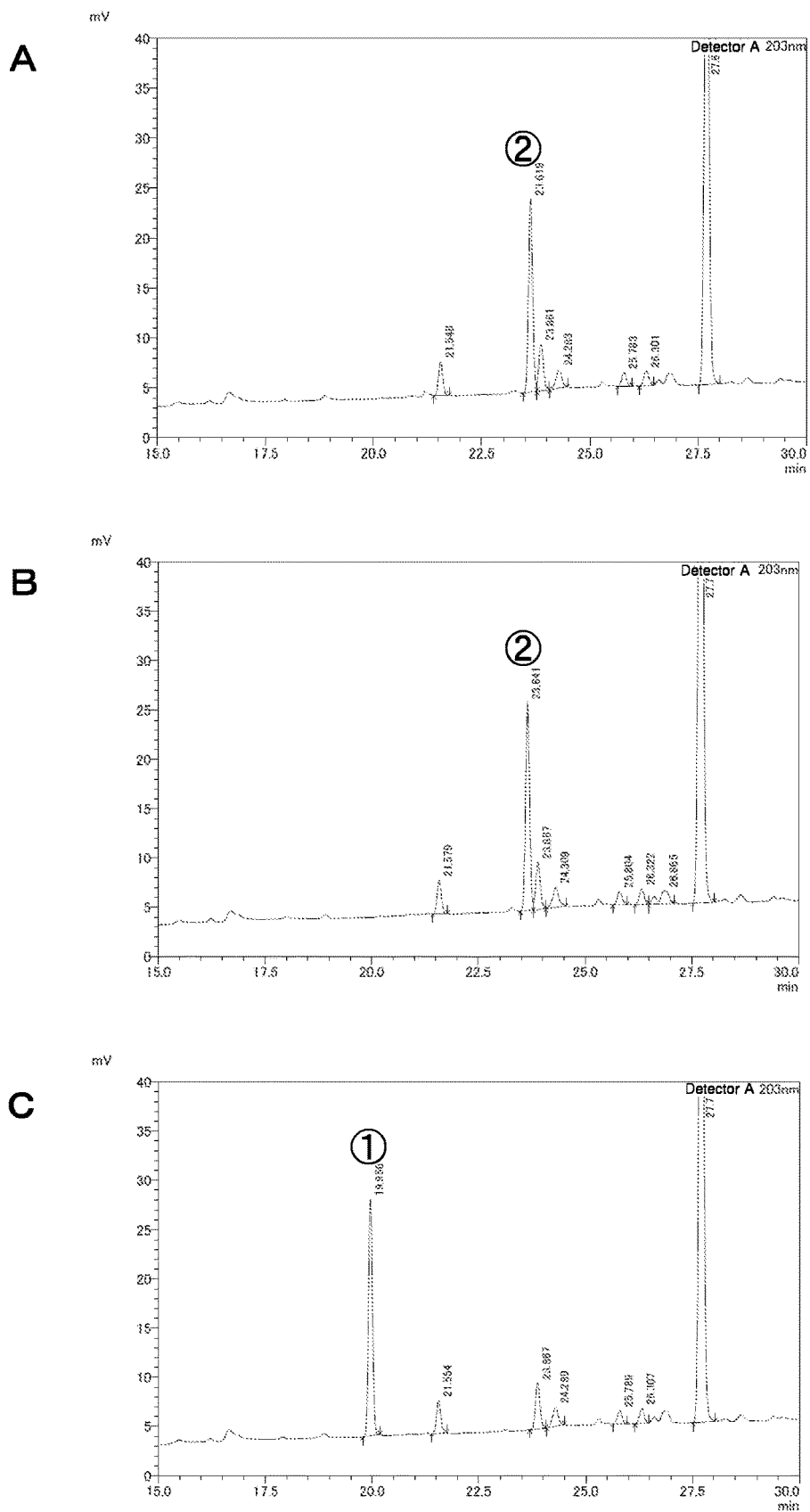

[Figure 3]
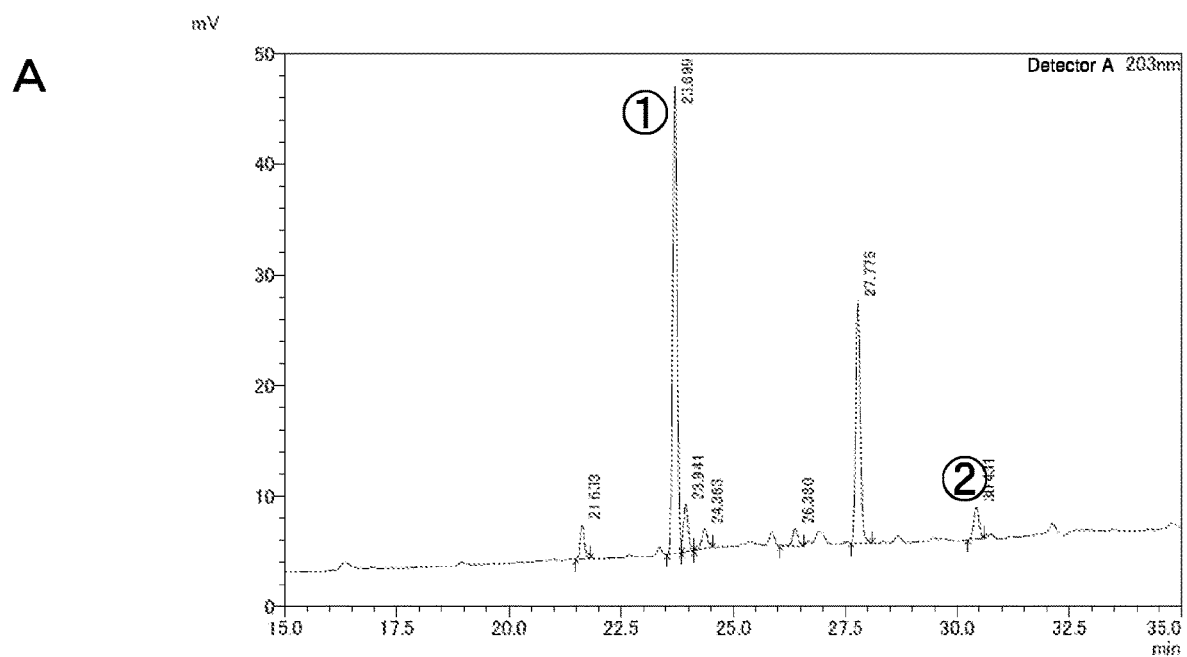
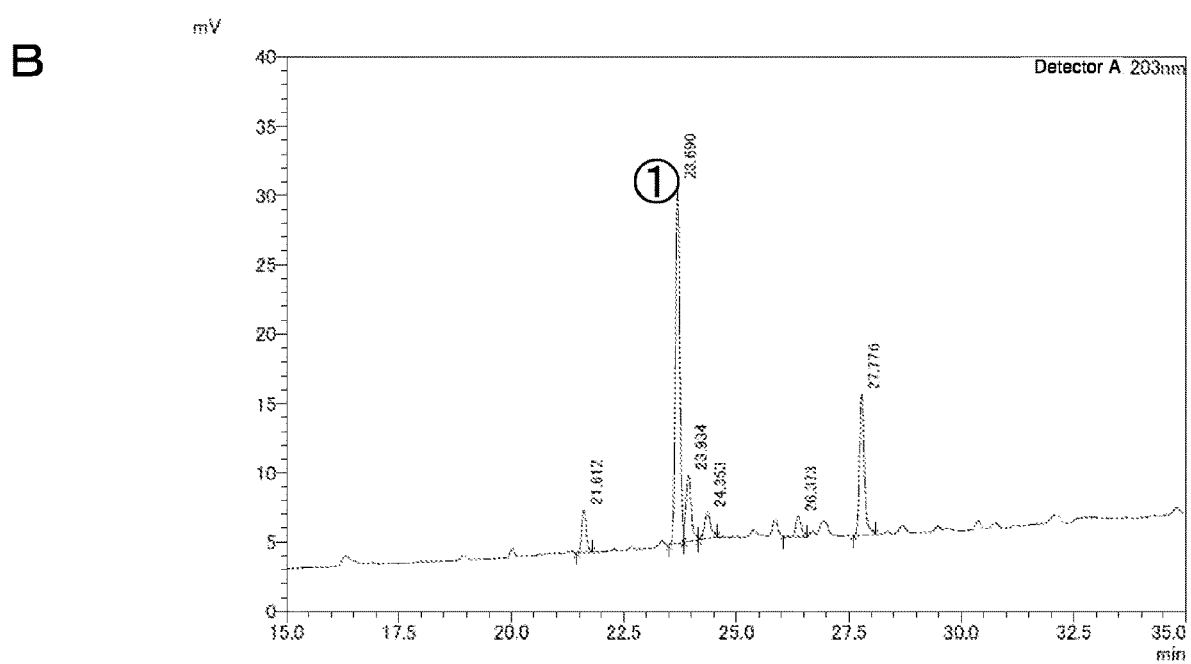

[Figure 4]
A
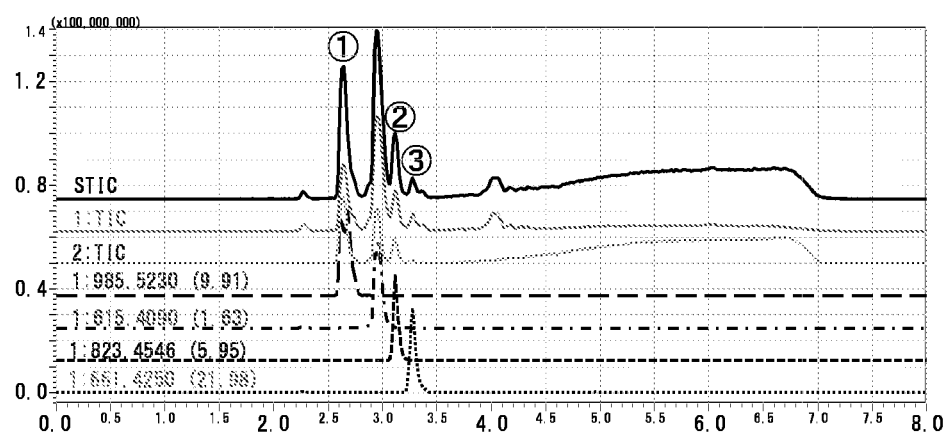
B
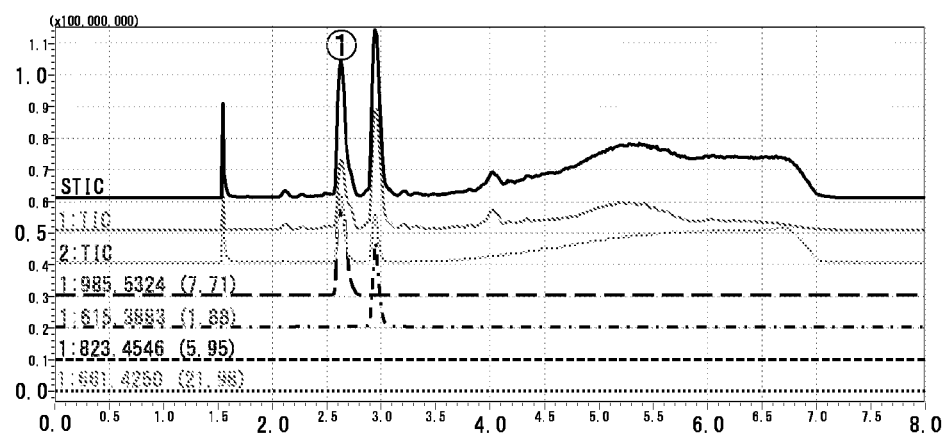

[Figure 5-1]

```
         1                                                                              80
AOBGL1p  ------------MK GWIEVAALA ASVV AKDDL AYS PF P SF WADGQG WAEV KRAVDI SQ T TEKVNL T T GW
ASBGL1p  ------------MK GWIEVAALV ASVV AKDDL AYS PF P SF WADGQG WAEV KRAVDI SQ T TEKVNL T T GW
AOBGL2p  MAAFPAYLALLSY VPGAL SHPE KTLT RASTE AYSP Y AP NGGWI S WASA EK HRV SN A KVNL SG GI
ASBGL2p  MAAFPAYLALLSY VPGAL SHPE ESLT RASTE AYSP Y AP NGGWI S WASA EK HRV SN A KVNL SG GI 81                                                                             160
AOBGL1p  QLER VG T GSVP LN  SL C QDSPL I RFS DYNSA P GVN AA TW K T A L GGQAM EEFSDK D Q G AAG L
ASBGL1p  QLER VG T GSVP LN  SL C QDSPL I RFS DYNSA P GVN AA TW K T A L GGQAM EEFSDK D Q G AAG L
AOBGL2p  YMGP AG T GSVP RFG N C HDSPL GV NSDH TA PAG IT GA FD D M E GVGL E ARGK  N L G SV  I
ASBGL2p  YMGP AG T GSVP RFG N C HDSPL GV NSDH TA PAG IT GA FD D M E GVGL E ARGK  N L G SV  I 161                                                                            240
AOBGL1p  GAH DGGRNW G SPD A TGVLFAE  KGI DA V ATAK Y MNE QEHF QQPEAAGYGF NVSDSL SSNV DK  M
ASBGL1p  GAH DGGRNW G SPD A TGVLFAE  KGI DA V ATAK Y MNE QEHF QQPEAAGYGF NVSDSL SNV DK  I
AOBGL2p  GRK  GGRNW G GAD  L QAFGGSL  KGM STG A ASL  L GN QE QHR MSS------VITQGY SSNI DR L
ASBGL2p  GRK  GGRNW G GAD  L QAFGGSL  KGM STG A ASL  L GN QE QHR MSS------VITQGY SSNI DR L 241                                                                            320
AOBGL1p  YLWP ADA RAG GA M CSY NQI NNS YGCE SETLNKL  AE G  QG VMSD T  HS GVGAA AGL D SM PGD-VTFDS
ASBGL1p  YLWP ADA RAG GA M CSY NQI NNS YGCE SETLNKL  AE G  QG VMSD T  HS GVGAA AGMD SM PG -VTFDS
AOBGL2p  YLWP AES RAG GS M AY NDV RS ACSQ SKLI GI  D  G  QG VVT W A  IGG SS A AGL D SM PGDGAIPLL
ASBGL2p  YLWP AES RAG GS M AY NDV RS ACSQ SKLI GI  D  G  QG VVT W A  IGG SS A AGL D SM PGDGAIPLL 321                                                                            400
AOBGL1p  G SF GAN TVG  NGTI QWRVD M AVR MAAYY VGR TK TPPN SSW RD Y FAHNHVSEGAYER NEF D GRD
ASBGL1p  G SF GAN TVG  NGTI QWRVD M AVR MAAYY VGR TK TPPN SSW RD Y FAHNHVSEGAYER NEF D GRD
AOBGL2p  G SY SWE SRS  NGSV VERLND VT  VA TWY KMGQ KD PL N SSN ED T PLYPGALFSPSGI QY N GN
ASBGL2p  G SY AWE SRS  NGSV VERLND VT  VA TWY KMGQ KD PL N SSN ED T PLYPGALFSPSGI QY N GN 401                                                                            480
AOBGL1p  ADLI R  GAQSTV  KNK-GA P S KEKLVALL EDA SN SW ANG DDR G DN T A AWGSG ANFP V  EQA
ASBGL1p  ADLI R  GAQSTV  KNK-GA P S KEKLVALL EDA SN SW ANG DDR G DN T A A GSG ANFP V  EQA
AOBGL2p  NVTA A  ARDAIT  KNNENV P KN-DTLKIF TDAG T SD  INS T KG NK V T G GSG SRL P I  QEA
ASBGL2p  NVTA A  ARDAIT  KN DNV P KN-ASLKIF TDAGAN D  INS T KG NK V T G GSG SRL P I  QEA
```

[Figure 5-2]

```
        481                                                                             560
AOBGL1p QNEVLQGRGNVEAVEDSWAEDKIAAAERQASVSLVEVNSDSGEGELSVDGNEGDR---NNITLEKNGDNVEKTEANNCNET
ASBGL1p QNEVLQGRGNVEAVEDSWAEDKIAAAERQASVSLVEVNSDSGEGELSVDGNEGDR---NNITLEKNGDNVEKTEANNCNET
AOBGL2p ANISSN----AEEHIEDTFPEG----VTAGPDDIAIVEINSDSGENEITVDGNPGDRTLAGLHAEHNGDNLVKAEAEKFSEV
ASBGL2p ANISSN----AEEHIEDTFPEG----VTAGLDDIAIVEINSDSGENEITVDGNPGDRTLAGLTAEHNGDNLVKAEAEKFSEV 561                                                                             640
AOBGL1p VEIIESVGPVEIDEEYEHPNVTGIELWAGEPGQESGNSEIAEVEEYGRVNEGAKSEFEWGKTRESEGSPLVKDENNGNEAPES
ASBGL1p VEIIESVGPVEINEEYEHPNVTGIELWAGEPGQESGNSEIAEVEEYGRVNEGAKSEFEWGKTRDSEGSPLVKDENNGNEAPES
AOBGL2p VEVVETVGPIEMEEEIEDLDSVKAVELVAHEPGQEAGWSLTEIIEFEDYSESGHLEYEIPHSESDEPESVGLIEQP-FEQIED
ASBGL2p VEVVETVGPIEMEEEIEDLDSVKAVELVAHEPGQEAGWSLTEIIEFEDYSESGHLEYEIPRSESDEPESVGLIEQP-FEQIED 641                                                                             720
AOBGL1p DFEQGVFEDYRHEDKFNETEIYEEGYGLESYETEELSDLHVQPLNASRYTPTSG---MTEAAKNFGEIGDESEYVYEEGLE
ASBGL1p DFEQGVFEDYRHEDKFNETEIYEEGYGLESYETEELSDLHVQPLNASQYTPTSG---MTEAAKNFGEIGDESEYVYEEGLE
AOBGL2p DYEEGLYEDYRHELEANIETPRYPEGHGLESYETENFTEPNLSIIKALDTAYPAARPPKGSTPTYPTAKPDESEVAWEKNFN
ASBGL2p DYEEGLYEDYRHELEANIETPRYPEGHGLESYETENFTEPNLSIIKPLDTAYPAARPPKGSTPTYPTTKPAESEVAWEKNFN 721                                                                             800
AOBGL1p REHEFIYEWINSTDLKESSDDSNEGWEESKYIPEGATDGSAQERLPESEGAEGGNEPGEYEDLERESEKNETGNVAEDEEP
ASBGL1p REHEFIYEWINSTDLKESSDDSNEGWEESEYIPEGATDGSAQERLPESEGAEGGNEPGEYEDLERESEKNETGNVAEDEEP
AOBGL2p REWRYLEYYLDNPEGAEANSSKTEYPYPEGYTTEP--------KEAPREGGAEGGNPAEWDVTESEQVKVETNEGSRDGRAEA
ASBGL2p REWRYLEYYLDNPEGAEANSSKTEYPYPEGYTTEP--------KEAPREGGAEGGNPAEWDVAESEQVKVETNEGSRDGRAEA 801                                                                             880
AOBGL1p QLYVVSEG---GPNEEKVVERKEERIHLAPSQE-AEWETTLERRDEANEDVSAQDWTVTPYPKTIYVGNSSRKLPEQASLP
ASBGL1p QLYVVSEG---GPNEEKVVERKEERIHLAPSQE-VEWETTLERRDEANEDVSAEDWAVTPYPKTIYVGNSSRKLPEQVSLP
AOBGL2p QLYVELPSSLEDTESRQERQEEKTKILAAGESEELELDVERKDESVEDVVVQDWKAPVNGEGVKIWVGESVADERVGCV
ASBGL2p QLYVELPSSLEDTESRQERQEEKTKILAAGESEELELDVERKDESAEDVVVQDWKAPVNGEGVKIWVGESVADERVGCV

881
AOBGL1p KAQ------
ASBGL1p KAQ------
AOBGL2p VGEGCSTL-
ASBGL2p VGEGCSTL-
```

METHOD FOR PREPARING MOGROSIDE HAVING NO β-1,6-GLUCOSIDE BOND

SEQUENCE LISTING

The instant application contains a Sequence Listing which has been filed electronically in ASCII format and is hereby incorporated by reference in its entirety. Said ASCII copy, created on Apr. 23, 2019, is named P52569_SL.txt and is 126,260 bytes in size.

TECHNICAL FIELD

The present invention relates to a method for preparing a mogroside.

BACKGROUND OF THE ART

*Siraitia grosvenorii* is a plant of the Cucurbitaceae family, native to Zhuang Autonomous Region of Guangxi, China. Fruits of *Siraitia grosvenorii* have a very sweet taste, and extracts from the fruits are used as natural sweeteners. Moreover, dried fruits of *Siraitia grosvenorii* are used as Chinese herbal medicines.

Fruits of *Siraitia grosvenorii* are known to contain mogrosides as sweet components. Mogrosides are glycosides wherein glucose is linked to the aglycone, mogrol. Mogrosides are classified into various types according to the position of linkage of glucose or the number of glucose units. Mogroside V, mogroside IV, siamenoside I, and 11-oxomogroside are contained in fruits of *Siraitia grosvenorii*. Other mogrosides are also known, such as mogroside I, mogroside IVA, mogroside III, mogroside $IIIA_1$, mogroside $IIIA_2$, mogroside IIIE, mogroside IIA, mogroside $IIA_1$, mogroside $IIA_2$, mogroside IIB, mogroside IIE, mogroside $IA_1$, and mogroside $IE_1$.

These mogrosides have been shown to have a variety of bioactivities. For example, mogroside V has been reported to have the function of regulating insulin secretion in vitro (Non Patent Literature 1: Yao Xue Xue Bao, 2009, 44, 1252-1257). Mogroside III has also been reported to show maltase inhibitory activity in the intestinal tract, and to suppress a rise in blood glucose level (Non Patent Literature 2: J. Agric. Food Chem. 2005, 53, 2941-2946).

While such mogrosides can be prepared by purification of extracts of fruits of *Siraitia grosvenorii*, several other methods are also known for the preparation of mogrosides. For example, a method for preparing various mogrosides by glycosylation of mogrol with a UDP-glucosyltransferase has been disclosed (Patent Literature 1: WO 2013/076577). Furthermore, a method for preparing various mogrol glycosides from *Siraitia grosvenorii* extracts with an *Aspergillus niger*-derived pectinase has been disclosed (Patent Literature 1: WO 2013/076577).

It has been disclosed that yeast (*Saccharomyces cerevisiae*) has an activity to convert mogroside V into mogroside IIIE, and the yeast gene responsible for this activity is EXG1 (GH family 5, β-1,3-glucanase) (Non Patent Literature 3: J. Agric. Food Chem, 2013, 61, 7127-7134).

Furthermore, koji mold is known as an organism that secretes various hydrolases, and its genomic information is known. Although about 40 genes exist that are considered to encode β-glucosidase-like proteins, there is little information regarding the substrate specificity of the protein encoded by each of the genes. It has been reported that the β-glucosidase of the glycoside hydrolase (GH) family 3 encoded by the AO090009000356 gene of koji mold hydrolyzes disaccharides with a β-glucoside bond (Non Patent Literature 4: Biosci. Biotech. Biochem. 1764 972-978 (2006)). Specifically, its specificity for hydrolysis is the highest for laminaribiose with a β-1,3 linkage, followed by β-gentiobiose with a β-1,6 linkage, cellobiose with a β-1,4 linkage, and sophorose with a β-1,2 linkage.

CITATION LIST

Patent Literature

Patent Literature 1: WO 2013/076577

Non Patent Literature

Non Patent Literature 1: Yao Xue Xue Bao, 2009, 44, 1252-1257
Non Patent Literature 2: J. Agric. Food Chem. 2005, 53, 2941-2946
Non Patent Literature 3: J. Agric. Food Chem, 2013, 61, 7127-7134
Non Patent Literature 4: Biosci. Biotech. Biochem. 1764 972-978 (2006)

SUMMARY OF INVENTION

Problem to Be Solved

Under the foregoing circumstances, there is a need for a novel method for producing a mogroside.

Solution to the Problem

The present inventors conducted extensive research to solve the aforementioned problem, and found that, for example, koji mold-derived glycoside hydrolases ASBGL2, AOBGL2, AOBGL1, and ASBGL1 have an activity to cleave a β-1,6-glucoside bond of mogroside V, thus completing the present invention.

In summary, the present invention is as set forth below.

[1]
A method for preparing a mogroside having no β-1,6-glucoside bond comprising the step of reacting a protein selected from the group consisting of proteins (a) to (c) shown below with a mogroside having at least one β-1,6-glucoside bond, thereby cleaving said β-1,6-glucoside bond:

(a) a protein consisting of an amino acid sequence selected from the group consisting of SEQ ID NO: 4, SEQ ID NO: 8, SEQ ID NO: 12, and SEQ ID NO: 16;

(b) a protein consisting of an amino acid sequence selected from the group consisting of SEQ ID NO: 4, SEQ ID NO: 8, SEQ ID NO: 12, and SEQ ID NO: 16, wherein 1 to 84 amino acids have been deleted, substituted, inserted, and/or added, and having an activity to cleave the β-1,6-glucoside bond of a mogroside; and (c) a protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of the mogroside.

[2]
The method according to [1] above, wherein the protein selected from the group consisting of proteins (a) to (c) further includes a secretory signal peptide.

[3]
The method according to [1] or [2] above, wherein the mogroside having at least one β-1,6-glucoside bond further has at least one β-1,2-glucoside bond.

[4]
The method according to [3] above, wherein the mogroside having at least one β-1,6-glucoside bond and at least one β-1,2-glucoside bond is selected from mogroside V, siamenoside I, mogroside IV, and mogroside IIIA$_1$.

[5]
The method according to [4] above, wherein the mogroside having no β-1,6-glucoside bond is selected from mogroside IIIE and mogroside IIA.

[6]
A method for producing a mogroside having no β-1,6-glucoside bond comprising culturing a non-human transformant obtained by introducing a polynucleotide selected from the group consisting of polynucleotides (a) to (e) shown below into a host producing a mogroside having at least one β-1,6-glucoside bond:

(a) a polynucleotide consisting of a nucleotide sequence selected from the group consisting of positions 61 to 2601 of SEQ ID NO: 1, positions 61 to 2707 of SEQ ID NO: 2, positions 61 to 2601 of SEQ ID NO 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14;

(b) a polynucleotide encoding a protein consisting of an amino acid sequence selected from the group consisting of SEQ ID NO: 4, SEQ ID NO: 8, SEQ ID NO: 12, and SEQ ID NO: 16;

(c) a polynucleotide encoding a protein consisting of an amino acid sequence selected from the group consisting of SEQ ID NO: 4, SEQ ID NO: 8, SEQ ID NO: 12, and SEQ ID NO: 16, wherein. 1 to 84 amino acids have been deleted, substituted, inserted, and/or added, and having an activity to cleave a β-1,6-glucoside bond of a mogroside;

(d) a polynucleotide encoding a protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside; and (e) a polynucleotide which hybridizes under highly stringent conditions to a polynucleotide consisting of a nucleotide sequence complementary to a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, the polynucleotide encoding a protein having an activity to cleave a β-1,6-glucoside bond of a mogroside.

[7]
The method according to [6] above, wherein the polynucleotide selected from the group consisting of polynucleotides to (e) further includes a polynucleotide consisting of a nucleotide sequence encoding a secretory signal peptide.

[8]
The method according to [7] above, wherein the polynucleotide consisting of a nucleotide sequence encoding a secretory signal peptide is a polynucleotide consisting of a nucleotide sequence set forth in any of positions 1 to 60 of SEQ ID NO: 1, positions 1 to 60 of SEQ ID NO: 5, positions 1 to 57 of SEQ ID NO: 9, positions 1 to 57 of SEQ ID NO: 13, SEQ ID NO: 43, SEQ ID NO: 45, and SEQ ID NO: 47.

[9]
The method according to [8] above, wherein the polynucleotide containing the polynucleotide consisting of a nucleotide sequence encoding a secretory signal peptide consists of a nucleotide sequence set forth in any of SEQ ID NO: 1, SEQ ID NO: 2, SEQ ID NO: 5, SEQ ID NO: 6, SEQ ID NO: 9, SEQ ID NO: 10, SEQ ID NO: 13, SEQ ID NO: 14, and SEQ ID NOS: 17 to 25.

[10]
The method according to any one of [6] to [9] above, wherein the polynucleotide is inserted into an expression vector.

[11]
The method according to any one of [6] to [10] above, wherein the transformant is transformed yeast or a transformed plant.

[12]
A method for preparing a mogroside having no β-1,6-glucoside bond comprising the step of contacting an enzyme agent derived from a non-human transformed cell obtained by introducing, into a host cell, a polynucleotide selected from the group consisting of polynucleotides (a) to (e) shown below, with a mogroside having at least one β-1,6-glucoside bond, thereby cleaving said β-1,6-glucoside bond:

(a) a polynucleotide consisting of a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2596 of SEQ ID NO: 13, and positions 58 to 2892 of SEQ ID NO: 14;

(b) a polynucleotide encoding a protein consisting of an amino acid sequence selected from the group consisting of SEQ ID NO: 4, SEQ ID NO: 8, SEQ ID NO: 12, and SEQ ID NO: 16;

(c) a polynucleotide encoding a protein consisting of an amino acid sequence selected from the group consisting of SEQ ID NO: 4, SEQ ID NO: 8, SEQ ID NO: 12, and SEQ ID NO: 16, wherein 1 to 84 amino acids have been deleted, substituted, inserted, and/or added, and having an activity to cleave a β-1,6-glucoside bond of a mogroside;

(d) a polynucleotide encoding a protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside; and (e) a polynucleotide which hybridizes under highly stringent conditions to a polynucleotide consisting of a nucleotide sequence complementary to a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, the polynucleotide encoding a protein having an activity to cleave a β-1,6-glucoside bond of a mogroside.

[13]
The method according to [12] above, wherein the polynucleotide selected from the group consisting of polynucleotides (a) to (e) further includes a polynucleotide consisting of a nucleotide sequence encoding a secretory signal peptide.

[14]

The method according to [13] above, wherein the polynucleotide consisting of a nucleotide sequence encoding a secretory signal peptide is a polynucleotide consisting of a nucleotide sequence set forth in any of positions 1 to 60 of SEQ ID NO: 1, positions 1 to 60 of SEQ ID NO: 5, positions 1 to 57 of SEQ ID NO: 9, positions 1 to 57 of SEQ ID NO: 13, SEQ ID NO: 43, SEQ ID NO: 45, and SEQ ID NO: 47.

[15]

The method according to [14] above, wherein the polynucleotide containing the polynucleotide consisting of a nucleotide sequence encoding a secretory signal peptide consists of a nucleotide sequence set forth in any of SEQ ID NO: 1, SEQ ID NO: 2, SEQ ID NO: 5, SEQ ID NO: 6, SEQ ID NO: 9, SEQ ID NO: 10, SEQ ID NO: 13, SEQ ID NO: 14, and SEQ ID NOS: 17 to 25.

[16]

The method according to any one of [12] to [15] above, wherein the polynucleotide is inserted into an expression vector.

[17]

The method according to any one of [12] to [16] above, wherein the transformed cell is a transformed bacterium or transformed yeast.

[18]

The method according to [12] to [17] above, wherein the mogroside having at least one β-1,6-glucoside bond further has at least one β-1,2-glucoside bond.

[19]

The method according to [18] above, wherein the mogroside having at least one β-1,6-glucoside bond and least one β-1,2-glucoside bond is selected from mogroside V, siamenoside I, mogroside IV, and mogroside $IIIA_1$.

[20]

The method according to [19] above, wherein the mogroside having no β-1,6-glucoside bond is selected from mogroside IIIE and mogroside IIA.

Effect of the Invention

The present invention provides a novel method for preparing a mogroside. Moreover, the transformant of the present invention can produce a mogroside having no β-1,6-glucoside bond. Because the transformant of the present invention has a high content of the mogroside having no β-1,6-glucoside bond, the mogroside having no β-1,6-glucoside bond can be efficiently extracted and purified therefrom.

BRIEF DESCRIPTION OF DRAWINGS

FIG. 1 shows secretory signal peptide sequences (DNA sequences and amino acid sequences) of yeast secretory proteins, wherein A shows MF(ALPHA)1 (YPL187W), B shows PHO5 (YBR093C), and C shows SUC2 (YIL162W).

FIG. 2 shows the results of LC analysis of reaction products obtained by reacting mogroside V with enzyme solutions, wherein A shows the results obtained with the enzyme solution ASBGL2, B shows the results obtained with the enzyme solution AOBGL1, and C shows the results obtained with the control, and (1) shows mogroside V, and (2) shows mogroside IIIE.

FIG. 3 shows the results of LC analysis of reaction products obtained by reacting mogroside IIIE with enzyme solutions, wherein A shows the results obtained with the enzyme solution AOBGL1, and B shows the results obtained with the control, and (1) shows mogroside IIIE, and (2) shows a mogrol glycoside (diglycoside).

FIG. 4 shows the results of LC-MS analysis of reaction products obtained by reacting mogroside IIIE with enzyme solutions, wherein A shows the results obtained with the enzyme solution AOBGL1, and B shows the results obtained with the control, and (1) shows mogroside IIIE, (2) shows a mogrol glycoside (diglycoside), and (3) shows a mogrol glycoside (monoglycoside).

FIG. 5-1 shows alignments of amino acid sequences for AOBGL1 protein (AOBGL1p), ASBGL1 protein (ASBGL1p), AOBGL2 protein (AOBGL2p), and ASBGL2 (ASBGL2p) protein, wherein the double-underlined parts correspond to estimated secretory signal sequences.

FIG. 5-2 is a continuation of FIG. 5-1.

DESCRIPTION OF EMBODIMENTS

The present invention will be hereinafter described in detail. The following embodiments are illustrative of the present invention, and are not intended to limit the present invention. The present invention can be carried out in various manners, without departing from the gist of the invention.

Note that all documents, as well as laid-open application publications, patent application publications, and other patent documents cited herein shall be incorporated herein by reference. The present specification incorporates the contents of the specification and the drawings of Japanese Patent Application No. 2015-008508, filed on Jan. 20, 2015, from which the present application claims priority.

"ASBGL2" designates a koji mold-derived β-glucosidase; the cDNA sequence, the genomic DNA sequence, the amino acid sequence, and the amino acid sequence of the mature protein are shown in SEQ ID NO: 1, SEQ ID NO: 2, SEQ ID NO: 3, and SEQ ID NO: 4, respectively.

"AOBGL2" designates a koji mold-derived β-glucosidase; the cDNA sequence, the genomic DNA sequence, the amino acid sequence, and the amino acid sequence of the mature protein are shown in SEQ ID NO: 5, SEQ ID NO: 6, SEQ ID NO: 7, and SEQ ID NO: 8, respectively.

"AOBGL1" designates a koji mold-derived β-glucosidase; the cDNA sequence, the genomic DNA sequence, the amino acid sequence, and the amino acid sequence of the mature protein are shown in SEQ ID NO: 9, SEQ ID NO: 10, SEQ ID NO: 11, and SEQ ID NO: 12, respectively.

"ASBGL1" designates a koji mold-derived β-glucosidase; the cDNA sequence, the genomic DNA sequence, the amino acid sequence, and the amino acid sequence of the mature protein are shown in SEQ ID NO: 13, SEQ ID NO: 14, SEQ ID NO: 15, and SEQ ID NO: 16, respectively.

These polynucleotides and enzymes can be obtained using methods described in the Examples below, known genetic engineering techniques, or known synthesis techniques, for example.

1. Method for Preparing a Mogroside

The present invention provides a method for preparing a mogroside having no β-1,6-glucoside bond comprising the step of reacting a protein selected from the group consisting of proteins (a) to (c) shown below (hereinafter referred to as "the protein of the present invention") with a mogroside having at least one β-1,6-glucoside bond, thereby cleaving said β-1,6-glucoside bond:

(a) a protein consisting of an amino acid sequence selected from the group consisting of SEQ ID NO: 4, SEQ ID NO: 8, SEQ ID NO: 12, and SEQ ID NO: 16;

(b) a protein consisting of an amino acid sequence selected from the group consisting of SEQ ID NO: 4, SEQ ID NO: 8, SEQ ID NO: 12, and SEQ ID NO: 16, wherein 1 to 84 amino acids have been deleted, substituted, inserted, and/or added, and having an activity to cleave a β-1,6-glucoside bond of a mogroside; and (c) a protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside.

While the protein shown in (b) or (c) above is typically a variant of a protein consisting of an amino acid sequence selected from the group consisting of SEQ ID NO: 4, SEQ ID NO: 8, SEQ ID NO: 12, and SEQ ID NO: 16, these proteins also include proteins that can be artificially obtained using site-directed mutagenesis as described in, for example, "Sambrook & Russell, Molecular Cloning: A Laboratory Manual Vol. 4, Cold Spring Harbor Laboratory Press 2012", "Ausubel, Current Protocol, in Molecular Biology, John Wiley & Sons 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", and "Proc. Natl. Acad. Sci. USA, 82, 488 (1985)".

Examples of the "protein consisting of an amino acid sequence selected from the group consisting of SEQ ID NO: 4, SEQ ID NO: 8, SEQ ID NO: 12, and: SEQ ID NO: 16, wherein 1 to 84 amino acids have been deleted, substituted, inserted, and/or added, and having an activity to cleave a β-1,6-glucoside bond of a mogroside" include a protein consisting of an amino acid sequence selected from the group consisting of SEQ ID NO: 4, SEQ ID NO: 8, SEQ ID NO: 12, and SEQ ID NO: 16, wherein, for example, 1 to 84, 1 to 80, 1 to 75, 1 to 70, 1 to 65, 1 to 60, 1 to 55, 1 to 50, 1 to 49, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (one to several), 1 to 8, 1 to 7, 1 to 6, 1 to 5, 1 to 4, 1 to 3, 1 or 2, or 1 amino acid residue has been deleted, substituted, inserted, and/or added, and having an activity to cleave a β-1,6-glucoside bond of a mogroside. In general, the number of deleted, substituted, inserted, and/or added amino acid residues is preferably smaller.

Examples of such proteins include a protein having an amino acid sequence sharing 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside. In general, the value of sequence identity is preferably greater.

Examples of the "protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside" include a protein having an amino acid sequence sharing 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside. In general, the value of sequence identity is preferably greater.

As used herein, the phrase "an activity to cleave a β-1,6-glucoside bond of a mogroside" refers to the activity to cleave a β-1,6-glucoside bond formed between glucose units in a mogroside, which is a glycoside wherein glucose is linked to the aglycone, mogrol. The protein of the present invention may also have an activity to cleave a β-1,2-glucoside bond in the mogroside. In this case also, however, the protein of the present invention preferentially cleaves the β-1,6-glucoside bond compared to the β-1,2-glucoside bond.

The activity to cleave a β-1,6-glucoside bond of a mogroside can be confirmed by reacting the protein of the present invention with the mogroside having at least one β-1,6-glucoside bond, purifying the resulting reaction product, and analyzing the purified product using a known technique such as liquid chromatography (LC). If a mogroside having a β-1,2-glucoside bond in addition to the at least one β-1,6-glucoside bond is used for reaction with the protein of the present invention, it can be confirmed whether the protein of the present invention preferentially cleaves the β-1,6-glucoside bond compared to the β-1,2-glucoside bond.

The phrase "an amino acid sequence selected from the group consisting of SEQ ID NO: 4, SEQ ID NO: 8, SEQ ID NO: 12, and SEQ ID NO: 16, wherein 1 to 84 amino acid residues have been deleted, substituted, inserted, and/or added" means that 1 to 84 amino acid residues have been deleted, substituted, inserted, and/or added at any of the 1st to 84th positions in the same amino acid sequence, wherein two or more of deletion, substitution, insertion, and addition may occur simultaneously.

Examples of amino acid residues that are interchangeable are shown below. The amino acid residues included in the same group are interchangeable.

Group A: leucine, isoleucine, norleucine, valine, norvaline, alanine, 2-aminobutanoic acid, methionine, o-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

The protein of the present invention in some embodiments does not contain a secretory signal peptide, because the secretory signal peptide is cleaved. The protein of the present invention in some other embodiments may further contain a secretory signal peptide, because the secretory signal peptide remains uncleaved. When the protein of the present invention contains a secretory signal peptide, it preferably contains the secretory signal peptide at its N-terminus. The secretory signal peptide refers to a peptide domain that serves to cause extracellular secretion of a protein bound to the secretory signal peptide. Amino acid sequences of such secretory signal peptides and polynucleotide sequences encoding such amino acid sequences have been well known and reported in the art.

The protein of the present invention can be obtained by, for example, expressing a polynucleotide encoding the protein of the present invention (see "the polynucleotide of the present invention" described below) in appropriate host cells, although it can also be produced by a chemical synthesis method such as the Fmoc method (fluorenylmethyloxycarbonyl method) or the tBoc method (t-butyloxycarbonyl method). The protein of the present invention can also be chemically synthesized using a peptide synthesizer from AAPPTec LLC, Perkin Elmer Inc., Protein Technologies Inc., PerSeptive Biosystems, Applied Biosystems, or SHIMADZU CORPORATION, for example.

As used herein, the term "mogroside" refers to a glycoside wherein glucose is linked to the aglycone, mogrol. Examples of mogrol and mogrosides are shown below:

[Formula 1]

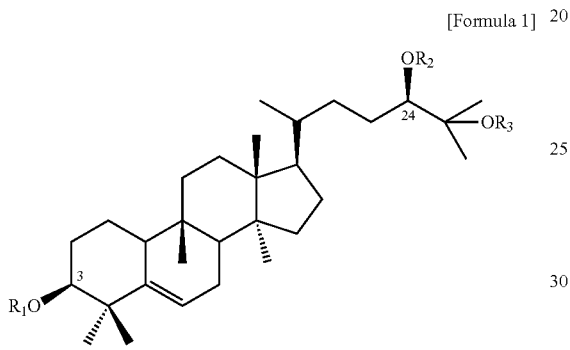

[Formula 2]

| Compound Name | $R_1$ | $R_2$ | $R_3$ |
|---|---|---|---|
| Mogroside V | Glc6-Glc- | Glc6Glc2 (Glc)- | H |
| Siamenoside I | Glc- | Glc6Glc2 (Glc)- | H |
| Mogroside IV | Glc6-Glc- | Glc2-Glc- | H |
| Mogroside IVA | Glc6-Glc- | Glc6-Glc- | H |
| Mogroside III | Glc- | Glc6-Glc- | H |
| Mogroside IIIA$_1$ | H | Glc6Glc2 (Glc)- | H |
| Mogroside IIIA$_2$ | Glc6-Glc- | Glc- | H |
| Mogroside IIIE | Glc- | Glc2-Glc- | H |
| Mogroside IIA | H | Glc2-Glc- | H |
| Mogroside IIA$_1$ | H | Glc6-Glc- | H |
| Mogroside IIA$_2$ | Glc6-Glc- | H | H |
| Mogroside IIB | Glc- | H | Glc- |
| Mogroside IIE | Glc- | Glc- | H |
| Mogroside IA$_1$ | H | Glc- | H |
| Mogroside IE$_1$ | Glc- | H | H |
| Mogrol | H | H | H |

In the table shown above, "Glc6-Glc-" designates the inclusion of a β-1,6-glucoside bond. "Glc2-Glc-" designates the inclusion of β-1,2-glucoside bond. "(Glc6Glc2(Glc)-" designates the inclusion of a β-1,6-glucoside bond and a β-1,2-glucoside bond.

Among the mogrosides, the mogroside having at least one (e.g., 1 or 2) β-1,6-glucoside bond is a mogroside selected from mogroside V, siamenoside I, mogroside IV, mogroside IVA, mogroside III, mogroside IIIA$_1$, mogroside IIIA$_2$, mogroside IIA$_1$, and mogroside IIA$_2$, for example. The mogroside having at least one β-1,6-glucoside bond preferably further has a mogroside having at least one (e.g., 1) β-1,2-glucoside bond. The mogroside having at least one β-1,6-glucoside bond and at least one β-1,2-glucoside bond is a mogroside selected from mogroside V, siamenoside I, mogroside IV, and mogroside IIIA$_1$, for example, and is preferably mogroside V.

The method for preparing a mogroside according to the present invention cleaves said β-1,6-glucoside bond, thereby producing a mogroside having no 1,6-glucoside bond (hereinafter referred to as "the mogroside of the present invention"). The mogroside having no β-1,6-glucoside bond varies depending on the starting material, "the mogroside having a β-1,6-glucoside bond", as follows. Examples thereof are shown below:

[Formula 3]

| Starting Material | Mogroside of the Present Invention |
|---|---|
| Mogroside V | Mogroside IIIE |
| Siamenoside I | Mogroside IIIE |
| Mogroside IV | Mogroside IIIE |
| Mogroside III | Mogroside IIE |
| Mogroside IIIA$_1$ | Mogroside IIA |
| Mogroside IIIA$_2$ | Mogroside IIE |
| Mogroside IIA$_1$ | Mogroside IA$_1$ |
| Mogroside IIA$_2$ | Mogroside IE$_1$ |

In the method for preparing a mogroside of the present invention, the mogroside having at least one β-1,6-glucoside bond for use as the starting material can be obtained by extraction from fruits of *Siraitia grosvenorii*, followed by purification, or may be prepared using a known method (e.g., a method described in Patent Literature 1) or a method analogous thereto. Alternatively, a commercially available product may be used as the mogroside having at least one β-1,6-glucoside bond for use as the starting material.

In some embodiments of the present invention, the β-1,6-glucoside bond of a mogroside selected from mogroside V, siamenoside I, mogroside IV, and mogroside IIIA$_1$ is cleaved to produce a mogroside selected from mogroside IIIE and mogroside IIA. In the most preferred embodiment of the present invention, the β-1,6-glucoside bond of mogroside V is cleaved to produce mogroside IIIE.

As described above, the protein of the present invention may further have the activity to cleave a β-1,2-glucoside bond in a mogroside. In this case, the mogroside of the present invention may include a mogroside having no β-1,6-glucoside bond or β-1,2-glucoside bond. The mogroside having no β-1,6-glucoside bond or β-1,2-glucoside bond is mogroside IIB, mogroside IIE, mogroside IA$_1$, or mogroside IE$_1$, for example, and is preferably mogroside IIE. For example, mogroside IIE is obtained by further cleaving the β-1,2-glucoside bond of mogroside IIIE. Mogroside IA$_1$ is obtained by further cleaving the β-1,2-glucoside bond of mogroside IIA.

The method for preparing a mogroside according to the present invention comprises the step of reacting the protein of the present invention with a mogroside having at least one β-1,6-glucoside bond, thereby cleaving said β-1,6-glucoside bond. The method of the present invention may further include the step of purifying the mogroside having no β-1,6-glucoside bond produced in the preceding step.

The mogroside having no β-1,6-glucoside bond can be purified using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), gas chromatography, time-of-flight mass spectrometry (TOF-MS), and ultra (high) performance liquid chromatography (UPLC).

When the mogroside of the present invention contains a mogroside having no β-1,6-glucoside bond but having at least one β-1,2-glucoside bond and a mogroside having no β-1,6-glucoside bond or β-1,2-glucoside bond, these mogrosides may be separated and purified, as required, using a known method. The mogroside having no β-1,6-glucoside bond but having at least one β-1,2-glucoside bond is mogroside IIIE or mogroside IIA, for example. The mogroside having no β-1,6-glucoside bond or β-1,2-glucoside bond is as described above.

2. Method for Producing the Mogroside of the Present Invention Using a Non-Human Transformant The protein of the present invention is a koji mold-derived secretory enzyme or a variant thereof, and is expected to have high activity in an extracellular environment, as with koji mold. In this case, the mogroside of the present invention can be produced by introducing a polynucleotide encoding the protein of the present invention (see "the polynucleotide of the present invention" described below) into host cells derived from bacteria, fungi, plants, insects, non-human mammals, or the like, for extracellular expression of the protein of the present invention, and by reacting the protein of the present invention with a mogroside having a β-1,6-glucoside bond. Alternatively, depending on the host, the mogroside of the present invention can be produced by expressing the protein of the present invention in the host cells.

Thus, the present invention provides a method for producing a mogroside having no β-1,6-glucoside bond comprising culturing a non-human transformant (hereinafter referred to as "the transformant of the present invention") obtained by introducing a polynucleotide selected from the group consisting of polynucleotides (a) to (e) shown below (hereinafter referred to as "the polynucleotide of the present invention") into a host producing a mogroside having at least one β-1,6-glucoside bond:

(a) a polynucleotide consisting of a nucleotide sequence selected from the croup consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14;

(b) a polynucleotide encoding a protein consisting of an amino acid sequence selected from the group consisting of SEQ ID NO: 4, SEQ ID NO: 8, SEQ ID NO: 12, and SEQ ID NO: 16;

(c) a polynucleotide encoding a protein consisting of an amino acid sequence selected from the group consisting of SEQ ID NO: 4, SEQ ID NO: 8, SEQ ID NO: 12, and SEQ ID NO: 16, wherein 1 to 84 amino acids have been deleted, substituted, inserted, and/or added, and having an activity to cleave a β-1,6-glucoside bond of a mogroside;

(d) a polynucleotide encoding a protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside; and (e) a polynucleotide which hybridizes under highly stringent conditions to a polynucleotide consisting of a nucleotide sequence complementary to a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, the polynucleotide encoding a protein having an activity to cleave a β-1,6-glucoside bond of a mogroside.

As used herein, the term "polynucleotide" refers to DNA or RNA.

Examples of the polynucleotide encoding the protein consisting of the amino acid sequence set forth in SEQ ID NO: 4 include a polynucleotide consisting of the nucleotide sequence from positions 61 to 2601 of SEQ In NO: 1. Examples of the polynucleotide encoding the protein consisting of the amino acid sequence set forth in SEQ ID NO: 8 include a polynucleotide consisting of the nucleotide sequence from positions 61 to 2601 of SEQ ID NO: 5. Examples of the polynucleotide encoding the protein consisting of the amino acid sequence set forth in SEQ ID NO: 12 include a polynucleotide consisting of the nucleotide sequence from positions 58 to 2586 of SEQ ID NO: 9. Examples of the polynucleotide encoding the protein consisting of the amino acid sequence set forth in SEQ ID NO: 16 include a polynucleotide consisting of the nucleotide sequence from positions 58 to 2586 of SEQ ID NO: 13.

Examples of the "protein consisting of an amino acid sequence selected from the group consisting of SEQ ID NO: 4, SEQ ID No: 8, SEQ ID NO: 12, and SEQ ID NO: 16, wherein 1 to 84 amino acids have been deleted, substituted, inserted, and/or added, and having an activity to cleave a β-1,6-glucoside bond of a mogroside" are as described above.

Examples of the "protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside" are as described above.

As used herein, the phrase "a polynucleotide which hybridizes under highly stringent conditions" refers to a polynucleotide obtained by means of a hybridization method such as colony hybridization, plaque hybridization, or Southern hybridization, using, as a probe, all of or a portion of a polynucleotide consisting of a nucleotide sequence complementary to a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, or of a polynucleotide consisting of a nucleotide sequence complementary to a nucleotide sequence encoding an amino acid sequence selected from the group consisting of SEQ ID NO: 4, SEQ ID NO: 8, SEQ ID NO: 12, and SEQ ID NO: 16. For hybridization, methods as described in "Sambrook & Russell, Molecular Cloning: A Laboratory Manual Vol. 4, Cold Spring Harbor, Laboratory Press 2012" and "Ausubel, Current Protocols in Molecular Biology, John Wiley & Sons 1987-1997", for example, can be used.

As used herein, the term "highly stringent conditions" refers to, for example, the following conditions: 5×SSC, 5×Denhardt's solution, 0.5% SDS, 50% formamide, 50° C.; 0.2×SSC, 0.1% SDS, 60° C.; 0.2×SSC, 0.1% SDS, 62° C.; or 0.2×SSC, 0.1% SDS, 65° C.; although not limited thereto. Under these conditions, it is expected that DNA having a higher sequence identity will be efficiently obtained at a higher temperature. Note, however, that a plurality of factors such as temperature, probe concentration, probe length, ionic strength, time, and salt concentration are considered to affect the stringency of hybridization, and a person skilled in the art will be able to achieve the same stringency by selecting these factors as appropriate.

When a commercially available kit is used for hybridization, the Alkphos Direct Labelling and Detection System (GE Healthcare), for example, can be used. In this case, hybridization is accomplished in accordance with the protocol attached to the kit, i.e., a membrane may be incubated overnight with a labeled probe and then washed with a primary washing buffer containing 0.1% (w/v) SDS at 55 to 60° C. to detect the hybridized DNA. Alternatively, when a commercially available reagent (e.g., PCR labeling mix (Roche Diagnostics)) is used for digoxigenin (DIG) labeling of a probe during probe preparation based on all of or a portion of a nucleotide sequence complementary to a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, or of a nucleotide sequence complementary to a nucleotide sequence encoding an amino acid sequence selected from the group consisting of SEQ ID NO: 4, SEQ ID NO: 8, SEQ ID NO: 12, and SEQ ID NO: 16, the DIG nucleic acid detection kit (Roche Diagnostics) may be used for detection of hybridization.

In addition to those described above, examples of other hybridizable polynucleotides include DNA sharing 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with DNA of a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, or DNA encoding an amino acid sequence selected from the group consisting of SEQ ID NO: 4, SEQ ID NO: 8, SEQ ID NO: 12, and SEQ ID NO: 16, as calculated by the homology search software BLAST using default parameters.

Note that the sequence identity of amino acid sequences or nucleotide sequences can be determined using the BLAST algorithm developed by Karlin and Altschul (Basic Local Alignment Search Tool) (Proc. Natl. Acad. Sci. USA 872264-2268, 1990; Proc Natl Acad Sci USA 90: 5873, 1993). When BLAST is used, default parameters in each program are used.

The polynucleotide of the present invention may further contain a polynucleotide consisting of a nucleotide sequence encoding a secretory signal peptide. Preferably, the polynucleotide of the present invention contains, at its 5' end, the polynucleotide consisting of a nucleotide sequence encoding a secretory signal peptide. The secretory signal peptide is as described above. Such a secretory signal peptide can be selected as appropriate, depending on the host into which the polynucleotide of the present invention is to be introduced. For example, when the host is yeast, examples of secretory signal peptides include yeast-derived secretory signal peptides, such as MF(ALPHA)1 signal peptide, PHO5 signal peptide, and SUC2 signal peptide. Examples of polynucleotides encoding MF(ALPHA)1 signal peptide, PHO5 signal peptide, and SUC2 signal peptide include polynucleotides consisting of the nucleotide sequences shown in SEQ ID NO: 43, SEQ ID NO: 45, and SEQ ID NO: 47, respectively. The amino acid sequences of MF(ALPHA)1 signal peptide, PHO5 signal peptide, and SUC2 signal peptide are shown in SEQ ID NO: 44, SEQ ID NO: 46, and SEQ ID NO: 48, respectively. When the host is koji mold, examples of secretory signal peptides include koji mold-derived signal peptides, such as a peptide consisting of the amino acid sequence from positions 1 to 20 of SEQ ID NO: 3, a peptide consisting of the amino acid sequence from positions 1 to 20 of SEQ ID NO: 7, a peptide consisting of the amino acid sequence from positions 1 to 19 of SEQ ID NO: 11, and a peptide consisting of the amino acid sequence from positions 1 to 19 of SEQ ID NO: 15. The polynucleotide encoding the peptide consisting of the amino acid sequence from positions 1 to 20 of SEQ ID NO: 3, the polynucleotide encoding the peptide consisting of the amino acid sequence from positions 1 to 20 of SEQ ID NO: 7, the polynucleotide encoding the peptide consisting of the amino acid sequence from positions 1 to 19 of SEQ ID NO: 11, and the polynucleotide encoding the peptide consisting of the amino acid sequence from positions 1 to 19 of SEQ ID NO: 15 are polynucleotides consisting of nucleotide sequences selected from the group consisting of positions 1 to 60 of SEQ ID NO: 1, positions 1 to 60 of SEQ ID NO: 5, positions 1 to 57 of SEQ ID NO: 9, and positions 1 to 57 of SEQ ID NO: 13, respectively, for example.

The polynucleotide of the present invention containing the polynucleotide consisting of a nucleotide sequence encoding a secretory signal peptide is a polynucleotide consisting of a nucleotide sequence set forth in any of SEQ ID NO: 1, SEQ ID NO: 2, SEQ ID NO: 5, SEQ ID NO: 6, SEQ ID NO: 9, SEQ ID NO: 10, SEQ ID NO: 13, SEQ ID NO: 14, and SEQ ID NOS: 17 to 25, for example, and is preferably a polynucleotide consisting of a nucleotide sequence set forth in any of SEQ ID NOS: 17 to 25.

The above-described polynucleotide of the present invention can be obtained using a known genetic engineering technique or a known synthesis technique.

The polynucleotide of the present invention is preferably inserted into an appropriate expression vector for introduction into a host.

An appropriate expression vector is typically configured to include:

(i) a promoter transcribable in host cells;
(ii) the polynucleotide of the present invention ligated to the promoter; and
(iii) an expression cassette containing, as constituent elements, signals that function in the host cells for transcription termination and polyadenylation of an RNA molecule.

Examples of methods for preparing such an expression vector include, although not particularly limited to, using plasmids, phages, cosmids, or the like.

The specific type of the vector is not particularly limited, and any vector expressible in host cells may be selected as appropriate. Specifically, an appropriate promoter sequence may be selected in accordance with the type of the host cells to ensure the expression of the polynucleotide of the present invention, and this promoter sequence and the polynucleotide of the present invention may then be integrated into any of various plasmids, for example, for use as an expression vector.

The expression vector of the present invention contains an expression control region (e.g., a promoter, a terminator, and/or a replication origin), depending on the type of the host into which the expression vector is to be introduced. For bacterial expression vectors, commonly used promoters (e.g., trc promoter, tac promoter, and lac promoter) are used. Examples of yeast promoters include glyceraldehyde-3-phosphate dehydrogenase promoter and PHO5 promoter. Examples of filamentous fungi promoters include amylase and trpC. Moreover, examples of promoters for expression of a target gene in plant cells include cauliflower mosaic virus 35S RNA promoter, rd29A gene promoter, rbcS promoter, and mac-1 promoter configured to have the enhancer sequence of the above-mentioned cauliflower mosaic virus 35S RNA promoter at the 5'-side of *Agrobacterium*-derived mannopine synthase promoter sequence. Examples of promoters for animal cell hosts include viral promoters (e.g., SV40 early promoter and SV40 late promoter).

The expression vector preferably contains at least one selection marker. For use as such a marker, auxotrophic markers (ura5, niaD), drug resistance markers (hygromycine, zeocin), geneticin resistance gene (G418r), copper resistance gene (CUP1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991), and the like are available.

While the method for preparing (producing) the transformant of the present invention is not particularly limited, the transformant of the present invention may be prepared by, for example, introducing an expression vector containing the polynucleotide of the present invention into a host to transform the host. The host to be used herein is not particularly limited as long as it produces a mogroside having at least one β-1,6-glucoside bond, and may include not only a plant such as *Siraitia grosvenorii* that produces a mogroside having at least one β-1,6-glucoside bond, but also a host obtained by introducing a gene required for the production of a mogroside having at least one β-1,6-glucoside bond into cells or an organism that does not originally produce a mogroside having at least one β-1,6-glucoside bond. Examples of the "gene required for the production of a mogroside having at least one β-1,6-glucoside bond" include genes having mogrol or mogroside synthesis activity as described in WO 2013/076577 and WO 2014/086842, for example. Any of conventionally known various types of cells or organisms can be suitably used as the cells or organism to be transformed. Examples of the cells to be transformed include bacteria such as *Escherichia coli*, yeast (budding yeast *Saccharomyces cerevisiae*, fission yeast *Schizosaccharomyces pombe*), filamentous fungi (koji mold *Aspergillus oryzae, Aspergillus sojae*), plant cells, and non-human animal cells. Appropriate media and conditions for culturing the above-described host cells are well known in the art. Likewise, the organism to be transformed is not particularly limited, and examples include various microorganisms, plants, and non-human animals described above as examples of host cells. The transformant is preferably yeast or a plant.

For transformation of the host cells, commonly used known methods can be used. For example, transformation can be accomplished using electroporation (Mackenxie, D. A. et al., Appl. Environ. Microbiol., vol. 66, p. 4655-4661, 2000), the particle delivery method (described in JP 2005-287403 A entitled "Breeding Method of Lipid Producing Fungi"), the spheroplast method (Proc. Natl. Acad. Sci. USA, vol. 75, p. 1929, 1978), the lithium acetate method (J. Bacteriology, vol. 153, p. 163, 1983), and other methods as described in Methods in yeast genetics, 2000 Edition: A Cold Spring Harbor Laboratory Course Manual, although not limited thereto.

For other standard molecular biological techniques, reference may be made to "Sambrook & Russell, Molecular Cloning: A Laboratory Manual Vol. 4, Cold Spring Harbor Laboratory Press 2012" and "Methods in Yeast Genetics, A laboratory manual (Cold Spring Harbor Laboratory Press, Cold Spring Harbor, N.Y.)", for example.

When the transformant is yeast, the transformant is obtained by introducing a recombinant vector containing the polynucleotide of the present invention into yeast such that a polypeptide encoded by the polynucleotide can be expressed. The yeast transformed with the polynucleotide of the present invention expresses a higher level of the protein of the present invention than in the wild-type counterpart. Thus, the expressed protein of the present invention reacts with the mogroside having at least one β-1,6-glucoside bond produced in the yeast, thereby cleaving said β-1,6-glucoside bond. As a result, the mogroside of the present invention having no β-1,6-glucoside bond is produced in the cells or culture medium of the yeast, preferably in the culture medium.

When the transformant is a plant, the transformant is obtained by introducing a recombinant vector containing the polynucleotide of the present invention into a plant such that a protein encoded by the polynucleotide can be expressed. The plant to be transformed in the present invention refers to any of whole plants, plant organs (e.g., leaves, petals, stems, roots, and seeds), plant tissues (e.g., epidermis, phloem, parenchyma, xylem, vascular bundles, palisade tissue, and spongy parenchyma) or plant cultured cells, or various forms of plant cells (e.g., suspension cultured cells), protoplasts, leaf sections, calli, and the like. The plant used for transformation is not particularly limited as long as it is a plant that produces a mogroside having at least one β-1,6-glucoside bond, or a plant that does not originally produce a mogroside having at least one β-1,6-glucoside bond, but can produce a mogroside having at least one β-1,6-glucoside bond through the introduction of a required gene. The plant used for transformation may be a plant in the class of either monocotyledons or dicotyledons. For gene transfer into the plant, transformation methods known to those skilled in the art are used (e.g., the *Agrobacterium*-mediated method, the gene gun method, the PEG-mediated method, and electroporation). The cells or plant tissues transfected with the gene are first selected by drug resistance such as hygromycin resistance, and then regenerated into plants using a standard method. The transformed cells can be regenerated into plants using a method known to those skilled in the art suitable for the type of the plant cells. The introduction of the polynucleotide of the present invention into the plant can be confirmed by using PCR, Southern hybridization, or Northern hybridization, for example. Once a transformed plant in which the polynucleotide of the present invention has been integrated into the genome is obtained, progeny plants can be produced by sexual or asexual reproduction of the plant. Moreover, seeds, fruits, cuttings, tubers, root tubers, rootstocks, calli, protoplasts or the like can be obtained from this plant or progeny plants thereof, or clones thereof, and used to achieve mass production of the plant. The plant transformed with the polynucleotide of the present invention (hereinafter, "the plant of the present invention") contains a greater amount of the protein of the present invention than in the wild-type counterpart. Thus, the protein of the present invention reacts with the mogroside having at least one β-1,6-glucoside bond produced in the plant of the present invention, thereby cleaving said β-1,6-glucoside bond. As a result, the mogroside of the present invention having no β-1,6-glucoside bond is produced in the plant.

The transformant in some embodiments of the present invention or the culture medium thereof has a content of the mogroside of the present invention higher than that in the wild-type counterpart, and an extract or the culture medium of the transformant contains a high concentration of the mogroside of the present invention. An extract of the transformant of the present invention can be obtained by homogenating the transformant with glass beads, a homogenizer, or a sonicator, for example, centrifuging the homogenate, and collecting the supernatant. When the mogroside of the present invention accumulates in the culture medium, the transformant and the culture supernatant may be separated using a standard method (e.g., centrifugation or filtration) after the completion of culture, thereby obtaining the culture supernatant containing the mogroside of the present invention.

The extract or culture supernatant thus obtained may be further subjected to a purification step. The mogroside of the present invention may be purified in accordance with a standard separation and purification method. Specific methods for purification are the same as described above.

3. Method for Preparing the Mogroside of the Present Invention Using an Enzyme Agent Derived from a Non-Human Transformed Cell The mogroside of the present invention can be produced by using an enzyme agent derived from transformed cells expressing the protein of the present invention, which are obtained by introducing the polynucleotide of the present invention into host cells derived from bacteria, fungi, plants, insects, non-human mammals, or the like, for expression of the protein of the present invention, i.e., by contacting the enzyme agent derived from transformed cells expressing the protein of the present invention with a mogroside having at least one β-1,6-glucoside bond. The "enzyme agent derived from transformed cells" is not limited as long as it is prepared using transformed cells, and contains the protein of the present invention. Examples of the enzyme agent include transformed cells themselves, a transformed cell homogenate itself, transformed cell culture supernatant itself, and a purified product thereof. Thus, the present invention provides a method for preparing a mogroside having no β-1,6-glucoside bond comprising the step of contacting an enzyme agent derived from a non-human transformed cell obtained by introducing, into a host cell, a polynucleotide selected from the group consisting of polynucleotides (a) to (e) shown below, with a mogroside having at least one β-1,6-glucoside bond, thereby cleaving said β-1,6-glucoside bond:

(a) a polynucleotide consisting of a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14;

(b) a polynucleotide encoding a protein consisting of an amino acid sequence selected from the group consisting of SEQ ID NO: 4, SEQ ID NO: 8, SEQ ID NO: 12, and SEQ ID NO: 16;

(c) a polynucleotide encoding a protein consisting of an amino acid sequence selected from the group consisting of SEQ ID NO: 4, SEQ ID NO: 8, SEQ ID NO: 12, and SEQ ID NO: 16, wherein 1 to 84 amino acids have been deleted, substituted, inserted, and/or added, and having an activity to cleave a β-1,6-glucoside bond of a mogroside;

(d) a polynucleotide encoding a protein having an amino acid sequence having 90% or more sequence identity to an amino acid sequence selected from the group consisting of SEQ ID NO: 4, SEQ ID NO: 8, SEQ ID NO: 12, and SEQ ID NO: 16, and having an activity to cleave a β-1,6-glucoside bond of a mogroside; and (e) a polynucleotide which hybridizes under highly stringent conditions to a polynucleotide consisting of a nucleotide sequence complementary to a nucleotide sequence selected from the group consisting of positions 61 to 2601 of SEQ ID NO: 1, positions 61 to 2707 of SEQ ID NO: 2, positions 61 to 2601 of SEQ ID NO: 5, positions 61 to 2708 of SEQ ID NO: 6, positions 58 to 2586 of SEQ ID NO: 9, positions 58 to 2891 of SEQ ID NO: 10, positions 58 to 2586 of SEQ ID NO: 13, and positions 58 to 2892 of SEQ ID NO: 14, the polynucleotide encoding a protein having an activity to cleave a β-1,6-glucoside bond of a mogroside.

The polynucleotide selected from the group consisting of polynucleotides (a) to (e) shown above is the polynucleotide of the present invention, which is the same as described above.

The polynucleotide of the present invention may further include a polynucleotide consisting of a nucleotide sequence encoding a secretory signal peptide. Preferably, the polynucleotide of the present invention includes, at its 5' end, the polynucleotide consisting of a nucleotide sequence encoding a secretory signal peptide. The secretory signal peptide and the polynucleotide consisting of a nucleotide sequence encoding the secretory signal peptide are the same as described above.

The polynucleotide of the present invention including the polynucleotide consisting of a nucleotide sequence encoding a secretory signal peptide is a polynucleotide consisting of a nucleotide sequence set forth in any of SEQ ID NO: 1, SEQ ID NO: 2, SEQ ID NO: 5, SEQ ID NO: 6, SEQ ID NO: 9, SEQ ID NO: 10, SEQ ID NO: 13, SEQ ID NO: 14, and SEQ ID NOS: 17 to 25, for example, and is preferably a polynucleotide consisting of a nucleotide sequence set forth in any of SEQ ID NOS: 17 to 25.

The polynucleotide of the present invention is preferably inserted into an appropriate expression vector for introduction into host cells. An appropriate expression vector is the same as described above.

While the method for preparing the transformed cells of the present invention is not particularly limited, the transformed cells of the present invention may be prepared by, for example, introducing an expression vector containing the polynucleotide of the present invention into host cells to transform the host cells. Any of conventionally known various types of cells or organisms can be suitably used as the cells to be transformed. Examples of the cells to be transformed include bacteria such as *Escherichia coli*, yeast (budding yeast *Saccharomyces cerevisiae*, fission yeast *Schizosaccharomyces pombe*), filamentous fungi (koji mold *Aspergillus oryzae, Aspergillus sojae*), plant cells, and non-human animal cells. Appropriate media and conditions for culturing the above-described host cells are well known in the art. The transformed cells are preferably bacteria such as *Escherichia coli* or yeast.

The method for transforming the host cells is as described above.

The transformed cells of the present invention are obtained by, for example, introducing a recombinant vector containing the polynucleotide of the present invention into the host cells such that a polypeptide encoded by the polynucleotide can be expressed. The host cells transformed with the polynucleotide of the present invention express a higher level of the protein of the present invention than in the wild-type counterpart. Thus, the mogroside of the present invention can be produced by using an enzyme agent derived from transformed cells expressing the protein of the present invention, i.e., by contacting the enzyme agent derived from transformed cells expressing the protein of the present invention with a mogroside having at least one β-1,6-glucoside bond.

The term "contact" refers to causing the enzyme agent derived from the transformed cells of the present invention and the mogroside having at least one β-1,6-glucoside bond to exist in the same reaction or culture system. The term "contact" includes, for example, adding the mogroside having at least one β-1,6-glucoside bond to a container containing the enzyme agent derived from the transformed cells of the present invention, mixing the enzyme agent derived from the transformed cells of the present invention and the mogroside having at least one β-1,6-glucoside bond, and adding the enzyme agent derived from the transformed cells of the present invention to a container containing the mogroside having at least one β-1,6-glucoside bond.

The terms "mogroside", "mogroside having at least one β-1,6-glucoside bond", and "mogroside having no β-1,6-glucoside bond" are the same as described above.

The mogroside having at least one β-1,6-glucoside bond preferably further has at least one β-1,2-glucoside bond. The mogroside having at least one β-1,6-glucoside bond and at least one β-1,2-glucoside bond is the same as described above.

The mogroside of the present invention thus obtained can be used for such purposes as the production of foods, sweeteners, flavors, pharmaceutical products, and industrial raw materials (raw materials for cosmetics, soaps, and the like), for example, in accordance with conventional methods.

Examples of foods include nutritional supplements, health foods, functional foods, foods for children, and foods for the elderly. As used herein, the term "foods" refers collectively to edible materials in the form of solids, fluids, liquids, and mixtures thereof.

Note that all documents, as well as laid-open application publications, patent application publications, and other patent documents cited herein shall be incorporated herein by reference.

EXAMPLES

The present invention will be more specifically described hereinafter with reference to examples, which are not intended to limit the scope of the present invention.

Materials

5-Bromo-4-chloro-3-indlyl β-D-glucopyranoside (hereinafter, "X-β-Glc") and 4-nitrophenyl β-D-glucopyranoside (hereinafter, "pNP-β-Glc") used in the following Examples are those available from SIGMA-Aldrich Corporation.

Search for Secretory β-Glucosidase Homologs

The koji mold genome data (PRJNA28175) was searched for β-glucosidase homologs. As a result, five genes encoding amino acid sequences having GH family 2 motifs, 28 genes encoding amino acid sequences having GH family 3 motifs, and seven genes encoding amino acid sequences having GH family 5 motifs were found. Among these genes, AO090001000544 and AO090009000356 were found from sequences encoding proteins having GH family 3 motifs and having secretory signals, and these genes were cloned.

Synthesis of cDNAs of Koji Mold

Koji mold *Aspergillus oryzae* var. *brunneus* (IFO30102) or *Aspergillus sojae* (NBRC4239) was inoculated to a GY plate (2% glucose, 0.5% yeast extract, and 2% agar), and cultured at 25° C. for 3 days. The grown cells were collected from the GY plate, and total RNA was extracted using RNeasy (QIAGEN). A cDNA was synthesized using the Superscript Double-Stranded cDNA Synthesis Kit (Life Technologies).

The following primers were designed based on the DNA sequence of AO090001000544:

```
                                      (SEQ ID NO: 26)
AOBGL2-1:    5'-GCGGCCGCATGGCTGCCTTCCCGGCCTA (SEQ ID NO: 27)
AOBGL2-2:    5'-GTCGACCTACAAAGTAGAACATCCCTCTCCAACC
```

For cloning of homologs of AO090001000544 of *Aspergillus sojae*, a BLAST search of the genome data of *Aspergillus sojae* (see DNA Res. 18(3), 165-176 (2011)) was performed to extract the corresponding sequence (SEQ ID NO: 2). The following primers were designed based on this DNA sequence:

ASBGL2-1: 5'-<u>GCGGCCGC</u>ATGGCTGCCTTTC- CGGC-CTAC (The underlined part represents the site of restriction enzyme BglII) (SEQ ID NO: 28)

ASBGL2-2: 5'-<u>GTCGAC</u>CTATAAAGTAGAACATC-CCTCCCCTACT (SEQ ID NO: 29)

The following primers were designed based on the DNA sequence of AO090009000356:

AOBGL1-1: 5'-<u>AGATCT</u>ATGAAGCTTGGTTGGAT-CGAGGT (The underlined part represents the site of restriction enzyme BglII) (SEQ ID NO: 30)

AOBGL1-2: 5'-<u>GTCGAC</u>TTACTGGGCCTTAGGC-AGCGA (The underlined part represents the site of restriction enzyme SalI) (SEQ ID NO: 31)

Approximately 2.6 kbp of a DNA fragment amplified by PCR using ExTaq (Takara Bio), using each of the cDNAs synthesized as described above as a template, was cloned using the TOPO-TA cloning Kit (Life Technologies). The templates, the primer combinations, and the genes obtained herein are as shown in Table 1. Each of the plasmids obtained herein was designated as pCR-AOBGL2, pCR-ASBGL2, pCR-AOBGL1, or pCR-ASBGL1.

TABLE 1

Templates, primer combinations, and obtained genes

| Template | Primer 1 | Primer 2 | Obtained gene |
| --- | --- | --- | --- |
| *A. oryzae* cDNA | AOBGL2-1 | AOBGL2-2 | AOBGL2 |
| *A. sojae* cDNA | ASBGL2-1 | ASBGL2-2 | ASBGL2 |

TABLE 1-continued

Templates, primer combinations, and obtained genes

| Template | Primer 1 | Primer 2 | Obtained gene |
|---|---|---|---|
| *A. oryzae* cDNA | AOBGL1-1 | AOBGL1-2 | AOBGL1 |
| *A. sojae* cDNA | AOBGL1-1 | AOBGL1-2 | ASBGL2 |

The sequence identities (%) of the cloned genes and identities (%) of estimated amino acid sequences encoded by the genes are as shown in Tables 2 and 3 below.

TABLE 2

DNA sequence identity

|  | AOBGL2 | ASBGL2 | AOBGL1 | ASBGL1 |
|---|---|---|---|---|
| AOBGL2 |  |  |  |  |
| ASBGL2 | 95.8 |  |  |  |
| AOBGL1 | 53.7 | 53.4 |  |  |
| ASBGL1 | 53.6 | 52.9 | 97.6 |  |

TABLE 3

Deduced amino acid sequence identity

|  | AOBGL2p | ASBGL2p | AOBGL1p | ASBGL1p |
|---|---|---|---|---|
| AOBGL2p |  |  |  |  |
| ASBGL2p | 98.2 |  |  |  |
| AOBGL1p | 42.7 | 42.5 |  |  |
| ASBGL1p | 42.7 | 42.5 | 98.7 |  |

FIGS. 5-1 and 5-2 show alignments of amino acid sequences for AOBGL2 protein (AOBGL2p), ASBGL2 protein (ASBGL2p), AOBGL1 protein (AOBGL1p), and ASBGL1 protein (ASBGL1p).

TABLE 4

|  | cDNA | Genome DNA | Amino acid sequence | Mature protein amino acid sequence |
|---|---|---|---|---|
| ASBGL2 | SEQ ID NO: 1 | SEQ ID NO: 2 | SEQ ID NO: 3 | SEQ ID NO: 4 |
| AOBGL2 | SEQ ID NO: 5 | SEQ ID NO: 6 | SEQ ID NO: 7 | SEQ ID NO: 8 |
| AOBGL1 | SEQ ID NO: 9 | SEQ ID NO: 10 | SEQ ID NO: 11 | SEQ ID NO: 12 |
| ASBGL2 | SEQ ID NO: 13 | SEQ ID NO: 14 | SEQ ID NO: 15 | SEQ ID NO: 16 |

Construction of Yeast Expression Vectors

A DNA fragment obtained by digesting the yeast expression vector pYE22m (Biosci. Biotech. Biochem., 59, 1221-1228, 1995) with restriction enzymes BamHI and SalI and approximately 2.6 kbp of a DNA fragment obtained by digesting pCR-ASBGL2, pCR-AOBGL1, or pCR-ASBGL1 with restriction enzymes BglII and SalI were ligated using the DNA Ligation Kit Ver.1 (Takara Bio), and the resulting plasmid was designated as pYE-ASBGL2, pYE-AOBGL1, or pYE-ASBGL1.

Acquisition of Transformed Yeast Strains

*S. cerevisiae* strain EH13-15 (trp1, MATα) (Appl. Microbiol. Biotechnol., 30, 515-520, 1989) was used as the parental strain for transformation.

Each of the plasmids pYE22m (control), pYE-ASBGL2 (for expression of ASBGL2), pYE-AOBGL1 (for expression of AOBGL1), and pYE-ASBGL1 (for expression of ASBGL1) was used to transform strain EH13-15 in accordance with the lithium acetate method. A strain that grew on SC-Trp (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil) agar medium (2% agar) was selected as the transformed strain.

The selected strain was applied to SC-Trp agar medium containing 0.004% of X-β-Glc, and cultured at 30° C. for 3 days. As a result, neither the strain transformed with any of the plasmids pYE-ASBGL2, pYE-AOBGL1p, and pYE-ASBGL1 nor the strain transformed with the control pYE22m was stained blue, and no X-β-Glc degrading activity was confirmed.

Meanwhile, one platinum loop of the selected strain was inoculated to 10 mL of SC-Trp liquid medium supplemented with 1/10 volume of 1 M potassium phosphate buffer, and cultured with shaking at 30° C. and 125 rpm for 2 days. The resulting culture was separated into the culture supernatant and cells by centrifugation. The cells were suspended in 50 mM sodium phosphate buffer (pH 7.0) containing 0.1% CHAPS solution and then homogenized with glass beads, and the supernatant obtained by centrifugation was used as the cell homogenate. The obtained culture supernatant or cell homogenate was examined for its pNP-β-Glc activity.

As a result, both the culture supernatant and cell homogenate for each type of transformed strain including the control exhibited pNP-β-Glc activity, and no considerable difference in activity was observed between them.

These results suggested that the introduction of the plasmid pYE-ASBGL2, pYE-AOBGL1p, or pYE-ASBGL1 into yeast strain EH13-15 does not allow expression of an activated protein having β-glucosidase activity. Moreover, the need for the deletion of an endogenous gene responsible for β-glucosidase activity in yeast was indicated.

Substitution of Secretory Signal Sequences

Twenty amino acids at the N-terminus of AOBGL2p or ASBGL2p are estimated to be a secretory signal sequence, and 19 amino acids at the N-terminus of AOBGL1p or ASBGL1p are estimated to be a secretory signal sequence. Note that the double-underlined parts shown in FIG. 5-1 correspond to estimated secretory signal sequences of AOBGL1, ASBGL1, AOBGL2, and ASBGL2.

Thus, for secretion and expression of ASBGL2, AOBGL1, or ASBGL1 in yeast, the estimated secretory signal sequence was substituted with a secretory signal sequence of a yeast secretory protein.

Initially, the following oligodeoxynucleotides were synthesized and annealed, and then inserted into the EcoRI site of the vector pYE22m, thus creating pYE-PacNhe.

```
PacI-NheI-F:       5'-AATTAATTAAGAGCTAGCG-3'
                                        (SEQ ID NO: 32)

(SEQ ID NO: 33)
PacI-NheI-R:       5'-TTAATTCTCGATCGCTTAA-3'
```

Using the plasmid pCR-ASBGL2 as a template, PCR was performed with the following primers Sac-ASBGL2-F and Sal-ASBGL2-R, using KOD-Plus (Toyobo). Approximately 2.6 kbp of a DNA fragment obtained by digesting the PCR-amplified DNA fragment with restriction enzymes SacI and SalI was inserted into the restriction sites of restriction enzymes SacI and SalI of the vector pYE-PacNhe, thus constructing a plasmid pYE-PN-ASBGL2.

```
Sac-ASBGL2-F:
                                        (SEQ ID NO: 34)
5'-AAGAGCTCGAGTCTCTGACATCAAGAGCCTCTACAGA-3'

Sal-ASBGL2-R:
                                        (SEQ ID NO: 35)
5'-
GGGTCGACCTATAAAGTAGAACATCCCTCCCCTACTACAC-3'
```

Using the plasmid pCR-AOBGL1 or pCR-ASBGL1 as a template, PCP was performed with the following primers Bgl2-AOBGL1-F and AOBGL1-2, using KOD-Plus (Toyobo). Approximately 2.5 kbp of a DNA fragment obtained by digesting the PCR-amplified DNA fragment with restriction enzymes BglII and SalI was inserted into the sites of restriction enzymes BamHI and SalI of the vector pYE-PacNhe, thus constructing a plasmid pYE-PN-AOBGL1 or pYE-PN-ASBGL1.

```
Bgl2-AOBGL1-F:
                                        (SEQ ID NO: 36)
5'-TAAGATCTAAGGATGATCTCGCGTACTCCCC-3'

AOBGL1-2:
                                        (SEQ ID NO: 31)
5'-GTCGACTTACTGGGCCTTAGGCAGCGA-3'
```

The primers shown below were designed to construct a plasmid for expression of a protein in which the estimated secretory signal sequence of ASBGL2p, AOBGL2p, AOBGL1p, or ASBGL1p (the sequence of positions 1 to 20 of SEQ ID NO: 3, the sequence of positions 1 to 20 of SEQ ID NO: 7, the sequence of positions 1 to 19 of SEQ ID NO: 11, or the sequence of positions 1 to 19 of SEQ ID NO: 15, respectively) was substituted with the secretory signal sequence MF(ALPHA)1 (YPL187W) (the sequence of positions 1 to 19 of the amino acid sequence shown in FIG. 1A), PHO5 (YBR093C) (the sequence of positions 1 to 17 of the amino acid sequence shown in FIG. 1B), or SUC2 (YIL162W) (the sequence of positions 1 to 19 of the amino acid sequence shown in FIG. 1C) of a yeast secretory protein.

The DNA sequence and the amino acid sequence of the secretory signal sequence MF(ALPHA)1 (YPL187W) are shown in SEQ ID NO: 43 and SEQ ID NO: 44, respectively. The DNA sequence and the amino acid sequence of the secretory signal sequence PHO5 (YBR093C) are shown in SEQ ID NO: 45 and SEQ ID NO: 46, respectively. The DNA sequence and the amino acid sequence of the secretory signal sequence SUC2 (YIL162W) are shown in SEQ ID NO: 47 and SEQ ID NO: 48, respectively.

```
ScPHO5-F:
                                        (SEQ ID NO: 37)
5'-TAAATGTTTAAATCTGTTGTTTATTCAATTTTAGCCGCTTCTTTGGC
CAATGCAG-3'

ScPHO5-R:
                                        (SEQ ID NO: 38)
5'-CTAGCTGCATTGGCCAAAGAAGCGGCTAAAATTGAATAAACAACAGA
TTTAAACATTTAAT-3'

ScSUC2-F:
                                        (SEQ ID NO: 39)
5'-TAAATGCTTTTGCAAGCTTTCCTTTTCCTTTTGGCTGGTTTTGCAGC
CAAAATATCTGCAG-3'

ScSUC2-R:
                                        (SEQ ID NO: 40)
5'-TAAATGAGATTTCCTTCAATTTTTACTGCAGTTTTATTCGCAGCATC
CTCCGCATTAGCTG-3'

ScMF1-F:
                                        (SEQ ID NO: 41)
5'-TAAATGAGATTTCCTTCAATTTTTACTGCAGTTTTATTCGCAGCATC
CTCCGCATTAGCTG-3'

ScMF1-R:
                                        (SEQ ID NO: 42)
5'-CTAGCAGCTAATGCGGAGGATGCTGCGAATAAAACTGCAGTAAAAAT
TGAAGGAAATCTCATTTAAT-3'
```

The combination of ScPHO5-F and ScPHO5-R, the combination of ScSUC2-F and ScSUC2-R, and the combination of ScMF1-F and ScMF1-R were each annealed, and then ligated to the plasmid pYE-PN-AOBGL1 or pYE-PN-ASBGL1 digested with restriction enzymes PacI and NheI, thus obtaining the following plasmids:

pYE-PHO5s-ASBGL2 (for expression of PHO5s-AOBGL2)
pYE-SUC2s-ASBGL2 (for expression of SUC2s-AOBGL2)
pYE-MF1s-ASBGL2 (for expression of MF1s-AOBGL2)
pYE-PHO5s-AOBGL1 (for expression of PHO5s-AOBGL1)
pYE-SUC2s-AOBGL1 (for expression of SUC2s-AOBGL1)
pYE-MF1s-AOBGL1 (for expression of MF1s-AOBGL1)
pYE-PHO5s-ASBGL1 (for expression of PHO5s-ASBGL1)
pYE-SUC2s-ASBGL1 (for expression of SUC2s-ASBGL1)
pYE-MF1s-ASBGL1 (for expression of MF1s-ASBGL1)

The DNA sequences of PHO5s-ASBGL2, SUC2s-ASBGL2, and MF1s-ASBGL2 are shown in SEQ ID NO: 17, SEQ ID NO: 18, and SEQ ID NO: 19. The DNA sequences of PHO5s-AOBGL1, SUC2s-AOBGL1, and MF1s-AOBGL1 are shown in SEQ ID NO: 20, SEQ ID NO: 21, and SEQ ID NO: 22, and the DNA sequences of PHO5s-ASBGL1, SUC2s-ASBGL1, and MF1s-ASBGL1 are shown in SEQ ID NO: 23, SEQ ID NO: 24, and SEQ ID NO: 25.

Creation of a Host Strain

A strain with deletion of the EXG1 (YLR300w) gene considered to be responsible for most of the extracellular β-glucosidase activity in yeast and its homolog EXG2 (YDR261c) gene was used as the host strain for transformation. This host strain was created as follows:

Each of Δexg1 strain (Δexg1: KanMX MATalpha his3Δ1 leu2Δ0 lys2Δ0 ura3Δ0; clone ID: 15210; Open Bio Systems) and Δexg2 strain (Δexg2: KanMX MATα his3Δ1 leu2Δ0 met15Δ0 ura3Δ0; clone ID: 3620; Open BioSystems) was applied to YPD agar medium, and cultured at 30° C. for 2 days. The cells of each strain were scraped with a platinum loop and mixed on SC-Met, Lys (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 1.5 g of phenylalanine, 11.25 g of serine, 0.9 g of tyrosine, 4.5 g of valine, 6 g of threonine, 1.2 g of tryptophan, and 0.6 g of uracil) agar medium (2% agar), and the mixture was cultured at 30° C. for 2 days. The grown strain was considered to be a hetero-diploid obtained by hybridization of the two strains. The obtained strain was applied to YPD agar medium and cultured at 30° C. for 2 days, and then the cells were scraped with a platinum loop, applied to 0.5% potassium acetate agar medium (2% agar), and cultured at room temperature for 5 days, thus forming spores. Tetrad dissection was performed to separate haploid strains. Genotypes of the obtained strains were confirmed by PCR, and Δexg1 Δexg2-1 strain (Δexg1: KanMX Δexg2: KanMX his3Δ1 leu2Δ0 lys2Δ0 ura3Δ0) was selected.

Using the genomic DNA of yeast strain 8288C, PCR was performed with the following primers TRP1-F and TRP1-R, using KOD-Plus (Toyobo). Approximately 2.7 kbp of the amplified DNA fragment was cloned using the Zero Blunt TOPO PCR cloning Kit (Life Technologies), thus obtaining a plasmid pCR-TRP1.

```
                                         (SEQ ID NO: 49)
TRP1-F:      TACTATTAGCTGAATTGCCACTGCTATCG (SEQ ID NO: 50)
TRP1-R:      TCTACAACCGCTAAATGTTTTGTTCG
```

2.7 kbp of a DNA fragment obtained by digesting pPRGINFRT3-103 (Japanese Patent Laid-Open No. 2001-120276) with restriction enzymes EcoRI and HindIII was blunt-ended using the Blunting Kit (Takara Bio), and then ligated to a DNA fragment obtained by digesting the plasmid pCR-TRP1 with restriction enzymes HpaI and StuI, using Ligation High (Toyobo), thus obtaining a plasmid pCR-Δtrp1:URA3-FRT. Using this plasmid as a template, PCR was performed with the primers TRP1-F and TRP1-R, using KOD-Plus (Toyobo). Then, 4.4 kbp of the resulting DNA fragment was used to transform Δexg1 Δexg2-1 strain in accordance with the lithium acetate method, and a strain that grew on SC-Ura (containing, per liter, 6.7 g of Yeast nitrogen base w/o amino acids (DIFCO), 20 g of glucose, and 1.3 g of amino acid powder (a mixture of 1.25 g of adenine sulfate, 0.5 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 1.2 g of tryptophan) agar medium (2% agar) was selected as the transformed strain. The transformed strain was cultured on YPGal medium (yeast extract: 2%, polypeptone: 1%, galactose: 2%) and then applied to SC+5-FOA (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan, and 0.6 g of uracil) agar medium (2% agar), and a grown strain was obtained as Δexg1 Δexg2-2 strain (Δexg1: KanMX Δexg2: KanMX Δtrp1 his3Δ1 leu2Δ0 lys2Δ0 ura3Δ0) and used as the host for the following transformation.

Δexg1 Δexg2-2 strain was transformed with the plasmid pYE-PHO5s-ASBGL2, pYE-SUC2s-ASBGL2, pYE-MF1s-ASBGL2, pYE-PHO5s-AOBGL1, pYE-SUC2s-AOBGL1, pYE-MF1s-AOBGL1, pYE-PHO5s-ASBGL1, or pYE-SUC2s-ASBGL1 in accordance with the lithium acetate method, and a strain that grew on SC-Trp agar medium was selected as the transformed strain.

Confirmation of X-β-Glc Activity

The obtained transformed strain was applied to SD-Trp agar medium containing 0.004% of X-β-Glc, and cultured at 30° C. for 3 days. As a result, the cells and surrounding regions were stained blue in the strain transformed with pYE-PHO5s-AOBGL1, pYE-SUC2s-AOBGL1, pYE-MF1s-AOBGL1, pYE-PHO5s-ASBGL1, pYE-SUC2s-ASBGL1, or pYE-MF1s-ASBGL1, suggesting that these strains had X-β-Glc hydrolyzing activity.

In the strain transfected with a control vector, the cells and surrounding regions were not stained blue, showing that the strain did not have X-β-Glc hydrolyzing activity.

Confirmation of pNP-β-Glc Activity

One platinum loop of the obtained transformed strain was inoculated to a liquid medium obtained by mixing 10 mL of SD-Trp liquid medium and 1 mL of 1 M potassium phosphate buffer, and cultured with shaking at 30° C. for 2 days. The culture was separated into the cells and culture supernatant by centrifugation.

Using Amicon Ultra 15 50 k (Merck), the culture supernatant was concentrated to approximately 500 μL by ultrafiltration, the buffer was replaced with 50 mM sodium phosphate buffer (pH 7.0) containing 0.1% CHAPS, and the resulting product was used as a crude enzyme solution. A mixture of 50 μL of the crude enzyme solution, 50 μL of 0.2 M sodium citrate buffer, 50 μL of a 20 mM aqueous solution of pNP-β Glc, and 50 μL of water was reacted at 37° C., and a change in absorbance at 405 nm was examined.

The results are shown in Table 5 below.

TABLE 5

| change in absorbance at 405 nm | |
|---|---|
| Plasmid | Δ405 nm |
| pYE-MF1s-ASBGL2 | 0.614 |
| pYE-PHO5s-ASBGL2 | 0.781 |
| pYE-SUC2s-ASBGL2 | 1.126 |
| pYE-ASBGL2 | 0.002 |
| pYE22m | 0.002 |
| pYE-MF1s-AOBGL1 | 0.508 |
| pYE-PHO5s-AOBGL1 | 0.37 |
| pYE-SUC2s-AOBGL1 | 0.369 |
| pYE22m | 0 |
| pYE-MF1s-ASBGL1 | 0.278 |
| pYE-PHO5s-ASBGL1 | 0.259 |
| pYE-SUC2s-ASBGL1 | 0.279 |
| pYE22m | 0.028 |

Preparation of Crude Enzyme Solutions

Each the pYE-SUC2s-ASBGL2-transfected strain, pYE-MF1s-AOBGL1-transfected strain, and control vector pYE22m-transfected strain was cultured with shaking at 30° C. for 3 days in SC-Trp liquid medium supplemented with 1/10 volume of 1M potassium phosphate buffer (pH 6.0). The resulting culture (200 ml) was centrifuged to obtain culture supernatant. The culture supernatant was saturated to 80% ammonium sulfate and centrifuged at 10,000×g. The supernatant was discarded, and the precipitate was dissolved in 15 mL of 50 mM sodium phosphate buffer (pH 7.0) containing 0.1% CHAPS. The solution was desalted and concentrated using Amicon Ultra-15 100 kDa, thus obtaining about 500 of a final sample.

Activity Against Mogroside V

50 μg/mL of mogroside V was adjusted to a total volume of 100 μL with 50 mM sodium citrate buffer (pH 5.0) and 20 μL of the above-described enzyme solution, and the mixture was reacted at 50° C. for 4 hours. The reaction mixture was passed through 500 mg of SepPakC18 (Waters) after washing with methanol and equilibration with water. The reaction product was rinsed with 40% methanol and then eluted with 80% methanol, and evaporated to dryness with SpeedVac. The resulting product was dissolved in 100 μL of water, and the solution was subjected to HPLC.

The conditions for HPLC were as follows:

Column: COSMOSIL $5C_{18}$-AR-II 4.6 mm I.D.×250 mm (Nacalai Tesque)

Mobile phase: A; acetonitrile, B; water

B conc. 90%→30% 60 min linear gradient

Flow rate: 1 ml/min

Temperature: 40° C.

Detection: UV 203 nm

As a result, strong activities to completely hydrolyze mogroside V to mogroside IIIE (hydrolyze β-1,6-glucoside bonds) were detected in ASBGL2 and AOBGL1 (FIGS. 2A and 2B), whereas the control yielded no new product from mogroside V (FIG. 2B).

Activity Against Mogroside IIIE

The AOBGL1 enzyme solution was reacted with mogroside IIIE under the same conditions as described above, for a reaction time of 15 hours. As a result, an activity to hydrolyze mogroside IIIE to a mogrol diglycoside and a mogrol monoglycoside was also detected in AOBGL1 (FIGS. 3A and 4A), whereas the control yielded no new products from mogroside IIIE (FIGS. 3B and 4B).

Sequence Listing Free Text

[SEQ ID NO: 1] cDNA sequence of ASBGL2
[SEQ ID NO: 2] genomic DNA sequence of ASBGL2
[SEQ ID NO: 3] amino acid sequence of ASBGL2
[SEQ ID NO: 4] amino acid sequence of ASBGL2 mature protein
[SEQ ID NO: 5] cDNA sequence of AOBGL2
[SEQ ID NO: 6] genomic DNA sequence of AOBGL2
[SEQ ID NO: 7] amino acid sequence of AOBGL2
[SEQ ID NO: 8] amino acid sequence of AOBGL2 mature protein
[SEQ ID NO: 9] cDNA sequence of AOBGL1
[SEQ ID NO: 10] genomic DNA sequence of AOBGL1
[SEQ ID NO: 11] amino acid sequence of AOBGL1
[SEQ ID NO: 12] amino acid sequence of AOBGL1 mature protein.
[SEQ ID NO: 13] cDNA sequence of ASBGL1
[SEQ ID NO: 14] genomic DNA sequence of ASBGL1
[SEQ ID NO: 15] amino acid sequence of ASBGL1
[SEQ ID NO: 16] amino acid sequence of ASBGL1 mature protein
[SEQ ID NO: 17] DNA sequence of PHO5s-ASBGL2
[SEQ ID NO: 18] DNA sequence of SUC2s-ASBGL2
[SEQ ID NO: 19] DNA sequence of MF1s-ASBGL2
[SEQ ID NO: 20] DNA sequence of PHO5s-AOBGL1
[SEQ ID NO: 21] DNA sequence of SUC2s-AOBGL1
[SEQ ID NO: 22] DNA sequence of MF1s-AOBGL1
[SEQ ID NO: 23] DNA sequence of PHO5s-ASBGL1
[SEQ ID NO: 24] DNA sequence of SUC2s-ASBGL1
[SEQ ID NO: 25] DNA sequence of MF1s-ASBGL1
[SEQ ID NO: 26] primer (AOBGL2-1) used in the Examples
[SEQ ID NO: 27] primer (AOBGL2-2) used in the Examples
[SEQ ID NO: 28] primer (ASBGL2-1) used in the Examples
[SEQ ID NO: 29] primer (ASBGL2-2) used in the Examples
[SEQ ID NO: 30] primer (AOBGL1-1) used in the Examples
[SEQ ID NO: 31] primer (AOBGL1-2) used in the Examples
[SEQ ID NO: 32] oligodeoxynucleotide (PacI-NheI-F) used in the Examples
[SEQ ID NO: 33] oligodeoxynucleotide (PacI-NheI-R) used in the Examples
[SEQ ID NO: 34] oligodeoxynucleotide (Sac-ASBGL2-F) used in the Examples
[SEQ ID NO: 35] oligodeoxynucleotide (Sal-ASBGL2-R) used in the Examples
[SEQ ID NO: 36] primer (Bgl2-AOBGL1-F) used in the Examples
[SEQ ID NO: 37] primer (ScPHO5-F) used in the Examples
[SEQ ID NO: 38] primer (ScPHO5-R) used in the Examples
[SEQ ID NO: 39] primer (ScSUC2-F) used in the Examples
[SEQ ID NO: 40] primer (ScSUC2-R) used in the Examples
[SEQ ID NO: 41] primer (ScMF1-F) used in the Examples
[SEQ U) NO: 42] primer (ScMF1-R) used in the Examples
[SEQ ID NO: 43] DNA sequence of the secretory signal sequence MF(ALPHA)1 (YPL187W)
[SEQ ID NO: 44] amino acid sequence of the secretory signal sequence MF(ALPHA)1 (YPL187W)
[SEQ ID NO: 45] DNA sequence of the secretory signal sequence PHO5 (YBR093C)
[SEQ ID NO: 46] amino acid sequence of the secretory signal sequence PHO5 (YBR093C)
[SEQ ID NO: 47] DNA sequence of the secretory signal sequence SUC2 (YIL162W)
[SEQ ID NO: 48] amino acid sequence of the secretory signal sequence SUC2 (YIL162W)
[SEQ ID NO: 49] primer (TRP1-F) used in the Examples
[SEQ ID NO: 50] primer (TRP1-R) used in the Examples

The invention claimed is:

1. A method for preparing a mogroside having no β-1,6-glucoside bond comprising reacting a protein selected from the group consisting of proteins (a) to (c) shown below with a mogroside having at least one β-1,6-glucoside bond, thereby cleaving said β-1,6-glucoside bond:
   (a) a protein having an amino acid sequence selected from the group consisting of SEQ ID NO: 4 and SEQ ID NO: 8;
   (b) a protein having an amino acid sequence selected from the group consisting of SEQ ID NO: 4 and SEQ ID NO: 8, wherein 1 to 42 amino acids have been deleted, substituted, inserted, and/or added, and having an activity to cleave a β-1,6-glucoside bond of a mogroside; and
   (c) a protein having an amino acid sequence having 95% or more sequence identity to an amino acid sequence selected from the group consisting of SEQ ID NO: 4 and SEQ ID NO: 8, and having an activity to cleave a β-1,6-glucoside bond of a mogroside.

2. The method according to claim 1, wherein the protein selected from the group consisting of proteins (a) to (c) further includes a secretory signal peptide.

3. The method according to claim 1, wherein the mogroside having at least one β-1,6-glucoside bond further has at least one β-1,2-glucoside bond.

4. The method according to claim 3, wherein the mogroside having at least one β-1,6-glucoside bond and at least one β-1,2-glucoside bond is selected from mogroside V, siamenoside I, mogroside IV, and mogroside IIIA$_1$.

5. The method according to claim 1, wherein the mogroside having no β-1,6-glucoside bond is selected from mogroside IIIE and mogroside IIA.

6. A method for producing a mogroside having no β-1,6-glucoside bond comprising culturing a non-human transformant obtained by introducing a polynucleotide selected from the group consisting of polynucleotides (a) to (d) shown below into a host producing a mogroside having at least one β-1,6-glucoside bond:
   (a) a polynucleotide having a nucleotide sequence selected from the group consisting of positions 61 to 2601 of SEQ ID NO: 1, positions 61 to 2707 of SEQ ID NO: 2, positions 61 to 2601 of SEQ ID NO: 5 and positions 61 to 2708 of SEQ ID NO: 6;
   (b) a polynucleotide encoding a protein having an amino acid sequence selected from the group consisting of SEQ ID NO: 4 and SEQ ID NO: 8;
   (c) a polynucleotide encoding a protein having an amino acid sequence selected from the group consisting of SEQ ID NO: 4 and SEQ ID NO: 8, wherein 1 to 42 amino acids have been deleted, substituted, inserted, and/or added, and having an activity to cleave a β-1,6-glucoside bond of a mogroside; and
   (d) a polynucleotide encoding a protein having an amino acid sequence having 95% or more sequence identity to an amino acid sequence selected from the group consisting of SEQ ID NO: 4 and SEQ ID NO: 8, and having an activity to cleave a β-1,6-glucoside bond of a mogroside.

7. The method according to claim 6, wherein the polynucleotide selected from the group consisting of polynucleotides (a) to (d) further includes a polynucleotide consisting of a nucleotide sequence encoding a secretory signal peptide.

8. The method according to claim 7, wherein the polynucleotide consisting of a nucleotide sequence encoding a secretory signal peptide is a polynucleotide consisting of a nucleotide sequence set forth in any of positions 1 to 60 of SEQ ID NO: 1, positions 1 to 60 of SEQ ID NO: 5, positions 1 to 57 of SEQ ID NO: 9, positions 1 to 57 of SEQ ID NO: 13, SEQ ID NO: 43, SEQ ID NO: 45, and SEQ ID NO: 47.

9. The method according to claim 8, wherein the polynucleotide containing the polynucleotide consisting of a nucleotide sequence encoding a secretory signal peptide consists of a nucleotide sequence set forth in any of SEQ ID NO: 1, SEQ ID NO: 2, SEQ ID NO: 5, SEQ ID NO: 6, and SEQ ID NOS: 17 to 19.

10. The method according to claim 6, wherein the polynucleotide is inserted into an expression vector.

11. The method according to claim 6, wherein the transformant is transformed yeast or a transformed plant.

12. A method for preparing a mogroside having no β-1,6-glucoside bond comprising contacting an enzyme agent derived from a non-human transformed cell obtained by introducing, into a host cell, a polynucleotide selected from the group consisting of polynucleotides (a) to (d) shown below, with a mogroside having at least one β-1,6-glucoside bond, thereby cleaving said β-1,6-glucoside bond:
 (a) a polynucleotide having a nucleotide sequence selected from the group consisting of positions 61 to 2601 of SEQ ID NO: 1, positions 61 to 2707 of SEQ ID NO: 2, positions 61 to 2601 of SEQ ID NO: 5, and positions 61 to 2708 of SEQ ID NO: 6;
 (b) a polynucleotide encoding a protein having an amino acid sequence selected from the group consisting of SEQ ID NO: 4 and SEQ ID NO: 8;
 (c) a polynucleotide encoding a protein having an amino acid sequence selected from the group consisting of SEQ ID NO: 4 and SEQ ID NO: 8, wherein 1 to 42 amino acids have been deleted, substituted, inserted, and/or added, and having an activity to cleave a β-1,6-glucoside bond of a mogroside; and
 (d) a polynucleotide encoding a protein having an amino acid sequence having 95% or more sequence identity to an amino acid sequence selected from the group consisting of SEQ ID NO: 4 and SEQ ID NO: 8, and having an activity to cleave a β-1,6-glucoside bond of a mogroside.

13. The method according to claim 12, wherein the polynucleotide selected from the group consisting of polynucleotides (a) to (d) further includes a polynucleotide consisting of a nucleotide sequence encoding a secretory signal peptide.

14. The method according to claim 13, wherein the polynucleotide consisting of a nucleotide sequence encoding a secretory signal peptide is a polynucleotide consisting of a nucleotide sequence set forth in any of positions 1 to 60 of SEQ ID NO: 1, positions 1 to 60 of SEQ ID NO: 5, positions 1 to 57 of SEQ ID NO: 9, positions 1 to 57 of SEQ ID NO: 13, SEQ ID NO: 43, SEQ ID NO: 45, and SEQ ID NO: 47.

15. The method according to claim 14, wherein the polynucleotide containing the polynucleotide consisting of a nucleotide sequence encoding a secretory signal peptide consists of a nucleotide sequence set forth in any of SEQ ID NO: 1, SEQ ID NO: 2, SEQ ID NO: 5, SEQ ID NO: 6, and SEQ ID NOS: 17 to 19.

16. The method according to claim 12, wherein the polynucleotide is inserted into an expression vector.

17. The method according to claim 12, wherein the transformed cell is a transformed bacterium or transformed yeast.

18. The method according claim 12, wherein the mogroside having at least one β-1,6-glucoside bond further has at least one β-1,2-glucoside bond.

19. The method according to claim 18, wherein the mogroside having at least one β-1,6-glucoside bond and at least one β-1,2-glucoside bond is selected from mogroside V, siamenoside I, mogroside IV, and mogroside IIIA$_1$.

20. The method according to claim 12, wherein the mogroside having no β-1,6-glucoside bond is selected from mogroside IIIE and mogroside IIA.

21. The method according to claim 1, wherein the protein (b) is selected from the group consisting of SEQ ID NO: 4 and SEQ ID NO: 8, wherein 1 to 14 amino acids have been deleted, substituted, inserted, and/or added, and having an activity to cleave a β-1,6-glucoside bond of a mogroside.

* * * * *

SEQUENCE LISTING

```
<160> NUMBER OF SEQ ID NOS: 50

<210> SEQ ID NO 1
<211> LENGTH: 2601
<212> TYPE: DNA
<213> ORGANISM: Aspergillus sojae

<400> SEQUENCE: 1
atggctgcct ttccggccta cttggctctt ttgtcttact tggtcccggg ggctctgtcc    60
```

```
cacccctgagg cggagtctct gacatcaaga gcctctacag aagcttactc ccctccatat      120
tacccagctc cgaacggagg atggatatcc gaatgggcca gtgcctatga gaaggcacac      180
cgtgtcgtaa gtaacatgac cttggccgag aaggtgaatc tcacaagtgg caccggtatc      240
tacatgggac cttgtgccgg ccagactggc agtgttcccc gttttgggat ccccaacctg      300
tgccttcatg attctcctct cggagtccgt aattcggatc ataatacggc attcccggcc      360
ggcatcacgg tcggggccac atttgacaag gacctgatgt acgagcgcgg agtcggtctg      420
ggcgaagagg cgcggggaaa gggtatcaac gttcttttag gccgtccgt gggccctatt       480 gggcggaagc cacggggagg ccgcaattgg gagggtttcg gagcggatcc cagtttacag      540 gccttttgggg gctcgttgac cattaaagga atgcaaagta cgggtgctat tgcttcgctc     600
aagcatctta tcggaaacga acaggagcag catcggatga gcagtgttat cactcaaggc     660
tattcgtcaa atatcgatga caggactttg catgagctgt atctgtggcc attcgcggaa     720
agtgtaagag ccggtgctgg ttcggtcatg attgcgtata cgatgtgaa caggtccgcc      780 tgcagccaga atagtaagct catcaatgga atcctcaagg acgagctggg gtttcagggc     840
tttgtcgtga ccgactggtt ggctcatatt ggcggagttt cgtcagcgtt ggctggcctg     900
gacatgagca tgccgggtga cggagctatc ccactcttgg gcacgagtta ctgggcgtgg    960
gagctgtcgc gctccgtgct caatggctcg gtcccggtcg agcgtctcaa tgacatggtc    1020
acgcgaatcg tcgcaacatg gtacaaaatg gggcaggaca aagactatcc gctaccaaac    1080
ttctcctcaa acaccgagga tgagactggg ccgttgtatc ctggcgcctt attttcccca    1140
agtggcattg tcaaccaata cgtcaatgtc caaggcaacc ataatgtcac ggcccgggca    1200
atcgctagag atgcaatcac gttgctaaag aataacgaca atgtcctgcc tctgaaacgg    1260
aatgccagct tgaagatctt tggcactgat gccggggcca attcggacgg gatcaactct    1320
tgcactgaca aaggctgcaa caaaggcgta ttgaccatgg gctggggaag cggaacatcc    1380
agactcccat atctcattac gccgcaagaa gcgatagcga atatctcatc caatgccgaa    1440
ttccacatca cggacacgtt tcctttgggc gtcaccgcag gcctcgacga cattgcgatc    1500
gtcttcatca attcggactc cggcgagaac tacatcaccg tcgatggcaa tcctggagac    1560
cgtacgctgg cagggctgac cgcatggcac aacggcgaca accttgtcaa agctgctgca    1620
gaaaagttct caaacgtagt ggttgtagtg cacaccgtgg gacccatcct gatgaagaa     1680 tggatcgacc tcgactccgt caaagcggtg ctcgtcgctc acttacccgg acaggaggca    1740
ggctggtcac taaccgacat cctctttggg gactatagtc ctagcggcca tctgccttac    1800
acaatccctc gcagtgaatc agactaccca gagagcgtcg gattgattgc tcagccattc    1860
ggccaaatcc aagacgacta taccgaaggc ctctacatcg attaccgcca cttcctaaaa    1920
gcaaacatca ccccccgata cccattcgga cacggtctct cctacaccac gttcaacttc    1980
accgaaccca acctctccat catcaaaccc ctagacacag cctacccgc cgcgcgaccc    2040 cctaaaggct ccacacccac atacccccacc accaaacccg ccgcatcaga agtcgcctgg  2100
cccaagaact tcaaccgcat ctggcgctac ctctacccct acctcgacaa cccggaaggc    2160
gcagccgcca actcctcaaa gacatacccct tacccagacg gctacaccac agagcccaag    2220
cccgcccctc gcgccggcgg agcagaagga ggcaacccgg ccttatggga cgtggccttt    2280
tcggtgcagg tcaaagtgac gaacacgggt tctcgggatg gtcgtgccgt tgcacagctc   2340
tatgtggaat tgcccagtag cctggggctg gatacgccgt ctcgacagct gcggcagttt   2400
gagaagacga agatcttggc tgcggggag agtgaggtcc ttacgttgga tgtcacgcgc   2460
```

-continued

```
aaggatctta gtgcttggga tgttgttgtt caggactgga aggcgcctgt gaatggggag    2520
ggagttaaga tctgggttgg agaaagtgtt gcggatttga gggttgggtg tgtagtaggg    2580
gagggatgtt ctactttata g                                              2601
```

<210> SEQ ID NO 2
<211> LENGTH: 2707
<212> TYPE: DNA
<213> ORGANISM: Aspergillus sojae

<400> SEQUENCE: 2

```
atggctgcct ttccggccta cttggctctt ttgtcttact tggtcccggg ggctctgtcc      60
caccctgagg cggagtctct gacatcaaga gcctctacag aagcttactc ccctccatat     120
tacccagctc cgaacggagg atggatatcc gaatgggcca gtgcctatga aaggcacac     180 cgtgtcgtaa gtaacatgac cttggccgag aaggtgaatc tcacaagtgg caccggtatc     240
tacatgggac cttgtgccgg ccagactggc agtgttcccc gttttgggat ccccaacctg     300
tgccttcatg attctcctct cggagtccgt aattcggatc ataatacggc attcccggcc     360
ggcatcacgg tcggggccac atttgacaag gacctgatgt acgagcgcgg agtcggtctg     420
ggcgaagagg cgcggggaaa gggtatcaac gttcttttag gccgtccgt gggccctatt      480 gggcggaagc cacggggagg ccgcaattgg gagggtttcg gagcggatcc cagtttacag     540 gccttttgggg gctcgttgac cattaaagga atgcaaagta cgggtgctat tgcttcgctc    600
aagcatctta tcggaaacga acaggagcag catcggatga gcagtgttat cactcaaggc    660
tattcgtcaa atatcgatga caggactttg catgagctgt atctgtggcc attcgcggaa    720
agtgtaagag ccggtgctgg ttcggtcatg attgcgtata cgatgtaag ccaatctctg     780 caccttcacc tcggacggga tgactaagta gagtgtaggt gaacaggtcc gcctgcagcc    840
agaatagtaa gctcatcaat ggaatcctca aggacgagct gggggtttcag ggctttgtcg   900 tgaccgactg gttggctcat attggcggag tttcgtcagc gttggctggc ctggacatga    960
gcatgccggg tgacggagct atcccactct tgggcacgag ttactgggcg tgggagctgt   1020
cgcgctccgt gctcaatggc tcggtcccgg tcgagcgtct caatgacatg gtgggcactc   1080
caacgctacc agttttgtct taggctaata caaataatta caggtcacgc gaatcgtcgc   1140
aacatggtac aaaatggggc aggacaaaga ctatccgcta ccaaacttct cctcaaacac   1200
cgaggatgag actgggccgt tgtatcctgg cgccttattt tccccaagtg gcattgtcaa   1260
ccaatacgtc aatgtccaag caaccataa tgtcacggcc cgggcaatcg ctagagatgc    1320
aatcacgttg ctaaagaata acgacaatgt cctgcctctg aaacggaatg ccagcttgaa   1380
gatctttggc actgatgccg gggccaattc ggacgggatc aactcttgca ctgacaaagg   1440
ctgcaacaaa ggcgtattga ccatgggctg gggaagcgga acatccagac tcccatatct   1500
cattacgccg caagaagcga tagcgaatat ctcatccaat gccgaattcc acatcacgga   1560
cacgtttcct ttgggcgtca ccgcaggcct cgacgacatt gcgatcgtct tcatcaattc   1620
ggactccggc gagaactaca tcaccgtcga tggcaatcct ggagaccgta cgctggcagg   1680
gctgaccgca tggcacaacg cgacaaacct tgtcaaagct gctgcagaaa agttctcaaa   1740
cgtagtggtt gtagtgcaca ccgtgggacc catcctgatg aagaatgga tcgacctcga    1800 ctccgtcaaa gcggtgctcg tcgctcactt acccggacag gaggcaggct ggtcactaac   1860
cgacatcctc tttggggact atagtcctag cggccatctg ccttacacaa tccctcgcag   1920
```

```
tgaatcagac tacccagaga gcgtcggatt gattgctcag ccattcggcc aaatccaaga   1980
cgactatacc gaaggcctct acatcgatta ccgccacttc ctaaaagcaa acatcacccc   2040
ccgataccca ttcggacacg gtctctccta caccacgttc aacttcaccg aacccaacct   2100
ctccatcatc aaaccctag acacagcta ccccgccgcg cgaccccta aaggctccac     2160 acccacatac cccaccacca aacccgccgc atcagaagtc gcctggccca agaacttcaa   2220
ccgcatctgg cgctacctct acccctacct cgacaacccg gaaggcgcag ccgccaactc   2280
ctcaaagaca taccctttacc cagacggcta caccacagag cccaagcccg ccctcgcgc   2340 cggcggagca gaaggaggca acccggcctt atgggacgtg gcctttcgg tgcaggtcaa    2400 agtgacgaac acgggttctc gggatggtcg tgccgttgca cagctctatg tggaattgcc   2460
cagtagcctg gggctggata cgccgtctcg acagctgcgg cagtttgaga agacgaagat   2520
cttggctgcg ggggagagtg aggtccttac gttggatgtc acgcgcaagg atcttagtgc   2580
ttgggatgtt gttgttcagg actggaaggc gcctgtgaat ggggagggag ttaagatctg   2640
ggttggagaa agtgttgcgg atttgagggt tgggtgtgta gtaggggagg gatgttctac   2700
tttatag                                                            2707
```

<210> SEQ ID NO 3
<211> LENGTH: 866
<212> TYPE: PRT
<213> ORGANISM: Aspergillus sojae

<400> SEQUENCE: 3

```
Met Ala Ala Phe Pro Ala Tyr Leu Ala Leu Leu Ser Tyr Leu Val Pro
1               5                   10                  15

Gly Ala Leu Ser His Pro Glu Ala Glu Ser Leu Thr Ser Arg Ala Ser
            20                  25                  30

Thr Glu Ala Tyr Ser Pro Pro Tyr Tyr Pro Ala Pro Asn Gly Gly Trp
        35                  40                  45

Ile Ser Glu Trp Ala Ser Ala Tyr Glu Lys Ala His Arg Val Val Ser
    50                  55                  60

Asn Met Thr Leu Ala Glu Lys Val Asn Leu Thr Ser Gly Thr Gly Ile
65                  70                  75                  80

Tyr Met Gly Pro Cys Ala Gly Gln Thr Gly Ser Val Pro Arg Phe Gly
                85                  90                  95

Ile Pro Asn Leu Cys Leu His Asp Ser Pro Leu Gly Val Arg Asn Ser
            100                 105                 110

Asp His Asn Thr Ala Phe Pro Ala Gly Ile Thr Val Gly Ala Thr Phe
        115                 120                 125

Asp Lys Asp Leu Met Tyr Glu Arg Gly Val Gly Leu Gly Glu Glu Ala
    130                 135                 140

Arg Gly Lys Gly Ile Asn Val Leu Leu Gly Pro Ser Val Gly Pro Ile
145                 150                 155                 160

Gly Arg Lys Pro Arg Gly Gly Arg Asn Trp Glu Gly Phe Gly Ala Asp
                165                 170                 175

Pro Ser Leu Gln Ala Phe Gly Gly Ser Leu Thr Ile Lys Gly Met Gln
            180                 185                 190

Ser Thr Gly Ala Ile Ala Ser Leu Lys His Leu Ile Gly Asn Glu Gln
        195                 200                 205

Glu Gln His Arg Met Ser Ser Val Ile Thr Gln Gly Tyr Ser Ser Asn
    210                 215                 220

Ile Asp Asp Arg Thr Leu His Glu Leu Tyr Leu Trp Pro Phe Ala Glu
```

```
            225                 230                 235                 240
        Ser Val Arg Ala Gly Ala Gly Ser Val Met Ile Ala Tyr Asn Asp Val
                        245                 250                 255

Asn Arg Ser Ala Cys Ser Gln Asn Ser Lys Leu Ile Asn Gly Ile Leu
                        260                 265                 270

Lys Asp Glu Leu Gly Phe Gln Gly Phe Val Val Thr Asp Trp Leu Ala
                        275                 280                 285

His Ile Gly Gly Val Ser Ser Ala Leu Ala Gly Leu Asp Met Ser Met
                        290                 295                 300

Pro Gly Asp Gly Ala Ile Pro Leu Leu Gly Thr Ser Tyr Trp Ala Trp
        305                 310                 315                 320

Glu Leu Ser Arg Ser Val Leu Asn Gly Ser Val Pro Val Glu Arg Leu
                        325                 330                 335

Asn Asp Met Val Thr Arg Ile Val Ala Thr Trp Tyr Lys Met Gly Gln
                        340                 345                 350

Asp Lys Asp Tyr Pro Leu Pro Asn Phe Ser Ser Asn Thr Glu Asp Glu
                        355                 360                 365

Thr Gly Pro Leu Tyr Pro Gly Ala Leu Phe Ser Pro Ser Gly Ile Val
                        370                 375                 380

Asn Gln Tyr Val Asn Val Gln Gly Asn His Asn Val Thr Ala Arg Ala
        385                 390                 395                 400

Ile Ala Arg Asp Ala Ile Thr Leu Leu Lys Asn Asn Asp Asn Val Leu
                        405                 410                 415

Pro Leu Lys Arg Asn Ala Ser Leu Lys Ile Phe Gly Thr Asp Ala Gly
                        420                 425                 430

Ala Asn Ser Asp Gly Ile Asn Ser Cys Thr Asp Lys Gly Cys Asn Lys
                        435                 440                 445

Gly Val Leu Thr Met Gly Trp Gly Ser Gly Thr Ser Arg Leu Pro Tyr
                        450                 455                 460

Leu Ile Thr Pro Gln Glu Ala Ile Ala Asn Ile Ser Ser Asn Ala Glu
        465                 470                 475                 480

Phe His Ile Thr Asp Thr Phe Pro Leu Gly Val Thr Ala Gly Leu Asp
                        485                 490                 495

Asp Ile Ala Ile Val Phe Ile Asn Ser Asp Ser Gly Glu Asn Tyr Ile
                        500                 505                 510

Thr Val Asp Gly Asn Pro Gly Asp Arg Thr Leu Ala Gly Leu Thr Ala
                        515                 520                 525

Trp His Asn Gly Asp Asn Leu Val Lys Ala Ala Glu Lys Phe Ser
                        530                 535                 540

Asn Val Val Val Val His Thr Val Gly Pro Ile Leu Met Glu Glu
        545                 550                 555                 560

Trp Ile Asp Leu Asp Ser Val Lys Ala Val Leu Val Ala His Leu Pro
                        565                 570                 575

Gly Gln Glu Ala Gly Trp Ser Leu Thr Asp Ile Leu Phe Gly Asp Tyr
                        580                 585                 590

Ser Pro Ser Gly His Leu Pro Tyr Thr Ile Pro Arg Ser Glu Ser Asp
                        595                 600                 605

Tyr Pro Glu Ser Val Gly Leu Ile Ala Gln Pro Phe Gly Gln Ile Gln
                        610                 615                 620

Asp Asp Tyr Thr Glu Gly Leu Tyr Ile Asp Tyr Arg His Phe Leu Lys
        625                 630                 635                 640

Ala Asn Ile Thr Pro Arg Tyr Pro Phe Gly His Gly Leu Ser Tyr Thr
                        645                 650                 655
```

```
Thr Phe Asn Phe Thr Glu Pro Asn Leu Ser Ile Ile Lys Pro Leu Asp
            660                 665                 670

Thr Ala Tyr Pro Ala Ala Arg Pro Lys Gly Ser Thr Pro Thr Tyr
        675                 680                 685

Pro Thr Thr Lys Pro Ala Ala Ser Glu Val Ala Trp Pro Lys Asn Phe
    690                 695                 700

Asn Arg Ile Trp Arg Tyr Leu Tyr Pro Tyr Leu Asp Asn Pro Glu Gly
705                 710                 715                 720

Ala Ala Ala Asn Ser Ser Lys Thr Tyr Pro Tyr Pro Asp Gly Tyr Thr
                725                 730                 735

Thr Glu Pro Lys Pro Ala Pro Arg Ala Gly Gly Ala Glu Gly Gly Asn
            740                 745                 750

Pro Ala Leu Trp Asp Val Ala Phe Ser Val Gln Val Lys Val Thr Asn
        755                 760                 765

Thr Gly Ser Arg Asp Gly Arg Ala Val Ala Gln Leu Tyr Val Glu Leu
    770                 775                 780

Pro Ser Ser Leu Gly Leu Asp Thr Pro Ser Arg Gln Leu Arg Gln Phe
785                 790                 795                 800

Glu Lys Thr Lys Ile Leu Ala Ala Gly Glu Ser Glu Val Leu Thr Leu
                805                 810                 815

Asp Val Thr Arg Lys Asp Leu Ser Ala Trp Asp Val Val Gln Asp
            820                 825                 830

Trp Lys Ala Pro Val Asn Gly Glu Gly Val Lys Ile Trp Val Gly Glu
        835                 840                 845

Ser Val Ala Asp Leu Arg Val Gly Cys Val Val Gly Glu Gly Cys Ser
    850                 855                 860

Thr Leu
865

<210> SEQ ID NO 4
<211> LENGTH: 846
<212> TYPE: PRT
<213> ORGANISM: Aspergillus sojae

<400> SEQUENCE: 4

His Pro Glu Ala Glu Ser Leu Thr Ser Arg Ala Ser Thr Glu Ala Tyr
1               5                   10                  15

Ser Pro Pro Tyr Tyr Pro Ala Pro Asn Gly Gly Trp Ile Ser Glu Trp
            20                  25                  30

Ala Ser Ala Tyr Glu Lys Ala His Arg Val Val Ser Asn Met Thr Leu
        35                  40                  45

Ala Glu Lys Val Asn Leu Thr Ser Gly Thr Gly Ile Tyr Met Gly Pro
    50                  55                  60

Cys Ala Gly Gln Thr Gly Ser Val Pro Arg Phe Gly Ile Pro Asn Leu
65                  70                  75                  80

Cys Leu His Asp Ser Pro Leu Gly Val Arg Asn Ser Asp His Asn Thr
                85                  90                  95

Ala Phe Pro Ala Gly Ile Thr Val Gly Ala Thr Phe Asp Lys Asp Leu
            100                 105                 110

Met Tyr Glu Arg Gly Val Gly Leu Gly Glu Glu Ala Arg Gly Lys Gly
        115                 120                 125

Ile Asn Val Leu Leu Gly Pro Ser Val Gly Pro Ile Gly Arg Lys Pro
    130                 135                 140

Arg Gly Gly Arg Asn Trp Glu Gly Phe Gly Ala Asp Pro Ser Leu Gln
```

-continued

```
            145                 150                 155                 160
Ala Phe Gly Gly Ser Leu Thr Ile Lys Gly Met Gln Ser Thr Gly Ala
                165                 170                 175

Ile Ala Ser Leu Lys His Leu Ile Gly Asn Glu Gln Glu Gln His Arg
                180                 185                 190

Met Ser Ser Val Ile Thr Gln Gly Tyr Ser Ser Asn Ile Asp Asp Arg
                195                 200                 205

Thr Leu His Glu Leu Tyr Leu Trp Pro Phe Ala Glu Ser Val Arg Ala
    210                 215                 220

Gly Ala Gly Ser Val Met Ile Ala Tyr Asn Asp Val Asn Arg Ser Ala
225                 230                 235                 240

Cys Ser Gln Asn Ser Lys Leu Ile Asn Gly Ile Leu Lys Asp Glu Leu
                245                 250                 255

Gly Phe Gln Gly Phe Val Val Thr Asp Trp Leu Ala His Ile Gly Gly
                260                 265                 270

Val Ser Ser Ala Leu Ala Gly Leu Asp Met Ser Met Pro Gly Asp Gly
                275                 280                 285

Ala Ile Pro Leu Leu Gly Thr Ser Tyr Trp Ala Trp Glu Leu Ser Arg
    290                 295                 300

Ser Val Leu Asn Gly Ser Val Pro Val Glu Arg Leu Asn Asp Met Val
305                 310                 315                 320

Thr Arg Ile Val Ala Thr Trp Tyr Lys Met Gly Gln Asp Lys Asp Tyr
                325                 330                 335

Pro Leu Pro Asn Phe Ser Ser Asn Thr Glu Asp Glu Thr Gly Pro Leu
                340                 345                 350

Tyr Pro Gly Ala Leu Phe Ser Pro Ser Gly Ile Val Asn Gln Tyr Val
                355                 360                 365

Asn Val Gln Gly Asn His Asn Val Thr Ala Arg Ala Ile Ala Arg Asp
                370                 375                 380

Ala Ile Thr Leu Leu Lys Asn Asn Asp Asn Val Leu Pro Leu Lys Arg
385                 390                 395                 400

Asn Ala Ser Leu Lys Ile Phe Gly Thr Asp Ala Gly Ala Asn Ser Asp
                405                 410                 415

Gly Ile Asn Ser Cys Thr Asp Lys Gly Cys Asn Lys Gly Val Leu Thr
                420                 425                 430

Met Gly Trp Gly Ser Gly Thr Ser Arg Leu Pro Tyr Leu Ile Thr Pro
                435                 440                 445

Gln Glu Ala Ile Ala Asn Ile Ser Ser Asn Ala Glu Phe His Ile Thr
    450                 455                 460

Asp Thr Phe Pro Leu Gly Val Thr Ala Gly Leu Asp Asp Ile Ala Ile
465                 470                 475                 480

Val Phe Ile Asn Ser Asp Ser Gly Glu Asn Tyr Ile Thr Val Asp Gly
                485                 490                 495

Asn Pro Gly Asp Arg Thr Leu Ala Gly Leu Thr Ala Trp His Asn Gly
                500                 505                 510

Asp Asn Leu Val Lys Ala Ala Ala Glu Lys Phe Ser Asn Val Val Val
    515                 520                 525

Val Val His Thr Val Gly Pro Ile Leu Met Glu Glu Trp Ile Asp Leu
530                 535                 540

Asp Ser Val Lys Ala Val Leu Val Ala His Leu Pro Gly Gln Glu Ala
545                 550                 555                 560

Gly Trp Ser Leu Thr Asp Ile Leu Phe Gly Asp Tyr Ser Pro Ser Gly
                565                 570                 575
```

His Leu Pro Tyr Thr Ile Pro Arg Ser Glu Ser Asp Tyr Pro Glu Ser
                580                 585                 590
Val Gly Leu Ile Ala Gln Pro Phe Gly Gln Ile Gln Asp Asp Tyr Thr
            595                 600                 605
Glu Gly Leu Tyr Ile Asp Tyr Arg His Phe Leu Lys Ala Asn Ile Thr
        610                 615                 620
Pro Arg Tyr Pro Phe Gly His Gly Leu Ser Tyr Thr Thr Phe Asn Phe
625                 630                 635                 640
Thr Glu Pro Asn Leu Ser Ile Ile Lys Pro Leu Asp Thr Ala Tyr Pro
                645                 650                 655
Ala Ala Arg Pro Pro Lys Gly Ser Thr Pro Thr Tyr Pro Thr Thr Lys
            660                 665                 670
Pro Ala Ala Ser Glu Val Ala Trp Pro Lys Asn Phe Asn Arg Ile Trp
        675                 680                 685
Arg Tyr Leu Tyr Pro Tyr Leu Asp Asn Pro Glu Gly Ala Ala Ala Asn
    690                 695                 700
Ser Ser Lys Thr Tyr Pro Tyr Pro Asp Gly Tyr Thr Thr Glu Pro Lys
705                 710                 715                 720
Pro Ala Pro Arg Ala Gly Gly Ala Glu Gly Gly Asn Pro Ala Leu Trp
                725                 730                 735
Asp Val Ala Phe Ser Val Gln Val Lys Val Thr Asn Thr Gly Ser Arg
            740                 745                 750
Asp Gly Arg Ala Val Ala Gln Leu Tyr Val Glu Leu Pro Ser Ser Leu
        755                 760                 765
Gly Leu Asp Thr Pro Ser Arg Gln Leu Arg Gln Phe Glu Lys Thr Lys
    770                 775                 780
Ile Leu Ala Ala Gly Glu Ser Glu Val Leu Thr Leu Asp Val Thr Arg
785                 790                 795                 800
Lys Asp Leu Ser Ala Trp Asp Val Val Gln Asp Trp Lys Ala Pro
                805                 810                 815
Val Asn Gly Glu Gly Val Lys Ile Trp Val Gly Glu Ser Val Ala Asp
            820                 825                 830
Leu Arg Val Gly Cys Val Gly Glu Gly Cys Ser Thr Leu
        835                 840                 845

<210> SEQ ID NO 5
<211> LENGTH: 2601
<212> TYPE: DNA
<213> ORGANISM: Aspergillus oryzae var. brunneus

<400> SEQUENCE: 5

```
atggctgcct tccggcctat tttggctctt ttgtcttact tggtcccggg ggctctgtcc      60
cacccccgagg cgaagactct gacatcaaga gcctctacag aagcttactc ccctccgtat    120
tacccggctc cgaacggagg atggatatcc gaatgggcca gtgcctacga aaggcacac     180
cgtgtcgtaa gtaacatgac gttggccgag aaggtgaatc tcacaagtgg cacgggtatc    240
tatatgggac cttgtgccgg tcagactggc agtgttcccc ggtttgggat ccccaacctg    300
tgccttcatg attctcccct cggagtccgc aattcggatc ataatacggc attcccggcc    360
ggcatcacgg ttgggccac atttgacaag gacctgatgt acgagcgcgg agtcggcctg    420
ggcgaagagg cgcgtggaaa gggtatcaac gttcttttag gccgtccgt gggccctatt    480
gggcggaagc cacggggagg ccgcaattgg gagggtttcg gagcggaccc cagtttacag    540
gcctttggtg gctcgttgac catcaaagga atgcaaagta cgggtgctat tgcttcgctc    600
```

```
aagcatctta tcggaaacga acaggagcag catcggatga gcagtgttat cactcagggc    660
tattcgtcaa atatcgatga caggactttg catgagctgt atctgtggcc attcgctgaa    720
agtgtaagag ccggtgctgg ttcggtcatg attgcgtata acgatgtgaa caggtccgcc    780
tgcagccaga atagcaagct catcaatgga atcctcaagg acgagctggg cttccagggc    840
tttgtcgtga ccgactggtt ggctcatatt ggcggagttt cgtcagcgtt ggctggtctg    900
gacatgagca tgccgggtga tggagctatc ccactcttgg cacgagtta ctggtcgtgg    960 gagctgtcgc gctctgtgct caatgggtcg gtcccggtcg agcgtctcaa tgacatggtc   1020
acgcgaatcg tcgcaacatg gtacaaaatg gggcaggaca agactatcc gctaccaaac   1080 ttctcctcaa acaccgagga tgagactggg ccgttgtatc ctggcgcctt attttcccca   1140
agtggcattg tcaaccaata cgtcaatgtc caaggcaacc ataatgtcac ggcccgggca   1200
atcgctagag acgcaatcac gttgctaaag aataacgaga atgtcctgcc tctgaaacgg   1260
aatgacacct aaagatcttt tggcaccgat gccgggacca attcggacgg gatcaactct   1320
tgcacggaca aaggctgcaa caaaggcgta ttgaccatgg gttggggaag cggaacatcc   1380
agactcccgt atctcatcac gccgcaagaa gcgatagcga atatctcatc caatgccgaa   1440
ttccacatca cagacacgtt tcctttgggc gtcactgcag gccccgatga catcgcgatc   1500
gtctttatca attcggactc cggcgagaac tacatcaccg ttgatggcaa tccaggagac   1560
cgtacgctgg cagggctgca cgcatggcac aatggcgaca acctggtcaa agctgccgca   1620
gaaaagttct caaacgtagt ggttgttgtg cataccgtgg gacccatcct gatggaagaa   1680
tggattgacc tcgactccgt taaagcggtg ctcgtcgctc acctcccagg acaggaggca   1740
ggctggtcac tcaccgatat cctctttggg gactatagtc ctagcggcca tctgccttac   1800
acaatccctc acagtgaatc agactacccg gagagcgtcg gtctaattgc tcagccattc   1860
ggccaaattc aagacgacta caccgagggc ctctacatcg attaccgaca cttcctgaag   1920
gcaaatatca ccccccgata cccattcggg cacggtctct cctacaccac gttcaacttt   1980
accgaaccca acctatccat catcaaagcc ctagacacag cctaccccgc cgcgcgaccc   2040
cccaaaggct ccacacccac ataccccacc gccaaacccg acgcatcaga agtcgcctgg   2100
cccaagaact tcaaccgcat ctggcgctac ctctacccct acctcgacaa cccagaaggc   2160
gcagccgcca actcctcaaa gacgtacccc taccccgacg gctacaccac agaacccaag   2220
cccgcccctc gcgccggcgg agcagaagga ggcaacccgg ccttatggga cgttaccttt   2280
tcggtccagg tcaaagtgac gaacacaggt tctcggatg gccgtgccgt tgcgcagctg    2340
tatgtggaat gcccagtag tctggggctg gatacgccat ctcgacagct gcggcagttc    2400
gagaagacga agatcttggc tgcggggag agtgaggtgc ttacgttgga tgtcacgcgc    2460
aaggatctta gtgtttggga tgttgttgtt caggactgga aggcgcctgt gaatggagag    2520
ggagttaaga tttgggttgg ggagagcgtt gcggatttga gggttggatg tgtggttgga    2580
gagggatgtt ctactttgta g                                               2601
```

<210> SEQ ID NO 6
<211> LENGTH: 2708
<212> TYPE: DNA
<213> ORGANISM: Aspergillus oryzae var. brunneus

<400> SEQUENCE: 6

```
atggctgcct tcccggccta tttggctctt ttgtcttact tggtcccggg ggctctgtcc     60
```

```
caccccgagg cgaagactct gacatcaaga gcctctacag aagcttactc ccctccgtat    120
tacccggctc cgaacggagg atggatatcc gaatgggcca gtgcctacga aaggcacac    180 cgtgtcgtaa gtaacatgac gttggccgag aaggtgaatc tcacaagtgg cacgggtatc    240
tatatgggac cttgtgccgg tcagactggc agtgttcccc ggtttgggat ccccaacctg    300
tgccttcatg attctcccct cggagtccgc aattcggatc ataatacggc attcccggcc    360
ggcatcacgg ttggggccac atttgacaag gacctgatgt acgagcgcgg agtcggcctg    420
ggcgaagagg cgcgtggaaa gggtatcaac gttcttttag gccgtccgt gggccctatt     480 gggcggaagc cacggggagg ccgcaattgg gagggtttcg gagcggaccc cagtttacag    540
gcctttggtg gctcgttgac catcaaagga atgcaaagta cgggtgctat tgcttcgctc    600
aagcatctta tcggaaacga acaggagcag catcggatga gcagtgttat cactcagggc    660
tattcgtcaa atatcgatga caggactttg catgagctgt atctgtggcc attcgctgaa    720
agtgtaagag ccggtgctgg ttcggtcatg attgcgtata cgatgtaag ccaatctccg     780 caccttcacc tcggacagga tgactaagta gagtgtaggt gaacaggtcc gcctgcagcc    840
agaatagcaa gctcatcaat ggaatcctca aggacgagct gggcttccag ggctttgtcg    900
tgaccgactg gttggctcat attggcgcag tttcgtcagc gttggctggt ctggacatga    960
gcatgccggg tgatggagct atcccactct gggcacgag ttactggtcg tgggagctgt    1020
cgcgctctgt gctcaatggg tcggtcccgg tcgagcgtct caatgacatg gtagacactc    1080
caacagtgcc agttttgcct tttagctaat gcgaggaatt acaggtcacg cgaatcgtcg    1140
caacatggta caaaatgggg caggacaaag actatccgct accaaacttc tcctcaaaca    1200
ccgaggatga gactgggccg ttgtatcctg gcgccttatt ttccccaagt ggcattgtca    1260
accaatacgt caatgtccaa ggcaaccata atgtcacggc ccgggcaatc gctagagacg    1320
caatcacgtt gctaaagaat aacgagaatg tcctgcctct gaaacggaat gacaccttaa    1380
agatctttgg caccgatgcc gggaccaatt cggacgggat caactcttgc acggacaaag    1440
gctgcaacaa aggcgtattg accatgggtt ggggaagcgg aacatccaga ctcccgtatc    1500
tcatcacgcc gcaagaagcg atagcgaata tctcatccaa tgccgaattc cacatcacag    1560
acacgtttcc tttgggcgtc actgcaggcc ccgatgacat cgcgatcgtc tttatcaatt    1620
cggactccgg cgagaactac atcaccgttg atggcaatcc aggagaccgt acgctggcag    1680
ggctgcacgc atggcacaat ggcgacaacc tggtcaaagc tgccgcagaa aagttctcaa    1740
acgtagtggt tgttgtgcat accgtgggac ccatcctgat ggaagaatgg attgacctcg    1800
actccgttaa agcggtgctc gtcgctcacc tcccaggaca ggaggcaggc tggtcactca    1860
ccgatatcct cttggggac tatagtccta gcggccatct gccttacaca atccctcaca     1920
gtgaatcaga ctacccggag agcgtcggtc taattgctca gccattcggc caaattcaag    1980
acgactacac cgagggcctc tacatcgatt accgacactt cctgaaggca aatatcaccc    2040
cccgataccc attcggcac ggtctctcct acaccacgtt caactttacc gaacccaacc     2100
tatccatcat caaagcccta gacacagcct acccgccgc gcgacccccc aaaggctcca    2160
cacccacata ccccaccgcc aaacccgacg catcagaagt cgcctggccc aagaacttca    2220
accgcatctg gcgctacctc tacccctacc tcgacaaccc agaaggcgca gccgccaact    2280
cctcaaagac gtaccctac cccgacggct acaccacaga acccaagccc gcccctcgcg     2340
ccggcggagc agaaggaggc aacccggcct tatgggacgt taccttttcg gtccaggtca    2400
aagtgacgaa cacaggttct cgggatggcc gtgccgttgc gcagctgtat gtggaattgc    2460
```

```
ccagtagtct ggggctggat acgccatctc gacagctgcg gcagttcgag aagacgaaga    2520
tcttggctgc gggggagagt gaggtgctta cgttggatgt cacgcgcaag gatcttagtg    2580
tttgggatgt tgttgttcag gactggaagg cgcctgtgaa tggagaggga gttaagattt    2640
gggttgggga gagcgttgcg gatttgaggg ttggatgtgt ggttggagag ggatgttcta    2700
ctttgtag                                                             2708
```

<210> SEQ ID NO 7
<211> LENGTH: 866
<212> TYPE: PRT
<213> ORGANISM: Aspergillus oryzae var. brunneus

<400> SEQUENCE: 7

```
Met Ala Ala Phe Pro Ala Tyr Leu Ala Leu Leu Ser Tyr Leu Val Pro
1               5                   10                  15

Gly Ala Leu Ser His Pro Glu Ala Lys Thr Leu Thr Ser Arg Ala Ser
            20                  25                  30

Thr Glu Ala Tyr Ser Pro Pro Tyr Pro Ala Pro Asn Gly Gly Trp
        35                  40                  45

Ile Ser Glu Trp Ala Ser Ala Tyr Glu Lys Ala His Arg Val Val Ser
    50                  55                  60

Asn Met Thr Leu Ala Glu Lys Val Asn Leu Thr Ser Gly Thr Gly Ile
65                  70                  75                  80

Tyr Met Gly Pro Cys Ala Gly Gln Thr Gly Ser Val Pro Arg Phe Gly
                85                  90                  95

Ile Pro Asn Leu Cys Leu His Asp Ser Pro Leu Gly Val Arg Asn Ser
            100                 105                 110

Asp His Asn Thr Ala Phe Pro Ala Gly Ile Thr Val Gly Ala Thr Phe
        115                 120                 125

Asp Lys Asp Leu Met Tyr Glu Arg Gly Val Gly Leu Gly Glu Glu Ala
    130                 135                 140

Arg Gly Lys Gly Ile Asn Val Leu Leu Gly Pro Ser Val Gly Pro Ile
145                 150                 155                 160

Gly Arg Lys Pro Arg Gly Gly Arg Asn Trp Glu Gly Phe Gly Ala Asp
                165                 170                 175

Pro Ser Leu Gln Ala Phe Gly Gly Ser Leu Thr Ile Lys Gly Met Gln
            180                 185                 190

Ser Thr Gly Ala Ile Ala Ser Leu Lys His Leu Ile Gly Asn Glu Gln
        195                 200                 205

Glu Gln His Arg Met Ser Ser Val Ile Thr Gln Gly Tyr Ser Ser Asn
    210                 215                 220

Ile Asp Asp Arg Thr Leu His Glu Leu Tyr Leu Trp Pro Phe Ala Glu
225                 230                 235                 240

Ser Val Arg Ala Gly Ala Gly Ser Val Met Ile Ala Tyr Asn Asp Val
                245                 250                 255

Asn Arg Ser Ala Cys Ser Gln Asn Ser Lys Leu Ile Asn Gly Ile Leu
            260                 265                 270

Lys Asp Glu Leu Gly Phe Gln Gly Phe Val Val Thr Asp Trp Leu Ala
        275                 280                 285

His Ile Gly Gly Val Ser Ser Ala Leu Ala Gly Leu Asp Met Ser Met
    290                 295                 300

Pro Gly Asp Gly Ala Ile Pro Leu Leu Gly Thr Ser Tyr Trp Ser Trp
305                 310                 315                 320
```

-continued

```
Glu Leu Ser Arg Ser Val Leu Asn Gly Ser Val Pro Val Glu Arg Leu
            325                 330                 335

Asn Asp Met Val Thr Arg Ile Val Ala Thr Trp Tyr Lys Met Gly Gln
        340                 345                 350

Asp Lys Asp Tyr Pro Leu Pro Asn Phe Ser Ser Asn Thr Glu Asp Glu
    355                 360                 365

Thr Gly Pro Leu Tyr Pro Gly Ala Leu Phe Ser Pro Ser Gly Ile Val
370                 375                 380

Asn Gln Tyr Val Asn Val Gln Gly Asn His Asn Val Thr Ala Arg Ala
385                 390                 395                 400

Ile Ala Arg Asp Ala Ile Thr Leu Leu Lys Asn Asn Glu Asn Val Leu
            405                 410                 415

Pro Leu Lys Arg Asn Asp Thr Leu Lys Ile Phe Gly Thr Asp Ala Gly
        420                 425                 430

Thr Asn Ser Asp Gly Ile Asn Ser Cys Thr Asp Lys Gly Cys Asn Lys
    435                 440                 445

Gly Val Leu Thr Met Gly Trp Gly Ser Gly Thr Ser Arg Leu Pro Tyr
450                 455                 460

Leu Ile Thr Pro Gln Glu Ala Ile Ala Asn Ile Ser Ser Asn Ala Glu
465                 470                 475                 480

Phe His Ile Thr Asp Thr Phe Pro Leu Gly Val Thr Ala Gly Pro Asp
            485                 490                 495

Asp Ile Ala Ile Val Phe Ile Asn Ser Asp Ser Gly Glu Asn Tyr Ile
        500                 505                 510

Thr Val Asp Gly Asn Pro Gly Asp Arg Thr Leu Ala Gly Leu His Ala
    515                 520                 525

Trp His Asn Gly Asp Asn Leu Val Lys Ala Ala Glu Lys Phe Ser
530                 535                 540

Asn Val Val Val Val His Thr Val Gly Pro Ile Leu Met Glu Glu
545                 550                 555                 560

Trp Ile Asp Leu Asp Ser Val Lys Ala Val Leu Val Ala His Leu Pro
            565                 570                 575

Gly Gln Glu Ala Gly Trp Ser Leu Thr Asp Ile Leu Phe Gly Asp Tyr
        580                 585                 590

Ser Pro Ser Gly His Leu Pro Tyr Thr Ile Pro His Ser Glu Ser Asp
    595                 600                 605

Tyr Pro Glu Ser Val Gly Leu Ile Ala Gln Pro Phe Gly Gln Ile Gln
610                 615                 620

Asp Asp Tyr Thr Glu Gly Leu Tyr Ile Asp Tyr Arg His Phe Leu Lys
625                 630                 635                 640

Ala Asn Ile Thr Pro Arg Tyr Pro Phe Gly His Gly Leu Ser Tyr Thr
            645                 650                 655

Thr Phe Asn Phe Thr Glu Pro Asn Leu Ser Ile Ile Lys Ala Leu Asp
        660                 665                 670

Thr Ala Tyr Pro Ala Ala Arg Pro Pro Lys Gly Ser Thr Pro Thr Tyr
    675                 680                 685

Pro Thr Ala Lys Pro Asp Ala Ser Glu Val Ala Trp Pro Lys Asn Phe
690                 695                 700

Asn Arg Ile Trp Arg Tyr Leu Tyr Pro Tyr Leu Asp Asn Pro Glu Gly
705                 710                 715                 720

Ala Ala Ala Asn Ser Ser Lys Thr Tyr Pro Tyr Pro Asp Gly Tyr Thr
            725                 730                 735

Thr Glu Pro Lys Pro Ala Pro Arg Ala Gly Gly Ala Glu Gly Gly Asn
```

```
                740                 745                 750
Pro Ala Leu Trp Asp Val Thr Phe Ser Val Gln Val Lys Val Thr Asn
            755                 760                 765

Thr Gly Ser Arg Asp Gly Arg Ala Val Ala Gln Leu Tyr Val Glu Leu
        770                 775                 780

Pro Ser Ser Leu Gly Leu Asp Thr Pro Ser Arg Gln Leu Arg Gln Phe
785                 790                 795                 800

Glu Lys Thr Lys Ile Leu Ala Ala Gly Glu Ser Glu Val Leu Thr Leu
                805                 810                 815

Asp Val Thr Arg Lys Asp Leu Ser Val Trp Asp Val Val Gln Asp
            820                 825                 830

Trp Lys Ala Pro Val Asn Gly Glu Gly Val Lys Ile Trp Val Gly Glu
            835                 840                 845

Ser Val Ala Asp Leu Arg Val Gly Cys Val Val Gly Glu Gly Cys Ser
        850                 855                 860

Thr Leu
865

<210> SEQ ID NO 8
<211> LENGTH: 846
<212> TYPE: PRT
<213> ORGANISM: Aspergillus oryzae var. brunneus

<400> SEQUENCE: 8

His Pro Glu Ala Lys Thr Leu Thr Ser Arg Ala Ser Thr Glu Ala Tyr
1               5                   10                  15

Ser Pro Pro Tyr Tyr Pro Ala Pro Asn Gly Gly Trp Ile Ser Glu Trp
                20                  25                  30

Ala Ser Ala Tyr Glu Lys Ala His Arg Val Val Ser Asn Met Thr Leu
            35                  40                  45

Ala Glu Lys Val Asn Leu Thr Ser Gly Thr Gly Ile Tyr Met Gly Pro
        50                  55                  60

Cys Ala Gly Gln Thr Gly Ser Val Pro Arg Phe Gly Ile Pro Asn Leu
65                  70                  75                  80

Cys Leu His Asp Ser Pro Leu Gly Val Arg Asn Ser Asp His Asn Thr
                85                  90                  95

Ala Phe Pro Ala Gly Ile Thr Val Gly Ala Thr Phe Asp Lys Asp Leu
            100                 105                 110

Met Tyr Glu Arg Gly Val Gly Leu Gly Glu Glu Ala Arg Gly Lys Gly
        115                 120                 125

Ile Asn Val Leu Leu Gly Pro Ser Val Gly Pro Ile Gly Arg Lys Pro
130                 135                 140

Arg Gly Gly Arg Asn Trp Glu Gly Phe Gly Ala Asp Pro Ser Leu Gln
145                 150                 155                 160

Ala Phe Gly Gly Ser Leu Thr Ile Lys Gly Met Gln Ser Thr Gly Ala
                165                 170                 175

Ile Ala Ser Leu Lys His Leu Ile Gly Asn Glu Gln Glu His Arg
            180                 185                 190

Met Ser Ser Val Ile Thr Gln Gly Tyr Ser Ser Asn Ile Asp Asp Arg
        195                 200                 205

Thr Leu His Glu Leu Tyr Leu Trp Pro Phe Ala Glu Ser Val Arg Ala
    210                 215                 220

Gly Ala Gly Ser Val Met Ile Ala Tyr Asn Asp Val Asn Arg Ser Ala
225                 230                 235                 240
```

```
Cys Ser Gln Asn Ser Lys Leu Ile Asn Gly Ile Leu Lys Asp Glu Leu
                245                 250                 255
Gly Phe Gln Gly Phe Val Val Thr Asp Trp Leu Ala His Ile Gly Gly
            260                 265                 270
Val Ser Ser Ala Leu Ala Gly Leu Asp Met Ser Met Pro Gly Asp Gly
            275                 280                 285
Ala Ile Pro Leu Leu Gly Thr Ser Tyr Trp Ser Trp Glu Leu Ser Arg
        290                 295                 300
Ser Val Leu Asn Gly Ser Val Pro Val Glu Arg Leu Asn Asp Met Val
305                 310                 315                 320
Thr Arg Ile Val Ala Thr Trp Tyr Lys Met Gly Gln Asp Lys Asp Tyr
                325                 330                 335
Pro Leu Pro Asn Phe Ser Ser Asn Thr Glu Asp Glu Thr Gly Pro Leu
            340                 345                 350
Tyr Pro Gly Ala Leu Phe Ser Pro Ser Gly Ile Val Asn Gln Tyr Val
        355                 360                 365
Asn Val Gln Gly Asn His Asn Val Thr Ala Arg Ala Ile Ala Arg Asp
    370                 375                 380
Ala Ile Thr Leu Leu Lys Asn Asn Glu Asn Val Leu Pro Leu Lys Arg
385                 390                 395                 400
Asn Asp Thr Leu Lys Ile Phe Gly Thr Asp Ala Gly Thr Asn Ser Asp
                405                 410                 415
Gly Ile Asn Ser Cys Thr Asp Lys Gly Cys Asn Lys Gly Val Leu Thr
            420                 425                 430
Met Gly Trp Gly Ser Gly Thr Ser Arg Leu Pro Tyr Leu Ile Thr Pro
        435                 440                 445
Gln Glu Ala Ile Ala Asn Ile Ser Ser Asn Ala Glu Phe His Ile Thr
    450                 455                 460
Asp Thr Phe Pro Leu Gly Val Thr Ala Gly Pro Asp Asp Ile Ala Ile
465                 470                 475                 480
Val Phe Ile Asn Ser Asp Ser Gly Glu Asn Tyr Ile Thr Val Asp Gly
                485                 490                 495
Asn Pro Gly Asp Arg Thr Leu Ala Gly Leu His Ala Trp His Asn Gly
            500                 505                 510
Asp Asn Leu Val Lys Ala Ala Ala Glu Lys Phe Ser Asn Val Val Val
        515                 520                 525
Val Val His Thr Val Gly Pro Ile Leu Met Glu Glu Trp Ile Asp Leu
    530                 535                 540
Asp Ser Val Lys Ala Val Leu Val Ala His Leu Pro Gly Gln Glu Ala
545                 550                 555                 560
Gly Trp Ser Leu Thr Asp Ile Leu Phe Gly Asp Tyr Ser Pro Ser Gly
                565                 570                 575
His Leu Pro Tyr Thr Ile Pro His Ser Glu Ser Asp Tyr Pro Glu Ser
            580                 585                 590
Val Gly Leu Ile Ala Gln Pro Phe Gly Gln Ile Gln Asp Asp Tyr Thr
        595                 600                 605
Glu Gly Leu Tyr Ile Asp Tyr Arg His Phe Leu Lys Ala Asn Ile Thr
    610                 615                 620
Pro Arg Tyr Pro Phe Gly His Gly Leu Ser Tyr Thr Thr Phe Asn Phe
625                 630                 635                 640
Thr Glu Pro Asn Leu Ser Ile Ile Lys Ala Leu Asp Thr Ala Tyr Pro
                645                 650                 655
Ala Ala Arg Pro Pro Lys Gly Ser Thr Pro Thr Tyr Pro Thr Ala Lys
```

| | 660 | | | 665 | | | 670 | | | | |
|---|---|---|---|---|---|---|---|---|---|---|---|
| Pro | Asp | Ala | Ser | Glu | Val | Ala | Trp | Pro | Lys | Asn | Phe | Asn | Arg | Ile | Trp |

Arg Tyr Leu Tyr Pro Tyr Leu Asp Asn Pro Glu Gly Ala Ala Asn
       690                  695                 700

Ser Ser Lys Thr Tyr Pro Tyr Pro Asp Gly Tyr Thr Thr Glu Pro Lys
705              710             715                  720

Pro Ala Pro Arg Ala Gly Gly Ala Glu Gly Gly Asn Pro Ala Leu Trp
              725                 730                 735

Asp Val Thr Phe Ser Val Gln Val Lys Val Thr Asn Thr Gly Ser Arg
              740                 745                 750

Asp Gly Arg Ala Val Ala Gln Leu Tyr Val Glu Leu Pro Ser Ser Leu
              755                 760                 765

Gly Leu Asp Thr Pro Ser Arg Gln Leu Arg Gln Phe Glu Lys Thr Lys
       770                  775                 780

Ile Leu Ala Ala Gly Glu Ser Glu Val Leu Thr Leu Asp Val Thr Arg
785              790                 795                 800

Lys Asp Leu Ser Val Trp Asp Val Val Gln Asp Trp Lys Ala Pro
              805                 810                 815

Val Asn Gly Glu Gly Val Lys Ile Trp Val Gly Glu Ser Val Ala Asp
              820                 825                 830

Leu Arg Val Gly Cys Val Val Gly Glu Gly Cys Ser Thr Leu
              835                 840                 845

```
<210> SEQ ID NO 9
<211> LENGTH: 2586
<212> TYPE: DNA
<213> ORGANISM: Aspergillus oryzae var. brunneus

<400> SEQUENCE: 9
atgaagcttg gttggatcga ggtggccgca ttggcggctg cctcagtagt cagtgccaag      60
gatgatctcg cgtactcccc tcctttctac ccttccccat gggcagatgg tcagggtgaa     120
tgggcggaag tatacaaacg cgctgtagac atagtttccc agatgacgtt gacagagaaa     180
gtcaacttaa cgactggaac aggatggcaa ctagagaggg tgttggaca aactggcagt      240
gttcccagac tcaacatccc cagcttgtgt ttgcaggata gtcctcttgg tattcgtttc     300
tcggactaca attcagcttt ccctgcgggt gttaatgtcg ctgccacctg ggacaagacg     360
ctcgcctacc ttcgtggtca ggcaatgggt gaggagttca gtgataaggg tattgacgtt     420
cagctgggtc ctgctgctgg ccctctcggt gctcatccgg atggcggtag aaactgggaa     480
ggtttctcac cagatccagc cctcaccggt gtactttttg cggagacgat taagggtatt     540
caagatgctg gtgtcattgc gacagctaag cattatatca tgaacgaaca agagcatttc     600
cgccaacaac ccgaggctgc gggttacgga ttcaacgtaa gcgacagttt gagttccaac     660
gttgatgaca agactatgca tgaattgtac ctctggccct tcgcggatgc agtacgcgct     720
ggagtcggtg ctgtcatgtg ctcttacaac caaatcaaca acagctacgg ttgcgagaat     780
agcgaaactc tgaacaagct tttgaaggcg gagcttggtt tccaaggctt cgtcatgagt     840
gattggaccg ctcatcacag cggcgtaggc gctgctttag caggtctgga tatgtcgatg     900
cccggtgatg ttaccttcga tagtggtacg tctttctggg gtgcaaactt gacggtcggt     960
gtccttaacg gtacaatccc ccaatggcgt gttgatgaca tggctgtccg tatcatggcc    1020
gcttattaca aggttggccg cgacaccaaa tacaccccctc ccaacttcag ctcgtggacc    1080
```

```
agggacgaat atggtttcgc gcataaccat gtttcggaag gtgcttacga gagggtcaac    1140
gaattcgtgg acgtgcaacg cgatcatgcc gacctaatcc gtcgcatcgg cgcgcagagc    1200
actgttctgc tgaagaacaa gggtgccttg cccttgagcc gcaaggaaaa gctggtcgcc    1260
cttctgggag aggatgcggg ttccaactcg tggggcgcta acggctgtga tgaccgtggt    1320
tgcgataacg gtaccttgc catggcctgg ggtagcggta ctgcgaattt cccataccctc    1380 gtgacaccag agcaggcgat tcagaacgaa gttcttcagg gccgtggtaa tgtcttcgcc    1440
gtgaccgaca gttgggcgct cgacaagatc gctgcggctg cccgccaggc cagcgtatct    1500
ctcgtgttcg tcaactccga ctcaggagaa ggctatctta gtgtggatgg aaatgagggc    1560
gatcgtaaca acatcactct gtggaagaac ggcgacaatg tggtcaagac cgcagcgaat    1620
aactgtaaca acaccgttgt catcatccac tccgtcggac cagttttgat cgatgaatgg    1680
tatgaccacc ccaatgtcac tggtattctc tgggctggtc tgccaggcca ggagtctggt    1740
aactccattg ccgatgtgct gtacggtcgt gtcaaccctg cgccaagtc tcctttcact    1800 tggggcaaga cccgggagtc gtatggttct cccttggtca aggatgccaa caatggcaac    1860
ggagcgcccc agtctgattt cacccagggt gttttcatcg attaccgcca tttcgataag    1920
ttcaatgaga ccctatcta cgagtttggc tacggcttga gctacaccac cttcgagctc    1980
tccgacctcc atgttcagcc cctgaacgcg tcccgataca ctcccaccag tggcatgact    2040
gaagctgcaa gaactttgg tgaaattggc gatgcgtcgg agtacgtgta ccggaggggg    2100
ctggaaagga tccatgagtt tatctatccc tggatcaact ctaccgacct gaaggcatcg    2160
tctgacgatt ctaactacgg ctgggaagac tccaagtata ttcccgaagg cgccacggat    2220
gggtctgccc agccccgttt gcccgctagt ggtggtgccg aggaaaaccc cggtctgtac    2280
gaggatcttt tccgcgtctc tgtgaaggtc aagaacacgg gcaatgtcgc cggtgatgaa    2340
gttcctcagc tgtacgtttc cctaggcggc ccgaatgagc ccaaggtggt actgcgcaag    2400
tttgagcgta ttcacttggc ccccttcgcag gaggccgtgt ggacaacgac ccttacccgt    2460
cgtgaccttg caaactggga cgtttcggct caggactgga ccgtcactcc ttaccccaag    2520
acgatctacg ttggaaactc ctcacggaaa ctgccgctcc aggcctcgct gcctaaggcc    2580
cagtaa                                                                2586
```

<210> SEQ ID NO 10
<211> LENGTH: 2891
<212> TYPE: DNA
<213> ORGANISM: Aspergillus oryzae var. brunneus

<400> SEQUENCE: 10

```
atgaagcttg gttggatcga ggtggccgca ttggcggctg cctcagtagt cagtgccaag      60
gtatgcttca gcatctcata cggtgctatt cgactcaatt gaatcagctt tttaacaatt     120
tttactctga ataggatgat ctcgcgtact cccctccttt ctaccccttcc ccatgggcag    180 atggtcaggg tgaatgggcg gaagtataca acgcgctgt agacatagtt tcccagatga     240
cgttgacaga gaaagtcaac ttaacgactg aacagggta agcttgcgta tgccttagcg     300
tgtctgaagc tcgattagct aaagtacttc agatggcaac tagagaggtg tgttggacaa    360
actggcagtg ttcccaggta agtagatttt cacatgactt tatactctta cggaaggctg    420
attgttgtga atatagactc aacatcccca gcttgtgttt gcaggatagt cctcttggta    480
ttcgtttctg tacgtgtggc ttttatttcc ctttccttcc taacatgttg ctaacagtag    540
acgcgcagcg gactacaatt cagctttccc tgcgggtgtt aatgtcgctg ccacctggga    600
```

```
caagacgctc gcctaccttc gtggtcaggc aatgggtgag gagttcagtg ataagggtat      660
tgacgttcag ctgggtcctg ctgctggccc tctcggtgct catccggatg gcggtagaaa      720
ctgggaaggt ttctcaccag atccagcccct caccggtgta cttttttgcgg agacgattaa    780 gggtattcaa gatgctggtg tcattgcgac agctaagcat tatatcatga acgaacaaga      840
gcatttccgc caacaacccg aggctgcggg ttacggattc aacgtaagcg acagtttgag      900
ttccaacgtt gatgacaaga ctatgcatga attgtacctc tggcccttcg cggatgcagt      960
acgcgctgga gtcggtgctg tcatgtgctc ttacaaccaa atcaacaaca gctacggttg     1020
cgagaatagc gaaactctga acaagctttt gaaggcggag cttggtttcc aaggcttcgt     1080
catgagtgat tggaccgctc atcacagcgg cgtaggcgct gctttagcag gtctggatat     1140
gtcgatgccc ggtgatgtta ccttcgatag tggtacgtct ttctggggtg caaacttgac     1200
ggtcggtgtc cttaacggta caatccccca atggcgtgtt gatgacatgg ctgtccgtat     1260
catggccgct tattacaagg ttggccgcga caccaaatac accctcccca acttcagctc     1320
gtggaccagg gacgaatatg gtttcgcgca taaccatgtt tcggaaggtg cttacgagag     1380
ggtcaacgaa ttcgtggacg tgcaacgcga tcatgccgac ctaatccgtc gcatcggcgc     1440
gcagagcact gttctgctga agaacaaggg tgccttgccc ttgagccgca aggaaaagct     1500
ggtcgccctt ctgggagagg atgcgggttc caactcgtgg ggcgctaacg gctgtgatga     1560
ccgtggttgc gataacggta cccttgccat ggcctggggt agcggtactg cgaatttccc     1620
atacctcgtg acaccagagc aggcgattca gaacgaagtt cttcagggcc gtggtaatgt     1680
cttcgccgtg accgacagtt gggcgctcga caagatcgct gcggctgccc gccaggccag     1740
cgtatctctc gtgttcgtca actccgactc aggagaaggc tatcttagtg tggatggaaa     1800
tgagggcgat cgtaacaaca tcactctgtg gaagaacggc gacaatgtgg tcaagaccgc     1860
agcgaataac tgtaacaaca ccgttgtcat catccactcc gtcggaccag ttttgatcga     1920
tgaatggtat gaccacccca atgtcactgg tattctctgg gctggtctgc caggccagga     1980
gtctggtaac tccattgccg atgtgctgta cggtcgtgtc aaccctggcg ccaagtctcc     2040
tttcacttgg ggcaagaccc gggagtcgta tggttctccc ttggtcaagg atgccaacaa     2100
tggcaacgga gcgcccccagt ctgatttcac ccagggtgtt ttcatcgatt accgccattt    2160
cgataagttc aatgagaccc ctatctacga gtttggctac ggcttgagct acaccacctt     2220
cgagctctcc gacctccatg ttcagcccct gaacgcgtcc cgatacactc ccaccagtgg     2280
catgactgaa gctgcaaaga actttggtga aattggcgat gcgtcggagt acgtgtatcc     2340
ggaggggctg gaaaggatcc atgagtttat ctatccctgg atcaactcta ccgacctgaa     2400
ggcatcgtct gacgattcta actacggctg gaagactcc aagtatattc cgaaggcgc      2460 cacggatggg tctgcccagc ccgtttgcc cgctagtggt ggtgccggag gaaacccccgg     2520 tctgtacgag gatctttttcc gcgtctctgt gaaggtcaag aacacgggca atgtcgccgg    2580
tgatgaagtt cctcagctgg taagttgacc tgattgggtg atgtgtaata atttcaatgc     2640
taactttttc tgtgtagtac gtttccctag gcggcccgaa tgagcccaag gtggtactgc     2700
gcaagtttga gcgtattcac ttggcccctt cgcaggagge cgtgtggaca acgacccctta    2760 cccgtcgtga ccttgcaaac tgggacgttt cggctcagga ctggaccgtc actccttacc     2820
ccaagacgat ctacgttgga aactcctcac ggaaactgcc gctccaggcc tcgctgccta     2880
aggcccagta a                                                          2891
```

<210> SEQ ID NO 11
<211> LENGTH: 861
<212> TYPE: PRT
<213> ORGANISM: Aspergillus oryzae var. brunneus

<400> SEQUENCE: 11

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380
```

```
Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Gly Tyr
                500                 505                 510

Leu Ser Val Asp Gly Asn Glu Gly Asp Arg Asn Asn Ile Thr Leu Trp
            515                 520                 525

Lys Asn Gly Asp Asn Val Val Lys Thr Ala Ala Asn Cys Asn Asn
530                 535                 540

Thr Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
                580                 585                 590

Pro Gly Ala Lys Ser Pro Phe Thr Trp Gly Lys Thr Arg Glu Ser Tyr
            595                 600                 605

Gly Ser Pro Leu Val Lys Asp Ala Asn Asn Gly Asn Gly Ala Pro Gln
        610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800
```

```
Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860

<210> SEQ ID NO 12
<211> LENGTH: 842
<212> TYPE: PRT
<213> ORGANISM: Aspergillus oryzae var. brunneus

<400> SEQUENCE: 12

Lys Asp Asp Leu Ala Tyr Ser Pro Pro Phe Tyr Pro Ser Pro Trp Ala
1               5                   10                  15

Asp Gly Gln Gly Glu Trp Ala Glu Val Tyr Lys Arg Ala Val Asp Ile
            20                  25                  30

Val Ser Gln Met Thr Leu Thr Glu Lys Val Asn Leu Thr Thr Gly Thr
        35                  40                  45

Gly Trp Gln Leu Glu Arg Cys Val Gly Gln Thr Gly Ser Val Pro Arg
    50                  55                  60

Leu Asn Ile Pro Ser Leu Cys Leu Gln Asp Ser Pro Leu Gly Ile Arg
65                  70                  75                  80

Phe Ser Asp Tyr Asn Ser Ala Phe Pro Ala Gly Val Asn Val Ala Ala
                85                  90                  95

Thr Trp Asp Lys Thr Leu Ala Tyr Leu Arg Gly Gln Ala Met Gly Glu
            100                 105                 110

Glu Phe Ser Asp Lys Gly Ile Asp Val Gln Leu Gly Pro Ala Ala Gly
        115                 120                 125

Pro Leu Gly Ala His Pro Asp Gly Gly Arg Asn Trp Glu Gly Phe Ser
    130                 135                 140

Pro Asp Pro Ala Leu Thr Gly Val Leu Phe Ala Glu Thr Ile Lys Gly
145                 150                 155                 160

Ile Gln Asp Ala Gly Val Ile Ala Thr Ala Lys His Tyr Ile Met Asn
                165                 170                 175

Glu Gln Glu His Phe Arg Gln Pro Glu Ala Ala Gly Tyr Gly Phe
            180                 185                 190

Asn Val Ser Asp Ser Leu Ser Ser Asn Val Asp Asp Lys Thr Met His
    195                 200                 205

Glu Leu Tyr Leu Trp Pro Phe Ala Asp Ala Val Arg Ala Gly Val Gly
    210                 215                 220

Ala Val Met Cys Ser Tyr Asn Gln Ile Asn Asn Ser Tyr Gly Cys Glu
225                 230                 235                 240

Asn Ser Glu Thr Leu Asn Lys Leu Leu Lys Ala Glu Leu Gly Phe Gln
                245                 250                 255

Gly Phe Val Met Ser Asp Trp Thr Ala His His Ser Gly Val Gly Ala
            260                 265                 270

Ala Leu Ala Gly Leu Asp Met Ser Met Pro Gly Asp Val Thr Phe Asp
        275                 280                 285

Ser Gly Thr Ser Phe Trp Gly Ala Asn Leu Thr Val Gly Val Leu Asn
    290                 295                 300

Gly Thr Ile Pro Gln Trp Arg Val Asp Asp Met Ala Val Arg Ile Met
305                 310                 315                 320
```

```
Ala Ala Tyr Tyr Lys Val Gly Arg Asp Thr Lys Tyr Thr Pro Pro Asn
            325                 330                 335

Phe Ser Ser Trp Thr Arg Asp Glu Tyr Gly Phe Ala His Asn His Val
            340                 345                 350

Ser Glu Gly Ala Tyr Glu Arg Val Asn Glu Phe Val Asp Val Gln Arg
            355                 360                 365

Asp His Ala Asp Leu Ile Arg Arg Ile Gly Ala Gln Ser Thr Val Leu
            370                 375                 380

Leu Lys Asn Lys Gly Ala Leu Pro Leu Ser Arg Lys Glu Lys Leu Val
385                 390                 395                 400

Ala Leu Leu Gly Glu Asp Ala Gly Ser Asn Ser Trp Gly Ala Asn Gly
                405                 410                 415

Cys Asp Asp Arg Gly Cys Asp Asn Gly Thr Leu Ala Met Ala Trp Gly
                420                 425                 430

Ser Gly Thr Ala Asn Phe Pro Tyr Leu Val Thr Pro Glu Gln Ala Ile
                435                 440                 445

Gln Asn Glu Val Leu Gln Gly Arg Gly Asn Val Phe Ala Val Thr Asp
            450                 455                 460

Ser Trp Ala Leu Asp Lys Ile Ala Ala Ala Arg Gln Ala Ser Val
465                 470                 475                 480

Ser Leu Val Phe Val Asn Ser Asp Ser Gly Glu Gly Tyr Leu Ser Val
                485                 490                 495

Asp Gly Asn Glu Gly Asp Arg Asn Asn Ile Thr Leu Trp Lys Asn Gly
                500                 505                 510

Asp Asn Val Val Lys Thr Ala Ala Asn Cys Asn Asn Thr Val Val
            515                 520                 525

Ile Ile His Ser Val Gly Pro Val Leu Ile Asp Glu Trp Tyr Asp His
            530                 535                 540

Pro Asn Val Thr Gly Ile Leu Trp Ala Gly Leu Pro Gly Gln Glu Ser
545                 550                 555                 560

Gly Asn Ser Ile Ala Asp Val Leu Tyr Gly Arg Val Asn Pro Gly Ala
                565                 570                 575

Lys Ser Pro Phe Thr Trp Gly Lys Thr Arg Glu Ser Tyr Gly Ser Pro
                580                 585                 590

Leu Val Lys Asp Ala Asn Asn Gly Asn Gly Ala Pro Gln Ser Asp Phe
            595                 600                 605

Thr Gln Gly Val Phe Ile Asp Tyr Arg His Phe Asp Lys Phe Asn Glu
            610                 615                 620

Thr Pro Ile Tyr Glu Phe Gly Tyr Gly Leu Ser Tyr Thr Thr Phe Glu
625                 630                 635                 640

Leu Ser Asp Leu His Val Gln Pro Leu Asn Ala Ser Arg Tyr Thr Pro
                645                 650                 655

Thr Ser Gly Met Thr Glu Ala Ala Lys Asn Phe Gly Glu Ile Gly Asp
                660                 665                 670

Ala Ser Glu Tyr Val Tyr Pro Glu Gly Leu Glu Arg Ile His Glu Phe
            675                 680                 685

Ile Tyr Pro Trp Ile Asn Ser Thr Asp Leu Lys Ala Ser Ser Asp Asp
            690                 695                 700

Ser Asn Tyr Gly Trp Glu Asp Ser Lys Tyr Ile Pro Glu Gly Ala Thr
705                 710                 715                 720

Asp Gly Ser Ala Gln Pro Arg Leu Pro Ala Ser Gly Gly Ala Gly Gly
                725                 730                 735
```

```
Asn Pro Gly Leu Tyr Glu Asp Leu Phe Arg Val Ser Val Lys Val Lys
            740                 745                 750

Asn Thr Gly Asn Val Ala Gly Asp Glu Val Pro Gln Leu Tyr Val Ser
        755                 760                 765

Leu Gly Gly Pro Asn Glu Pro Lys Val Val Leu Arg Lys Phe Glu Arg
    770                 775                 780

Ile His Leu Ala Pro Ser Gln Glu Ala Val Trp Thr Thr Thr Leu Thr
785                 790                 795                 800

Arg Arg Asp Leu Ala Asn Trp Asp Val Ser Ala Gln Asp Trp Thr Val
                805                 810                 815

Thr Pro Tyr Pro Lys Thr Ile Tyr Val Gly Asn Ser Ser Arg Lys Leu
        820                 825                 830

Pro Leu Gln Ala Ser Leu Pro Lys Ala Gln
        835                 840
```

<210> SEQ ID NO 13
<211> LENGTH: 2586
<212> TYPE: DNA
<213> ORGANISM: Aspergillus sojae

<400> SEQUENCE: 13

```
atgaagcttg gttggatcga ggtggccgca ttggtggctg cctcagtagt cagtgccaag      60
gatgatctcg cgtactcccc tcctttctac ccttccccgt gggcagatgg tcagggtgaa     120
tgggcggaag tatacaaacg cgctgtagac atagtttccc agatgacgtt gacagagaaa     180
gtcaacttaa cgactggaac aggatggcag ctagagaggt gtgttggaca aactggcagt     240
gttcccagac tcaacatccc cagcttgtgc ttgcaggata gtcctcttgg tattcgtttc     300
tcggactata attcggcttt ccctgcgggt gttaatgtcg ctgccacttg ggacaagacg     360
ctcgcctacc tccgcggtca ggcaatgggt gaagagttca gtgacaaggg cattgacgtt     420
cagctgggtc ctgctgctgg ccctctcggt gctcatccgg acggcggtag aaactgggaa     480
gggttctcac cagatccagc cctcaccggt gtactgtttg cagagacgat taagggtatc     540
caagatgctg gtgtcattgc gacagctaag cattatatca tgaacgaaca agagcatttc     600
cgccaacaac ccgaggctgc gggttacgga ttcaacgtaa cgacagtttt gagctccaac     660
gttgatgaca agactatcca tgaattatac ctctggccct tcgcggatgc agtacgcgct     720
ggagtcggtg ctgtcatgtg ctcttacaac caaatcaaca cagctacgg ttgcagaat     780
agcgaaactc tgaacaagct tttgaaggcg gaacttggtt ccaaggcttc cgtcatgagt     840
gattggaccg ctcatcacag cggtgtaggc gctgctttag caggtatgga tatgtcgatg     900
cccggtgatg ttaccttcga gtggtacg tctttctggg gtgcaaactt gacggtcggt     960
gtccttaacg gtacaatccc caatggcgc gttgatgaca tggctgtccg tatcatggcc    1020
gcttattaca aggttggccg cgacaccaag tacactcctc ccaacttcag ctcgtggacc    1080
agggacgaat atggtttcgc gcataaccat gtttcggaag tgcttacga gagggtcaac    1140
gaattcgtgg acgtgcaacg cgatcatgcc gacctgatcc gtcgcatcgg cgcgcagagc    1200
actgttctgc tgaagaacaa gggtgccttg cccttgagcc gcaaggaaaa gctggtcgcc    1260
cttctgggag aggatgcggg ttccaactcg tggggcgcta acggctgtga tgaccgtgga    1320
tgcgataacg gtaccttgc catggcctgg ggtagcggta ctgcgaattt cccataccct    1380
gtgacaccgg agcaggcgat tcagaacgaa gttcttcagg ccgtggtaa tgtcttcgcc    1440
gtgaccgaca gctgggcact cgacaagatc gctgcggctg cccgccaggc cagcgtatcc    1500
```

-continued

```
ctcgtattcg tcaactccga ctcgggagaa ggctatctta gtgtggatgg aaatgagggc      1560
gatcgcaaca atatcactct gtggaagaac ggtgacaatg tggtcaagac cgcggcgaat      1620
aactgtaaca acaccgttgt catcatccac tccgtcggac cagttttgat caatgaatgg      1680
tatgaccacc ctaatgtcac cggtattctc tgggctggtc tgccaggcca ggagtctggt      1740
aactccattg ccgatgtgct gtacggtcgt gtcaaccctg gtgccaagtc tcctttcact      1800
tggggcaaga ctcgggattc gtacggttct cccttggtca aggatgccaa caatggtaac      1860
ggagcgcccc agtctgattt cacccagggt gttttcatcg attaccgcca tttcgataag      1920
ttcaatgaga cccctatcta cgagtttggc tacggcttga gctacaccac cttcgaactc      1980
tccgacctcc atgttcagcc cctgaacgcg tcccaataca ctcccaccag tggcatgact      2040
gaagctgcaa gaactttggg tgaaattggc gatgcgtcgg agtacgtgta ccggaggggg      2100
ctggagagga tccatgagtt tatctatccc tggattaact ctaccgacct gaaggcatcg      2160
tctgacgatt ctaactacgg ctgggaagac tccgagtaca tccccgaagg cgccacggat      2220
gggtctgccc agccccgttt gccgctagcc ggtggtgccg aggaaacccc cggtctgtat      2280
gaggatcttt tccgcgtctc tgtgaaggtc aagaacacgg gcaatgtcgc cggtgatgaa      2340
gttcctcagc tgtacgtttc cctaggcggc ccgaatgagc ccaaggtggt gctgcgcaag      2400
tttgagcgta ttcacttggc ccccttcgcag gaggtcgtgt ggacaacgac ccttacccgt      2460
cgtgaccttg ccaactggga cgtttcggct caggactggg ccgtcactcc ttaccccaag      2520
acgatctacg ttggaaactc ctcacggaaa ctgcccctcc aggtctcgct gcctaaggct      2580
cagtaa                                                                2586
```

<210> SEQ ID NO 14
<211> LENGTH: 2892
<212> TYPE: DNA
<213> ORGANISM: Aspergillus sojae

<400> SEQUENCE: 14

```
atgaagcttg gttggatcga ggtggccgca ttggtggctg cctcagtagt cagtgccaag      60
gtatgcttca gcatctcata cggtgctatt caactcaatt gaatcagctt tttaacagtt      120
ttcactctga ataggatgat ctcgcgtact cccctccttt ctacccttcc ccgtgggcag      180
atggtcaggg tgaatgggcg gaagtataca aacgcgctgt agacatagtt tcccagatga      240
cgttgacaga gaaagtcaac ttaacgactg gaacagggta agattgcgta tgccttagcg      300
tgtctgaagc tcgattagct aacgtacttc agatggcagc tagagaggtg tgttggacaa      360
actggcagtg ttcccaggta agtaaatttt caacatgact ttatactctt acggaaggct      420
gattgtcgtg aatatagact caacatcccc agcttgtgct tgcaggatag tcctcttggt      480
attcgtttct gtacgtgtgg cccttatttc cctttccttc ctaacatgtt gctaacagta      540
gacgcgcagc ggactataat tcggcttttcc ctgcgggtgt taatgtcgct gccacttggg      600
acaagacgct cgcctacctc cgcggtcagg caatgggtga agagttcagt gacaagggca      660
ttgacgttca gctgggtcct gctgctggcc ctctcggtgc tcatccggac ggcggtagaa      720
actgggaagg ttctcacca gatccagccc tcaccggtgt actgtttgca gagacgatta      780
agggtatcca agatgctggt gtcattgcga cagctaagca ttatatcatg aacgaacaag      840
agcatttccg ccaacaaccc gaggctgcgg ttacggatt caacgtaagc gacagtttga      900
gctccaacgt tgatgacaag actatccatg aattataccc ctggcccttc gcggatgcag      960
tacgcgctgg agtcggtgct gtcatgtgct cttacaacca aatcaacaac agctacggtt      1020
```

```
gcgagaatag cgaaactctg aacaagcttt tgaaggcgga acttggtttc caaggcttcg    1080
tcatgagtga ttggaccgct catcacagcg gtgtaggcgc tgctttagca ggtatggata    1140
tgtcgatgcc cggtgatgtt accttcgata gtggtacgtc tttctggggt gcaaacttga    1200
cggtcggtgt ccttaacggt acaatccccc aatggcgcgt tgatgacatg gctgtccgta    1260
tcatggccgc ttattacaag gttggccgcg acaccaagta cactcctccc aacttcagct    1320
cgtggaccag ggacgaatat ggtttcgcgc ataaccatgt tcggaaggt gcttacgaga    1380 gggtcaacga attcgtggac gtgcaacgcg atcatgccga cctgatccgt cgcatcggcg    1440
cgcagagcac tgttctgctg aagaacaagg gtgccttgcc cttgagccgc aaggaaaagc    1500
tggtcgccct tctgggagag gatgcgggtt ccaactcgtg gggcgctaac ggctgtgatg    1560
accgtggatg cgataacggt acccttgcca tggcctgggg tagcggtact gcgaatttcc    1620
catacctcgt gacaccggag caggcgattc agaacgaagt tcttcagggc cgtggtaatg    1680
tcttcgccgt gaccgacagc tgggcactcg acaagatcgc tgcggctgcc cgccaggcca    1740
gcgtatccct cgtattcgtc aactccgact cgggagaagg ctatcttagt gtggatggaa    1800
atgagggcga tcgcaacaat atcactctgt ggaagaacgg tgacaatgtg gtcaagaccg    1860
cggcgaataa ctgtaacaac accgttgtca tcatccactc cgtcggacca gttttgatca    1920
atgaatggta tgaccaccct aatgtcaccg gtattctctg gctggtctg ccaggccagg    1980 agtctggtaa ctccattgcc gatgtgctgt acggtcgtgt caaccctggt gccaagtctc    2040
ctttcacttg gggcaagact cgggattcgt acggttctcc cttggtcaag gatgccaaca    2100
atggtaacgg agcgccccag tctgatttca cccaggtgt tttcatcgat taccgccatt    2160
tcgataagtt caatgagacc cctatctacg agtttggcta cggcttgagc tacaccacct    2220
tcgaactctc cgacctccat gttcagcccc tgaacgcgtc ccaatacact cccaccagtg    2280
gcatgactga agctgcaaag aactttggtg aaattggcga tgcgtcggag tacgtgtatc    2340
cggaggggct ggagaggatc catgagttta tctatccctg gattaactct accgacctga    2400
aggcatcgtc tgacgattct aactacggct gggaagactc cgagtacatc cccgaaggcg    2460
ccacggatgg gtctgcccag ccccgttttgc ccgctagcgg tggtgccgga ggaaaccccg    2520
gtctgtatga ggatcttttc cgcgtctctg tgaaggtcaa gaacacgggc aatgtcgccg    2580
gtgatgaagt tcctcagctg gtaagttgac ctgattgggt gatgtgtaat aatttcaatg    2640
ctaacttttt ctgtgtagta cgtttcccta ggcggcccga atgagcccaa ggtggtgctg    2700
cgcaagtttg agcgtattca cttggcccct tcgcaggagg tcgtgtggac aacgaccctt    2760
acccgtcgtg accttgccaa ctgggacgtt tcggctcagg actgggccgt cactccttac    2820
cccaagacga tctacgttgg aaactcctca cggaaactgc cctccaggt ctcgctgcct    2880 aaggctcagt aa                                                        2892
```

<210> SEQ ID NO 15
<211> LENGTH: 861
<212> TYPE: PRT
<213> ORGANISM: Aspergillus sojae

<400> SEQUENCE: 15

Met Lys Leu Gly Trp Ile Glu Val Ala Ala Leu Val Ala Ala Ser Val
1               5                   10                  15

Val Ser Ala Lys Asp Asp Leu Ala Tyr Ser Pro Pro Phe Tyr Pro Ser
            20                  25                  30

-continued

```
Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
 50                  55                  60

Thr Gly Thr Gly Trp Gln Leu Glu Arg Cys Val Gly Gln Thr Gly Ser
 65                  70                  75                  80

Val Pro Arg Leu Asn Ile Pro Ser Leu Cys Leu Gln Asp Ser Pro Leu
                 85                  90                  95

Gly Ile Arg Phe Ser Asp Tyr Asn Ser Ala Phe Pro Ala Gly Val Asn
                100                 105                 110

Val Ala Ala Thr Trp Asp Lys Thr Leu Ala Tyr Leu Arg Gly Gln Ala
            115                 120                 125

Met Gly Glu Glu Phe Ser Asp Lys Gly Ile Asp Val Gln Leu Gly Pro
130                 135                 140

Ala Ala Gly Pro Leu Gly Ala His Pro Asp Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Met Asn Glu Gln Glu His Phe Arg Gln Gln Pro Glu Ala Ala Gly
            195                 200                 205

Tyr Gly Phe Asn Val Ser Asp Ser Leu Ser Ser Asn Val Asp Asp Lys
            210                 215                 220

Thr Ile His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
            275                 280                 285

Val Gly Ala Ala Leu Ala Gly Met Asp Met Ser Met Pro Gly Asp Val
290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Met Ala Val
                325                 330                 335

Arg Ile Met Ala Ala Tyr Tyr Lys Val Gly Arg Asp Thr Lys Tyr Thr
                340                 345                 350

Pro Pro Asn Phe Ser Ser Trp Thr Arg Asp Glu Tyr Gly Phe Ala His
            355                 360                 365

Asn His Val Ser Glu Gly Ala Tyr Glu Arg Val Asn Glu Phe Val Asp
370                 375                 380

Val Gln Arg Asp His Ala Asp Leu Ile Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
                420                 425                 430

Ala Asn Gly Cys Asp Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
```

```
            450                 455                 460
Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
            485                 490                 495

Ala Ser Val Ser Leu Val Phe Val Asn Ser Asp Ser Gly Glu Gly Tyr
                500                 505                 510

Leu Ser Val Asp Gly Asn Glu Gly Asp Arg Asn Asn Ile Thr Leu Trp
            515                 520                 525

Lys Asn Gly Asp Asn Val Val Lys Thr Ala Ala Asn Asn Cys Asn Asn
            530                 535                 540

Thr Val Val Ile Ile His Ser Val Gly Pro Val Leu Ile Asn Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
                580                 585                 590

Pro Gly Ala Lys Ser Pro Phe Thr Trp Gly Lys Thr Arg Asp Ser Tyr
            595                 600                 605

Gly Ser Pro Leu Val Lys Asp Ala Asn Asn Gly Asn Gly Ala Pro Gln
            610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Gln
                660                 665                 670

Tyr Thr Pro Thr Ser Gly Met Thr Glu Ala Ala Lys Asn Phe Gly Glu
            675                 680                 685

Ile Gly Asp Ala Ser Glu Tyr Val Tyr Pro Glu Gly Leu Glu Arg Ile
            690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Glu Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
            755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Val Val Trp Thr Thr
                805                 810                 815

Thr Leu Thr Arg Arg Asp Leu Ala Asn Trp Asp Val Ser Ala Gln Asp
            820                 825                 830

Trp Ala Val Thr Pro Tyr Pro Lys Thr Ile Tyr Val Gly Asn Ser Ser
            835                 840                 845

Arg Lys Leu Pro Leu Gln Val Ser Leu Pro Lys Ala Gln
850                 855                 860

<210> SEQ ID NO 16
```

<211> LENGTH: 842
<212> TYPE: PRT
<213> ORGANISM: Aspergillus sojae

<400> SEQUENCE: 16

```
Lys Asp Asp Leu Ala Tyr Ser Pro Pro Phe Tyr Pro Ser Pro Trp Ala
1               5                   10                  15

Asp Gly Gln Gly Glu Trp Ala Glu Val Tyr Lys Arg Ala Val Asp Ile
            20                  25                  30

Val Ser Gln Met Thr Leu Thr Glu Lys Val Asn Leu Thr Thr Gly Thr
        35                  40                  45

Gly Trp Gln Leu Glu Arg Cys Val Gly Gln Thr Gly Ser Val Pro Arg
    50                  55                  60

Leu Asn Ile Pro Ser Leu Cys Leu Gln Asp Ser Pro Leu Gly Ile Arg
65                  70                  75                  80

Phe Ser Asp Tyr Asn Ser Ala Phe Pro Ala Gly Val Asn Val Ala Ala
                85                  90                  95

Thr Trp Asp Lys Thr Leu Ala Tyr Leu Arg Gly Gln Ala Met Gly Glu
            100                 105                 110

Glu Phe Ser Asp Lys Gly Ile Asp Val Gln Leu Gly Pro Ala Ala Gly
        115                 120                 125

Pro Leu Gly Ala His Pro Asp Gly Gly Arg Asn Trp Glu Gly Phe Ser
    130                 135                 140

Pro Asp Pro Ala Leu Thr Gly Val Leu Phe Ala Glu Thr Ile Lys Gly
145                 150                 155                 160

Ile Gln Asp Ala Gly Val Ile Ala Thr Ala Lys His Tyr Ile Met Asn
                165                 170                 175

Glu Gln Glu His Phe Arg Gln Gln Pro Glu Ala Ala Gly Tyr Gly Phe
            180                 185                 190

Asn Val Ser Asp Ser Leu Ser Ser Asn Val Asp Asp Lys Thr Ile His
        195                 200                 205

Glu Leu Tyr Leu Trp Pro Phe Ala Asp Ala Val Arg Ala Gly Val Gly
    210                 215                 220

Ala Val Met Cys Ser Tyr Asn Gln Ile Asn Asn Ser Tyr Gly Cys Glu
225                 230                 235                 240

Asn Ser Glu Thr Leu Asn Lys Leu Leu Lys Ala Glu Leu Gly Phe Gln
                245                 250                 255

Gly Phe Val Met Ser Asp Trp Thr Ala His His Ser Gly Val Gly Ala
            260                 265                 270

Ala Leu Ala Gly Met Asp Met Ser Met Pro Gly Asp Val Thr Phe Asp
        275                 280                 285

Ser Gly Thr Ser Phe Trp Gly Ala Asn Leu Thr Val Gly Val Leu Asn
    290                 295                 300

Gly Thr Ile Pro Gln Trp Arg Val Asp Asp Met Ala Val Arg Ile Met
305                 310                 315                 320

Ala Ala Tyr Tyr Lys Val Gly Arg Asp Thr Lys Tyr Thr Pro Pro Asn
                325                 330                 335

Phe Ser Ser Trp Thr Arg Asp Glu Tyr Gly Phe Ala His Asn His Val
            340                 345                 350

Ser Glu Gly Ala Tyr Glu Arg Val Asn Glu Phe Val Asp Val Gln Arg
        355                 360                 365

Asp His Ala Asp Leu Ile Arg Arg Ile Gly Ala Gln Ser Thr Val Leu
    370                 375                 380

Leu Lys Asn Lys Gly Ala Leu Pro Leu Ser Arg Lys Glu Lys Leu Val
```

-continued

```
            385                 390                 395                 400
        Ala Leu Leu Gly Glu Asp Ala Gly Ser Asn Ser Trp Gly Ala Asn Gly
                            405                 410                 415

Cys Asp Asp Arg Gly Cys Asp Asn Gly Thr Leu Ala Met Ala Trp Gly
                            420                 425                 430

Ser Gly Thr Ala Asn Phe Pro Tyr Leu Val Thr Pro Glu Gln Ala Ile
                            435                 440                 445

Gln Asn Glu Val Leu Gln Gly Arg Gly Asn Val Phe Ala Val Thr Asp
                    450                 455                 460

Ser Trp Ala Leu Asp Lys Ile Ala Ala Ala Arg Gln Ala Ser Val
        465                 470                 475                 480

Ser Leu Val Phe Val Asn Ser Asp Ser Gly Glu Gly Tyr Leu Ser Val
                                485                 490                 495

Asp Gly Asn Glu Gly Asp Arg Asn Asn Ile Thr Leu Trp Lys Asn Gly
                            500                 505                 510

Asp Asn Val Val Lys Thr Ala Ala Asn Cys Asn Asn Thr Val Val
                            515                 520                 525

Ile Ile His Ser Val Gly Pro Val Leu Ile Asn Glu Trp Tyr Asp His
                    530                 535                 540

Pro Asn Val Thr Gly Ile Leu Trp Ala Gly Leu Pro Gly Gln Glu Ser
        545                 550                 555                 560

Gly Asn Ser Ile Ala Asp Val Leu Tyr Gly Arg Val Asn Pro Gly Ala
                            565                 570                 575

Lys Ser Pro Phe Thr Trp Gly Lys Thr Arg Asp Ser Tyr Gly Ser Pro
                            580                 585                 590

Leu Val Lys Asp Ala Asn Asn Gly Asn Gly Ala Pro Gln Ser Asp Phe
                            595                 600                 605

Thr Gln Gly Val Phe Ile Asp Tyr Arg His Phe Asp Lys Phe Asn Glu
                    610                 615                 620

Thr Pro Ile Tyr Glu Phe Gly Tyr Gly Leu Ser Tyr Thr Thr Phe Glu
        625                 630                 635                 640

Leu Ser Asp Leu His Val Gln Pro Leu Asn Ala Ser Gln Tyr Thr Pro
                            645                 650                 655

Thr Ser Gly Met Thr Glu Ala Ala Lys Asn Phe Gly Glu Ile Gly Asp
                            660                 665                 670

Ala Ser Glu Tyr Val Tyr Pro Glu Gly Leu Glu Arg Ile His Glu Phe
                            675                 680                 685

Ile Tyr Pro Trp Ile Asn Ser Thr Asp Leu Lys Ala Ser Ser Asp Asp
                    690                 695                 700

Ser Asn Tyr Gly Trp Glu Asp Ser Glu Tyr Ile Pro Glu Gly Ala Thr
        705                 710                 715                 720

Asp Gly Ser Ala Gln Pro Arg Leu Pro Ala Ser Gly Gly Ala Gly Gly
                            725                 730                 735

Asn Pro Gly Leu Tyr Glu Asp Leu Phe Arg Val Ser Val Lys Val Lys
                            740                 745                 750

Asn Thr Gly Asn Val Ala Gly Asp Glu Val Pro Gln Leu Tyr Val Ser
                            755                 760                 765

Leu Gly Gly Pro Asn Glu Pro Lys Val Val Leu Arg Lys Phe Glu Arg
                            770                 775                 780

Ile His Leu Ala Pro Ser Gln Glu Val Val Trp Thr Thr Thr Leu Thr
        785                 790                 795                 800

Arg Arg Asp Leu Ala Asn Trp Asp Val Ser Ala Gln Asp Trp Ala Val
                            805                 810                 815
```

Thr Pro Tyr Pro Lys Thr Ile Tyr Val Gly Asn Ser Ser Arg Lys Leu
                820                 825                 830

Pro Leu Gln Val Ser Leu Pro Lys Ala Gln
            835                 840

<210> SEQ ID NO 17
<211> LENGTH: 2598
<212> TYPE: DNA
<213> ORGANISM: Artificial sequence
<220> FEATURE:
<223> OTHER INFORMATION: synthetic DNA

<400> SEQUENCE: 17

| | |
|---|---|
| atgtttaaat ctgttgttta ttcaatttta gccgcttctt tggccaatgc agctagcgaa | 60 |
| ttcgagctcg agtctctgac atcaagagcc tctacagaag cttactcccc tccatattac | 120 |
| ccagctccga acggaggatg gatatccgaa tgggccagtg cctatgagaa ggcacaccgt | 180 |
| gtcgtaagta acatgacctt ggccgagaag gtgaatctca caagtggcac cggtatctac | 240 |
| atgggacctt gtgccggcca gactggcagt gttccccgtt ttgggatccc caacctgtgc | 300 |
| cttcatgatt ctcctctcgg agtccgtaat tcggatcata atacggcatt cccgccggc | 360 |
| atcacggtcg gggccacatt tgacaaggac ctgatgtacg agcgcggagt cggtctaggc | 420 |
| gaagaggcgc ggggaaaggg tatcaacgtt cttttagggc cgtccgtggg ccctattggg | 480 |
| cggaagccac ggggaggccg caattgggag ggtttcggag cggatcccag tttacaggcc | 540 |
| tttgggggct cgttgaccat taaaggaatg cagagtacgg tgctattgc ttcgctcaaa | 600 |
| catcttatcg gaaacgaaca ggagcagcat cggatgagca gtgttatcac tcaaggctat | 660 |
| tcgtcaaata tcgatgacag gactttgcat gagctgtatc tgtggccatt cgcggaaagt | 720 |
| gtaagagccg gtgctggttc ggtcatgatt gcgtataacg atgtgaacag gtccgcctgc | 780 |
| agccagaata gtaagctcat caatggaatc ctcaaggacg agctggggtt caggggcttt | 840 |
| gtcgtgaccg actggttggc tcatattggc ggagtttcgt cagcgttggc cggcctggac | 900 |
| atgagcatgc cgggtgacgg agctatccca ctcttgggca cgagttactg ggcgtgggag | 960 |
| ctgtcgcgct ccgtgctcaa tggctcggtc ccggtcgagc gtctcaatga catggtcacg | 1020 |
| cgaatcgtcg caacatggta caaaatgggg caggacaaag actatccgct accaaacttc | 1080 |
| tcctcaaaca ccgaggatga gactgggccg ttgtatcctg cgccttatt ttccccaagt | 1140 |
| ggcattgtca accaatacgt caatgtccaa ggcaaccata atgtcacggc ccgggcaatc | 1200 |
| gctagagatg caatcacgtt gctaaagaat aacgacaatg tcctgcctct gaaacggaat | 1260 |
| gccagcttga agatctttgg cactgatgcc ggggccaatt cggacgggat caattcttgc | 1320 |
| actgacaaag gctgcaacaa aggcgtattg accatgggct ggggaagcgg aacatccaga | 1380 |
| ctcccatatc tcattacgcc gcaagaagcg atagcgaata tctcatccaa tgccgaattc | 1440 |
| cacatcacgg acacgtttcc tttgggcgtc accgcaggcc tcgacgacat gcgatcgtc | 1500 |
| ttcatcaatt cggactccgg cgagaactac atcaccgtcg atggcaatcc tggagaccgt | 1560 |
| acgctggcag gctgaccgc atggcacaac ggcgacaacc ttgtcaaagc tgctgcagaa | 1620 |
| aagttctcaa acgtagtggt tgtagtgcac accgtggac ccatcctgat ggaagaatgg | 1680 |
| atcgacctcg actccgtcaa agcggtgctc gtcgctcact acccggaca ggaggcaggc | 1740 |
| tggtcactaa ccgacatcct ctttggggac tatagtccta gcggccatct gccttacaca | 1800 |
| atccctcgca gtgaatcaga ctacccagag agcgtcggat tgattgctca gccattcggc | 1860 |

| | |
|---|---|
| caaatccaag acgactatac cgaaggcctc tacatcgatt accgccactt cctaaaagca | 1920 |
| aacatcaccc cccgataccc attcggacac ggtctctcct acaccacgtt caacttcacc | 1980 |
| gaacccaacc tctccatcat caaacccta gacacagcct accccgccgc gcgacccct | 2040 |
| aaaggctcca cacccacata ccccaccacc aaacccgccg catcagaagt cgcctggccc | 2100 |
| aagaacttca accgcatctg cgctacctc taccctacc tcgacaaccc ggaaggcgca | 2160 |
| gccgccaact cctcaaagac ataccccttac ccagacggct acaccacaga gcccaagccc | 2220 |
| gccctcgcg ccggcggagc agaaggaggc aacccggcct tatgggacgt ggccttttcg | 2280 |
| gtgcaggtca aagtgacgaa cacgggttct cgggatggtc gtgccgttgc acagctctat | 2340 |
| gtggaattgc ccagtagcct ggggctggat acgccgtctc gacagctgcg gcagtttgag | 2400 |
| aagacgaaga tcttggctgc gggggagagt gaggtcctta cgttggatgt cacgcgcaag | 2460 |
| gatcttagtg cttgggatgt tgttgttcag gactggaagg cgcctgtgaa tggggaggga | 2520 |
| gttaagatct gggttggaga aagtgttgcg gatttgaggg ttgggtgtgt agtaggggag | 2580 |
| ggatgttcta ctttatag | 2598 |

<210> SEQ ID NO 18
<211> LENGTH: 2604
<212> TYPE: DNA
<213> ORGANISM: Artificial sequence
<220> FEATURE:
<223> OTHER INFORMATION: synthetic DNA

<400> SEQUENCE: 18

| | |
|---|---|
| atgcttttgc aagctttcct tttccttttg gctggttttg cagccaaaat atctgcagct | 60 |
| agcgaattcg agctcgagtc tctgacatca agagcctcta cagaagctta ctcccctcca | 120 |
| tattacccag ctccgaacgg aggatggata tccgaatggg ccagtgccta tgagaaggca | 180 |
| caccgtgtcg taagtaacat gaccttggcc gagaaggtga atctcacaag tggcaccggt | 240 |
| atctacatgg gaccttgtgc cggccagact ggcagtgttc ccgttttggg gatccccaac | 300 |
| ctgtgccttc atgattctcc tctcggagtc cgtaattcgg atcataatac ggcattcccg | 360 |
| gccggcatca cggtcggggc acatttgac aaggacctga tgtacgagcg cggagtcggt | 420 |
| ctaggcgaag aggcgcgggg aaagggtatc aacgttcttt tagggccgtc cgtgggccct | 480 |
| attgggcgga agccacgggg aggccgcaat tgggagggtt tcggagcgga tcccagttta | 540 |
| caggcctttg ggggctcgtt gaccattaaa ggaatgcaga gtacgggtgc tattgcttcg | 600 |
| ctcaaacatc ttatcggaaa cgaacaggag cagcatcgga tgagcagtgt tatcactcaa | 660 |
| ggctattcgt caaatatcga tgacaggact ttgcatgagc tgtatctgtg gccattcgcg | 720 |
| gaaagtgtaa gagccggtgc tggttcggtc atgattgcgt ataacgatgt gaacaggtcc | 780 |
| gcctgcagcc agaatagtaa gctcatcaat ggaatcctca aggacgagct ggggtttcag | 840 |
| ggctttgtcg tgaccgactg gttggctcat attggcggag tttcgtcagc gttggccggc | 900 |
| ctggacatga gcatgccggg tgacggagct atcccactct gggcacgag ttactgggcg | 960 |
| tgggagctgt cgcgctccgt gctcaatggc tcggtcccgg tcgagcgtct caatgacatg | 1020 |
| gtcacgcgaa tcgtcgcaac atggtacaaa atggggcagg acaaagacta tccgctacca | 1080 |
| aacttctcct caaacaccga ggatgagact gggccgttgt atcctggcgc cttatttttcc | 1140 |
| ccaagtggca ttgtcaacca atacgtcaat gtccaaggca accataatgt cacggcccgg | 1200 |
| gcaatcgcta gagatgcaat cacgttgcta aagaataacg acaatgtcct gcctctgaaa | 1260 |
| cggaatgcca gcttgaagat cttggcact gatgccgggg ccaattcgga cgggatcaat | 1320 |

```
tcttgcactg acaaaggctg caacaaaggc gtattgacca tgggctgggg aagcggaaca    1380
tccagactcc catatctcat tacgccgcaa gaagcgatag cgaatatctc atccaatgcc    1440
gaattccaca tcacggacac gtttcctttg ggcgtcaccg caggcctcga cgacattgcg    1500
atcgtcttca tcaattcgga ctccggcgag aactacatca ccgtcgatgg caatcctgga    1560
gaccgtacgc tggcagggct gaccgcatgg cacaacggcg acaaccttgt caaagctgct    1620
gcagaaaagt tctcaaacgt agtggttgta gtgcacaccg tgggacccat cctgatggaa    1680
gaatggatcg acctcgactc cgtcaaagcg gtgctcgtcg ctcacttacc cggacaggag    1740
gcaggctggt cactaaccga catcctcttt ggggactata gtcctagcgg ccatctgcct    1800
tacacaatcc ctcgcagtga atcagactac ccagagagcg tcggattgat tgctcagcca    1860
ttcggccaaa tccaagacga ctataccgaa ggcctctaca tcgattaccg ccacttccta    1920
aaagcaaaca tcaccccccg atacccattc ggacacggtc tctcctacac cacgttcaac    1980
ttcaccgaac caacctctc catcatcaaa cccctagaca cagcctaccc cgccgcgcga     2040
cccccctaaag gctccacacc cacataccc accaccaaac ccgccgcatc agaagtcgcc    2100
tggcccaaga acttcaaccg catctggcgc tacctctacc cctacctcga caacccggaa    2160
ggcgcagccg ccaactcctc aaagacatac ccttacccag acggctacac cacagagccc    2220
aagcccgccc ctcgcgccgg cggagcagaa ggaggcaacc cggccttatg ggacgtggcc    2280
tttttcggtgc aggtcaaagt gacgaacacg ggttctcggg atggtcgtgc cgttgcacag    2340
ctctatgtgg aattgcccag tagcctgggg ctggatacgc cgtctcgaca gctgcggcag    2400
tttgagaaga cgaagatctt ggctgcgggg gagagtgagg tccttacgtt ggatgtcacg    2460
cgcaaggatc ttagtgcttg ggatgttgtt gttcaggact ggaaggcgcc tgtgaatggg    2520
gagggagtta agatctgggt tggagaaagt gttgcggatt tgagggttgg gtgtgtagta    2580
ggggagggat gttctacttt atag                                           2604
```

<210> SEQ ID NO 19
<211> LENGTH: 2604
<212> TYPE: DNA
<213> ORGANISM: Artificial sequence
<220> FEATURE:
<223> OTHER INFORMATION: synthetic DNA

<400> SEQUENCE: 19

```
atgagatttc cttcaatttt tactgcagtt ttattcgcag catcctccgc attagctgct     60
agcgaattcg agctcgagtc tctgacatca agagcctcta cagaagctta ctcccctcca    120
tattacccag ctccgaacgg aggatggata tccgaatggg ccagtgccta tgagaaggca    180
caccgtgtcg taagtaacat gaccttggcc gagaaggtga atctcacaag tggcaccggt    240
atctacatgg gaccttgtgc cggccagact ggcagtgttc cccgttttgg gatccccaac    300
ctgtgccttc atgattctcc tctcggagtc cgtaattcgg atcataatac ggcattcccg    360
gccggcatca cggtcggggc cacatttgac aaggacctga tgtacgagcg cggagtcggt    420
ctaggcgaag aggcgcgggg aaagggtatc aacgttcttt tagggccgtc cgtgggccct    480
attgggcgga agccacgggg aggccgcaat tgggagggtt tcggagcgga tcccagttta    540
caggcctttg ggggctcgtt gaccattaaa ggaatgcaga gtacgggtgc tattgcttcg    600
ctcaaacatc ttatcggaaa cgaacaggag cagcatcgga tgagcagtgt tatcactcaa    660
ggctattcgt caaatatcga tgacaggact ttgcatgagc tgtatctgtg gccattcgcg    720
```

```
gaaagtgtaa gagccggtgc tggttcggtc atgattgcgt ataacgatgt gaacaggtcc    780
gcctgcagcc agaatagtaa gctcatcaat ggaatcctca aggacgagct ggggtttcag    840
ggctttgtcg tgaccgactg gttggctcat attggcggag tttcgtcagc gttggccggc    900
ctggacatga gcatgccggg tgacggagct atcccactct tgggcacgag ttactgggcg    960
tgggagctgt cgcgctccgt gctcaatggc tcggtcccgg tcgagcgtct caatgacatg   1020
gtcacgcgaa tcgtcgcaac atggtacaaa atggggcagg acaaagacta tccgctacca   1080
aacttctcct caaacaccga ggatgagact gggccgttgt atcctggcgc cttatttccc   1140
ccaagtggca ttgtcaacca atacgtcaat gtccaaggca accataatgt cacggcccgg   1200
gcaatcgcta gagatgcaat cacgttgcta aagaataacg acaatgtcct gcctctgaaa   1260
cggaatgcca gcttgaagat ctttggcact gatgccgggg ccaattcgga cgggatcaat   1320
tcttgcactg acaaaggctg caacaaaggc gtattgacca tgggctgggg aagcggaaca   1380
tccagactcc catatctcat tacgccgcaa gaagcgatag cgaatatctc atccaatgcc   1440
gaattccaca tcacggacac gtttcctttg ggcgtcaccg caggcctcga cgacattgcg   1500
atcgtcttca tcaattcgga ctccggcgag aactacatca ccgtcgatgg caatcctgga   1560
gaccgtacgc tggcagggct gaccgcatgg cacaacggcg acaaccttgt caaagctgct   1620
gcagaaaagt tctcaaacgt agtggttgta gtgcacaccg tgggacccat cctgatggaa   1680
gaatggatcg acctcgactc cgtcaaagcg gtgctcgtcg ctcacttacc cggacaggag   1740
gcaggctggt cactaaccga catcctcttt ggggactata gtcctagcgg ccatctgcct   1800
tacacaatcc ctcgcagtga atcagactac ccagagagcg tcggattgat tgctcagcca   1860
ttcggccaaa tccaagacga ctataccgaa ggcctctaca tcgattaccg ccacttccta   1920
aaagcaaaca tcacccccccg atacccattc ggacacggtc tctcctacac cacgttcaac   1980
ttcaccgaac ccaacctctc catcatcaaa cccctagaca cagcctaccc cgccgcgcga   2040 cccccctaaag gctccacacc cacatacccc accaccaaac ccgccgcatc agaagtcgcc   2100
tggcccaaga acttcaaccg catctggcgc tacctctacc cctacctcga caacccggaa   2160
ggcgcagccg ccaactcctc aaagacatac ccttacccag acggctacac cacagagccc   2220
aagcccgccc ctcgcgccgg cggagcagaa ggaggcaacc cggccttatg ggacgtggcc   2280 tttttcggtgc aggtcaaagt gacgaacacg ggttctcggg atggtcgtgc cgttgcacag   2340
ctctatgtgg aattgcccag tagcctgggg ctggatacgc cgtctcgaca gctgcggcag   2400
tttgagaaga cgaagatctt ggctgcgggg gagagtgagg tccttacgtt ggatgtcacg   2460
cgcaaggatc ttagtgcttg ggatgttgtt gttcaggact ggaaggcgcc tgtgaatggg   2520
gagggagtta agatctgggt tggagaaagt gttgcggatt tgagggttgg gtgtgtagta   2580
ggggagggat gttctacttt atag                                           2604
```

<210> SEQ ID NO 20
<211> LENGTH: 2613
<212> TYPE: DNA
<213> ORGANISM: Artificial sequence
<220> FEATURE:
<223> OTHER INFORMATION: synthetic DNA

<400> SEQUENCE: 20

```
atgtttaaat ctgttgttta ttcaattta gccgcttctt tggccaatgc agctagcgaa       60
ttcgagctcg gtaccggggg atctaaggat gatctcgcgt actcccctcc tttctaccct      120
tccccatggg cagatggtca gggtgaatgg gcggaagtat acaaacgcgc tgtagacata      180
```

```
gtttcccaga tgacgttgac agagaaagtc aacttaacga ctggaacagg atggcaacta    240
gagaggtgtg ttggacaaac tggcagtgtt cccagactca acatcccag cttgtgtttg     300 caggatagtc ctcttggtat tcgtttctcg gactacaatt cagctttccc tgcgggtgtt    360
aatgtcgctg ccacctggga caagacgctc gcctaccttc gtggtcaggc aatgggtgag    420
gagttcagtg ataagggtat tgacgttcag ctgggtcctg ctgctggccc tctcggtgct    480
catccggatg gcgtagaaa ctgggaaggt ttctcaccag atccagccct caccggtgta     540 cttttttgcgg agacgattaa gggtattcaa gatgctggtg tcattgcgac agctaagcat   600
tatatcatga acgaacaaga gcatttccgc caacaacccg aggctgcggg ttacggattc    660
aacgtaagcg acagtttgag ttccaacgtt gatgacaaga ctatgcatga attgtacctc    720
tggcccttcg cggatgcagt acgcgctgga gtcggtgctg tcatgtgctc ttacaaccaa    780
atcaacaaca gctacggttg cgagaatagc gaaactctga caagctttt gaaggcggag     840 cttggttttcc aaggcttcgt catgagtgat tggaccgctc atcacagcgg cgtaggcgct   900
gctttagcag gtctggatat gtcgatgccc ggtgatgtta ccttcgatag tggtacgtct    960 ttctgggggtg caaacttgac ggtcggtgtc cttaacggta caatccccca atggcgtgtt   1020
gatgacatgg ctgtccgtat catggccgct tattacaagg ttggccgcga caccaaatac    1080
acccctccca acttcagctc gtggaccagg gacgaatatg gtttcgcgca taaccatgtt    1140
tcggagggtg cttacgagag ggtcaacgaa ttcgtggacg tgcaacgcga tcatgccgac    1200
ctaatccgtc gcatcggcgc gcagagcact gttctgctga agaacaaggg tgccttgccc    1260
ttgagccgca aggaaaagct ggtcgccctt ctgggagagg atgcgggttc caactcgtgg    1320
ggcgctaacg gctgtgatga ccgtggttgc gataacggta cccttgccat ggcctggggt    1380
agcggtactg cgaatttccc ataccctgtg acaccagagc aggcgattca gaacgaagtt    1440
cttcagggcc gtggtaatgt cttcgccgtg accgacagtt gggcgctcga caagatcgct    1500
gcggctgccc gccaggccag cgtatctctc gtgttcgtca actccgactc aggagaaggc    1560
tatcttagtg tggatggaaa tgagggcgat cgtaacaaca tcactctgtg gaagaacggc    1620
gacaatgtgg tcaagaccgc agcgaataac tgtaacaaca ccgttgtcat catccactcc    1680
gtcggaccag ttttgatcga tgaatggtat gaccaccca atgtcactgg tattctctgg     1740
gctggtctgc caggccagga gtctggtaac tccattgccg atgtgctgta cggtcgtgtc    1800
aaccctggcg ccaagtctcc tttcacttgg ggcaagaccc gggagtcgta tggttctccc   1860
ttggtcaagg atgccaacaa tggcaacgga gcgccccagt ctgatttcac ccagggtgtt    1920
ttcatcgatt accgccattt cgataagttc aatgagaccc ctatctacga gtttggctac    1980
ggcttgagct acaccaccctt cgagctctcc gacctccatg ttcagcccct gaacgcgtcc   2040
cgatacactc ccaccagtgg catgactgaa gctgcaaaga actttggtga aattggcgat    2100
gcgtcggagt acgtgtatcc ggaggggctg gaaaggatcc atgagtttat ctatccctgg    2160
atcaactcta ccgacctgaa ggcatcgtct gacgattcta actacggctg ggaagactcc    2220
aagtatattc ccgaaggcgc cacggatggg tctgcccagc ccgttggcc cgctagtggt     2280 ggtgccggag gaaaccccgg tctgtacgag gatctttttcc gcgtctctgt gaaggtcaag   2340
aacacgggca atgtcgccgg tgatgaagtt cctcagctgt acgtttccct aggcggcccg    2400
aatgagccca aggtggtact gcgcaagttt gagcgtattc acttggcccc ttcgcaggag    2460
gccgtgtgga caacgaccct tacccgtcgt gaccttgcaa actgggacgt ttcggctcag   2520
```

```
gactggaccg tcactcctta ccccaagacg atctacgttg gaaactcctc acggaaactg   2580
ccgctccagg cctcgctgcc taaggcccag taa                                2613

<210> SEQ ID NO 21
<211> LENGTH: 2619
<212> TYPE: DNA
<213> ORGANISM: Artificial sequence
<220> FEATURE:
<223> OTHER INFORMATION: synthetic DNA

<400> SEQUENCE: 21
atgcttttgc aagctttcct tttccttttg gctggttttg cagccaaaat atctgcagct     60
agcgaattcg agctcggtac ccggggatct aaggatgatc tcgcgtactc ccctcctttc    120
tacccttccc catgggcaga tggtcagggt gaatgggcgg aagtatacaa acgcgctgta    180
gacatagttt cccagatgac gttgacagag aaagtcaact taacgactgg aacaggatgg    240
caactagaga ggtgtgttgg acaaactggc agtgttccca gactcaacat ccccagcttg    300
tgtttgcagg atagtcctct tggtattcgt ttctcggact acaattcagc tttccctgcg    360
ggtgttaatg tcgctgccac ctgggacaag acgctcgcct accttcgtgg tcaggcaatg    420
ggtgaggagt tcagtgataa gggtattgac gttcagctgg gtcctgctgc tggccctctc    480
ggtgctcatc cggatggcgg tagaaactgg gaaggtttct caccagatcc agccctcacc    540
ggtgtacttt ttgcggagac gattaagggt attcaagatg ctggtgtcat tgcgacagct    600
aagcattata tcatgaacga acaagagcat ttccgccaac aacccgaggc tgcgggttac    660
ggattcaacg taagcgacag tttgagttcc aacgttgatg caagactat gcatgaattg     720 tacctctggc ccttcgcgga tgcagtacgc gctggagtcg gtgctgtcat gtgctcttac    780
aaccaaatca caacagcta cggttgcgag aatagcgaaa ctctgaacaa gcttttgaag    840
gcggagcttg gtttccaagg cttcgtcatg agtgattgga ccgctcatca cagcggcgta    900
ggcgctgctt tagcaggtct ggatatgtcg atgcccggtg atgttacctt cgatagtggt    960
acgtctttct ggggtgcaaa cttgacggtc ggtgtcctta acggtacaat cccccaatgg   1020
cgtgttgatg acatggctgt ccgtatcatg gccgcttatt acaaggttgg ccgcgacacc   1080
aaatacaccc ctcccaactt cagctcgtgg accagggacg aatatggttt cgcgcataac   1140
catgtttcgg agggtgctta cgagagggtc aacgaattcg tggacgtgca acgcgatcat   1200
gccgacctaa tccgtcgcat cggcgcgcag agcactgttc tgctgaagaa caagggtgcc   1260
ttgcccttga ccgcaagga aaagctggtc gcccttctgg gagaggatgc gggttccaac    1320
tcgtggggcg ctaacggctg tgatgaccgt ggttgcgata acggtaccct tgccatggcc   1380
tggggtagcg gtactgcgaa tttcccatac ctcgtgacac cagagcaggc gattcagaac   1440
gaagttcttc agggccgtgg taatgtcttc gccgtgaccg acagttgggc gctcgacaag   1500
atcgctgcgg ctgcccgcca ggccagcgta tctctcgtgt tcgtcaactc cgactcagga   1560
gaaggctatc ttagtgtgga tggaaatgag ggcgatcgta caacatcac tctgtggaag    1620 aacggcgaca atgtggtcaa gaccgcagcg aataactgta acaacaccgt tgtcatcatc   1680
cactccgtcg gaccagtttt gatcgatgaa tggtatgacc accccaatgt cactggtatt   1740
ctctgggctg gtctgccagg ccaggagtct ggtaactcca ttgccgatgt gctgtacggt   1800
cgtgtcaacc ctggcgccaa gtctcctttc acttggggca agaccccgga gtcgtatggt   1860
tctcccttgg tcaaggatgc caacaatggc aacggagcgc cccagtctga tttcacccag   1920
ggtgttttca tcgattaccg ccatttcgat aagttcaatg agacccctat ctacgagttt   1980
```

```
ggctacggct tgagctacac caccttcgag ctctccgacc tccatgttca gcccctgaac    2040
gcgtcccgat acactcccac cagtggcatg actgaagctg caaagaactt tggtgaaatt    2100
ggcgatgcgt cggagtacgt gtatccggag gggctggaaa ggatccatga gtttatctat    2160
ccctggatca actctaccga cctgaaggca tcgtctgacg attctaacta cggctgggaa    2220
gactccaagt atattcccga aggcgccacg gatgggtctg cccagccccg tttgcccgct    2280
agtggtggtg ccggaggaaa ccccggtctg tacgaggatc ttttccgcgt ctctgtgaag    2340
gtcaagaaca cgggcaatgt cgccggtgat gaagttcctc agctgtacgt ttccctaggc    2400
ggcccgaatg agcccaaggt ggtactgcgc aagtttgagc gtattcactt ggccccttcg    2460
caggaggccg tgtggacaac gacccttacc cgtcgtgacc ttgcaaactg gacgtttcg    2520 gctcaggact ggaccgtcac tccttacccc aagacgatct acgttggaaa ctcctcacgg    2580
aaactgccgc tccaggcctc gctgcctaag gcccagtaa                          2619

<210> SEQ ID NO 22
<211> LENGTH: 2619
<212> TYPE: DNA
<213> ORGANISM: Artificial sequence
<220> FEATURE:
<223> OTHER INFORMATION: synthetic DNA

<400> SEQUENCE: 22
atgagatttc cttcaatttt tactgcagtt ttattcgcag catcctccgc attagctgct      60
agcgaattcg agctcggtac ccggggatct aaggatgatc tcgcgtactc ccctcctttc     120 taccctteec catgggcaga tggtcagggt gaatgggcgg aagtatacaa acgcgctgta     180
gacatagttt cccagatgac gttgacagag aaagtcaact taacgactgg aacaggatgg     240
caactagaga ggtgtgttgg acaaactggc agtgttccca gactcaacat ccccagcttg     300
tgtttgcagg atagtcctct tggtattcgt ttctcggact acaattcagc tttccctgcg     360
ggtgttaatg tcgctgccac ctgggacaag acgctcgcct accttcgtgg tcaggcaatg     420
ggtgaggagt tcagtgataa gggtattgac gttcagctgg gtcctgctgc tggccctctc     480
ggtgctcatc cggatggcgg tagaaactgg gaaggtttct caccagatcc agccctcacc     540
ggtgtacttt ttgcggagac gattaagggt attcaagatg ctggtgtcat tgcgacagct     600
aagcattata tcatgaacga acaagagcat ttccgccaac aacccgaggc tgcgggttac     660
ggattcaacg taagcgacag tttgagttcc aacgttgatg acaagactat gcatgaattg     720
tacctctggc ccttcgcgga tgcagtacgc gctggagtcg tgctgtcat gtgctcttac     780 aaccaaatca caacagcta cggttgcgag aatagcgaaa ctctgaacaa gcttttgaag     840
gcggagcttg gttccaagg cttcgtcatg agtgattgga ccgctcatca cagcggcgta     900
ggcgctgctt tagcaggtct ggatatgtcg atgcccggtg atgttacctt cgatagtggt     960
acgtctttct ggggtgcaaa cttgacggtc ggtgtcctta acggtacaat ccccaatgg    1020 cgtgttgatg acatggctgt ccgtatcatg gccgcttatt acaaggttgg ccgcgacacc    1080
aaatacaccc ctcccaactt cagctcgtgg accaggacg aatatggttt cgcgcataac    1140
catgtttcgg agggtgctta cgagagggtc aacgaattcg tggacgtgca acgcgatcat    1200
gccgacctaa tcgtcgcat cggcgcgcag agcactgttc tgctgaagaa caagggtgcc    1260
ttgcccttga gccgcaagga aaagctggtc gcccttctgg agaggatgc gggttccaac    1320 tcgtggggcg ctaacggctg tgatgaccgt ggttgcgata acggtaccct tgccatggcc    1380
```

```
tggggtagcg gtactgcgaa tttcccatac ctcgtgacac cagagcaggc gattcagaac   1440
gaagttcttc agggccgtgg taatgtcttc gccgtgaccg acagttgggc gctcgacaag   1500
atcgctgcgg ctgcccgcca ggccagcgta tctctcgtgt tcgtcaactc cgactcagga   1560
gaaggctatc ttagtgtgga tggaaatgag ggcgatcgta caacatcac tctgtggaag    1620 aacggcgaca atgtggtcaa gaccgcagcg aataactgta caacaccgt tgtcatcatc    1680 cactccgtcg gaccagtttt gatcgatgaa tggtatgacc accccaatgt cactggtatt   1740
ctctgggctg gtctgccagg ccaggagtct ggtaactcca ttgccgatgt gctgtacggt   1800
cgtgtcaacc ctggcgccaa gtctcctttc acttggggca agacccggga gtcgtatggt   1860
tctcccttgg tcaaggatgc caacaatggc aacggagcgc cccagtctga tttcacccag   1920
ggtgttttca tcgattaccg ccatttcgat aagttcaatg agaccccctat ctacgagttt   1980 ggctacggct tgagctacac caccttcgag ctctccgacc tccatgttca gcccctgaac   2040
gcgtcccgat acactcccac cagtggcatg actgaagctg caaagaactt tggtgaaatt   2100
ggcgatgcgt cggagtacgt gtatccggag gggctggaaa ggatccatga gtttatctat   2160
ccctggatca actctaccga cctgaaggca tcgtctgacg attctaacta cggctgggaa   2220
gactccaagt atattcccga aggcgccacg gatgggtctg cccagccccg tttgcccgct   2280
agtggtggtg ccggaggaaa ccccggtctg tacgaggatc ttttccgcgt ctctgtgaag   2340
gtcaagaaca cgggcaatgt cgccggtgat gaagttcctc agctgtacgt ttccctaggc   2400
ggcccgaatg agcccaaggt ggtactgcgc aagtttgagc gtattcactt ggccccttcg   2460
caggaggccg tgtggacaac gacccttacc cgtcgtgacc ttgcaaactg gacgtttcg    2520 gctcaggact ggaccgtcac tccttacccc aagacgatct acgttggaaa ctcctcacgg   2580
aaactgccgc tccaggcctc gctgcctaag gcccagtaa                          2619
```

<210> SEQ ID NO 23
<211> LENGTH: 2613
<212> TYPE: DNA
<213> ORGANISM: Artificial sequence
<220> FEATURE:
<223> OTHER INFORMATION: synthetic DNA

<400> SEQUENCE: 23

```
atgtttaaat ctgttgttta ttcaattta gccgcttctt tggccaatgc agctagcgaa     60
ttcgagctcg gtacccgggg atctaaggat gatctcgcgt actcccctcc tttctaccct   120
tccccgtggg cagatggtca gggtgaatgg gcggaagtat acaaacgcgc tgtagacata   180
gtttcccaga tgacgttgac agagaaagtc aacttaacga ctggaacagg atggcagcta   240
gagaggtgtg ttggacaaac tggcagtgtt cccagactca acatcccag cttgtgcttg    300 caggatagtc tcttggtat tcgtttctcg gactataatt cggctttccc tgcgggtgtt    360
aatgtcgctg ccacttggga caagacgctc gcctacctcc gcggtcaggc aatgggtgaa   420
gagttcagtg acaagggcat tgacgttcag ctgggtcctg ctgctggccc tctcggtgct   480
catccggacg gcggtagaaa ctgggaaggg ttctcaccag atccagccct caccggtgta   540
ctgtttgcag agacgattaa gggtatccaa gatgctggtg tcattgcgac agctaagcat   600
tatatcatga acgaacaaga gcatttccgc caacaacccg aggctgcggg ttacggattc   660
aacgtaagcg acagtttgag ctccaacgtt gatgacaaga ctatccatga attatacctc   720
tggcccttcg cggatgcagt acgcgctgga gtcggtgctc tcatgtgctc ttacaaccaa   780
atcaacaaca gctacggttg cgagaatagc gaaactctga caagcttttt gaaggcggaa   840
```

```
cttggtttcc aaggcttcgt catgagtgat tggaccgctc atcacagcgg tgtaggcgct    900
gctttagcag gtatggatat gtcgatgccc ggtgatgtta ccttcgatag tggtacgtct    960
ttctggggtg caaacttgac ggtcggtgtc cttaacggta caatccccca atggcgcgtt   1020
gatgacatgg ctgtccgtat catggccgct tattacaagg ttggccgcga caccaagtac   1080
actcctccca acttcagctc gtggaccagg gacgaatatg gtttcgcgca taaccatgtt   1140
tcggaaggtg cttacgagag ggtcaacgaa ttcgtggacg tgcaacgcga tcatgccgac   1200
ctgatccgtc gcatcggcgc gcagagcact gttctgctga agaacaaggg tgccttgccc   1260
ttgagccgca aggaaaagct ggtcgccctt ctgggagagg atgcgggttc caactcgtgg   1320
ggcgctaacg gctgtgatga ccgtggatgc gataacggta cccttgccat ggcctggggt   1380
agcggtactc gaatttccc ataccctcgtg acaccggagc aggcgattca gaacgaagtt   1440
cttcagggcc gtggtaatgt cttcgccgtg accgacagct gggcactcga caagatcgct   1500
gcggctgccc gccaggccag cgtatccctc gtattcgtca actccgactc gggagaaggc   1560
tatcttagtg tggatggaaa tgagggcgat cgcaacaata tcactctgtg aagaacggt   1620
gacaatgtgg tcaagaccgc ggcgaataac tgtaacaaca ccgttgtcat catccactcc   1680
gtcggaccag ttttgatcaa tgaatggtat gaccacccta atgtcaccgg tattctctgg   1740
gctggtctgc caggccagga gtctggtaac tccattgccg atgtgctgta cggtcgtgtc   1800
aaccctggtg ccaagtctcc tttcacttgg ggcaagactc gggattcgta cggttctccc   1860
ttggtcaagg atgccaacaa tggtaacgga gcgccccagt ctgatttcac ccagggtgtt   1920
ttcatcgatt accgccattt cgataagttc aatgagaccc ctatctacga gtttggctac   1980
ggcttgagct acaccacctt cgaactctcc gacctccatg ttcagcccct gaacgcgtcc   2040
caatacactc ccaccagtgg catgactgaa gctgcaaaga actttggtga aattggcgat   2100
gcgtcggagt acgtgtatcc ggaggggctg gagaggatcc atgagtttat ctatccctgg   2160
attaactcta ccgacctgaa ggcatcgtct gacgattcta actacggctg ggaagactcc   2220
gagtacatcc ccgaaggcgc cacggatggg tctgcccagc ccgtttgcc cgctagcggt   2280
ggtgccggag gaaaccccgg tctgtatgag gatcttttcc gcgtctctgt gaaggtcaag   2340
aacacgggca atgtcgccgg tgatgaagtt cctcagctgt acgtttccct aggcggcccg   2400
aatgagccca aggtggtgct gcgcaagttt gagcgtattc acttggcccc ttcgcaggag   2460
gtcgtgtgga caacgaccct tacccgtcgt gaccttgcca actgggacgt tcggctcag   2520
gactgggccg tcactcctta ccccaagacg atctacgttg gaaactcctc acggaaactg   2580
cccctccagg tctcgctgcc taaggcccag taa                                 2613

<210> SEQ ID NO 24
<211> LENGTH: 2619
<212> TYPE: DNA
<213> ORGANISM: Artificial sequence
<220> FEATURE:
<223> OTHER INFORMATION: synthetic DNA

<400> SEQUENCE: 24
atgcttttgc aagctttcct tttccttttg gctggttttg cagccaaaat atctgcagct     60
agcgaattcg agctcggtac ccggggatct aaggatgatc tcgcgtactc ccctcctttc    120
tacccttccc cgtgggcaga tggtcagggt gaatgggcgg aagtatacaa acgcgctgta    180
gacatagttt cccagatgac gttgacagag aaagtcaact taacgactgg aacaggatgg    240
```

```
cagctagaga ggtgtgttgg acaaactggc agtgttccca gactcaacat ccccagcttg    300
tgcttgcagg atagtcctct tggtattcgt ttctcggact ataattcggc tttccctgcg    360
ggtgttaatg tcgctgccac ttgggacaag acgctcgcct acctccgcgg tcaggcaatg    420
ggtgaagagt tcagtgacaa gggcattgac gttcagctgg gtcctgctgc tggccctctc    480
ggtgctcatc cggacggcgg tagaaactgg gaagggttct caccagatcc agccctcacc    540
ggtgtactgt ttgcagagac gattaagggt atccaagatg ctggtgtcat tgcgacagct    600
aagcattata tcatgaacga acaagagcat ttccgccaac aacccgaggc tgcgggttac    660
ggattcaacg taagcgacag tttgagctcc aacgttgatg acaagactat ccatgaatta    720
tacctctggc ccttcgcgga tgcagtacgc gctggagtcg gtgctgtcat gtgctcttac    780
aaccaaatca acaacagcta cggttgcgag aatagcgaaa ctctgaacaa gcttttgaag    840
gcggaacttg gtttccaagg cttcgtcatg agtgattgga ccgctcatca cagcggtgta    900
ggcgctgctt tagcaggtat ggatatgtcg atgcccggtg atgttacctt cgatagtggt    960
acgtcttcct gggtgcaaa cttgacggtc ggtgtcctta cggtacaat cccccaatgg   1020
cgcgttgatg acatggctgt ccgtatcatg gccgcttatt acaaggttgg ccgcgacacc   1080
aagtacactc ctcccaactt cagctcgtgg accagggacg aatatggttt cgcgcataac   1140
catgtttcgg aaggtgctta cgagagggtc aacgaattcg tggacgtgca acgcgatcat   1200
gccgacctga tccgtcgcat cggcgcgcag agcactgttc tgctgaagaa caagggtgcc   1260
ttgcccttga gccgcaagga aaagctggtc gcccttctgg agaggatgc gggttccaac   1320
tcgtggggcg ctaacggctg tgatgaccgt ggatgcgata acgtaccct gccatggcc    1380
tggggtagcg gtactgcgaa tttcccatac ctcgtgacac cggagcaggc gattcagaac   1440
gaagttcttc agggccgtgg taatgtcttc gccgtgaccg acagctgggc actcgacaag   1500
atcgctgcgg ctgcccgcca ggccagcgta tccctcgtat tcgtcaactc cgactcggga   1560
gaaggctatc ttagtgtgga tggaaatgag ggcgatcgca acaatatcac tctgtggaag   1620
aacggtgaca atgtggtcaa gaccgcggcg aataactgta acaacaccgt tgtcatcatc   1680
cactccgtcg gaccagtttt gatcaatgaa tggtatgacc accctaatgt caccggtatt   1740
ctctgggctg gtctgccagg ccaggagtct ggtaactcca ttgccgatgt gctgtacggt   1800
cgtgtcaacc ctggtgccaa gtctcctttc acttggggca agactcggga ttcgtacggt   1860
tctcccttgg tcaaggatgc caacaatggt aacggagcgc cccagtctga tttcacccag   1920
ggtgttttca tcgattaccg ccatttcgat aagttcaatg agaccccctat ctacgagttt   1980
ggctacggct tgagctacac caccttcgaa ctctccgacc tccatgttca gcccctgaac   2040
gcgtcccaat acactcccac cagtggcatg actgaagctg caaagaactt tggtgaaatt   2100
ggcgatgcgt cggagtacgt gtatccggag gggctggaga ggatccatga gttttatctat   2160
ccctggatta actctaccga cctgaaggca tcgtctgacg attctaacta cggctgggaa   2220
gactccgagt acatccccga aggcgccacg gatgggtctg cccagccccg tttgcccgct   2280
agcggtggtg ccggaggaaa ccccggtctg tatgaggatc ttttccgcgt ctctgtgaag   2340
gtcaagaaca cggcaatgt cgccggtgat gaagttcctc agctgtacgt ttccctaggc   2400
ggcccgaatg agcccaaggt ggtgctgcgc aagtttgagc gtattcactt ggccccttcg   2460
caggaggtcg tgtggacaac gacccttacc cgtcgtgacc ttgccaactg ggacgtttcg   2520
gctcaggact gggccgtcac tccttacccc aagacgatct acgttggaaa ctcctcacgg   2580
aaactgcccc tccaggtctc gctgcctaag gcccagtaa                          2619
```

<210> SEQ ID NO 25
<211> LENGTH: 2619
<212> TYPE: DNA
<213> ORGANISM: Artificial sequence
<220> FEATURE:
<223> OTHER INFORMATION: synthetic DNA

<400> SEQUENCE: 25

```
atgagatttc cttcaatttt tactgcagtt ttattcgcag catcctccgc attagctgct      60
agcgaattcg agctcggtac ccggggatct aaggatgatc tcgcgtactc ccctcctttc     120
tacccttccc cgtgggcaga tggtcagggt gaatgggcgg aagtatacaa acgcgctgta     180
gacatagttt cccagatgac gttgacagag aaagtcaact taacgactgg aacaggatgg     240
cagctagaga ggtgtgttgg acaaactggc agtgttccca gactcaacat ccccagcttg     300
tgcttgcagg atagtcctct tggtattcgt ttctcggact ataattcggc tttccctgcg     360
ggtgttaatg tcgctgccac ttgggacaag acgctcgcct acctccgcgg tcaggcaatg     420
ggtgaagagt tcagtgacaa gggcattgac gttcagctgg gtcctgctgc tggccctctc     480
ggtgctcatc cggacggcgg tagaaactgg gaagggttct caccagatcc agccctcacc     540
ggtgtactgt ttgcagagac gattaagggt atccaagatg ctggtgtcat tgcgacagct     600
aagcattata tcatgaacga acaagagcat ttccgccaac aacccgaggc tgcgggttac     660
ggattcaacg taagcgacag tttgagctcc aacgttgatg acaagactat ccatgaatta     720
tacctctggc ccttcgcgga tgcagtacgc gctggagtcg gtgctgtcat gtgctcttac     780
aaccaaatca caacagcta cggttgcgag aatagcgaaa ctctgaacaa gcttttgaag     840
gcggaacttg gtttccaagg cttcgtcatg agtgattgga ccgctcatca cagcggtgta     900
ggcgctgctt tagcaggtat ggatatgtcg atgcccggtg atgttacctt cgatagtggt     960
acgtctttct ggggtgcaaa cttgacggtc ggtgtcctta acggtacaat cccccaatgg    1020
cgcgttgatg acatggctgt ccgtatcatg gccgcttatt acaaggttgg ccgcgacacc    1080
aagtacactc ctcccaactt cagctcgtgg accaggacg aatatggttt cgcgcataac    1140
catgtttcgg aaggtgctta cgagagggtc aacgaattcg tggacgtgca acgcgatcat    1200
gccgacctga tccgtcgcat cggcgcgcag agcactgttc tgctgaagaa caagggtgcc    1260
ttgcccttga gccgcaagga aaagctggtc gcccttctgg agaggatgc gggttccaac    1320
tcgtggggcg ctaacggctg tgatgaccgt ggatgcgata acggtaccct tgccatggcc    1380
tggggtagcg gtactgcgaa tttcccatac ctcgtgacac cggagcaggc gattcagaac    1440
gaagttcttc agggccgtgg taatgtcttc gccgtgaccg acagctgggc actcgacaag    1500
atcgctgcgc tgcccgcca ggccagcgta tccctcgtat tcgtcaactc cgactcggga    1560
gaaggctatc ttagtgtgga tggaaatgag ggcgatcgca acaatatcac tctgtggaag    1620
aacggtgaca atgtggtcaa gaccgcggcg aataactgta acaacaccgt tgtcatcatc    1680
cactccgtcg gaccagtttt gatcaatgaa tggtatgacc accctaatgt caccggtatt    1740
ctctgggctg gtctgccagg ccaggagtct ggtaactcca ttgccgatgt gctgtacggt    1800
cgtgtcaacc ctggtgccaa gtctcctttc acttggggca agactcggga ttcgtacggt    1860
tctcccttgg tcaaggatgc caacaatggt aacggagcgc cccagtctga tttcacccag    1920
ggtgttttca tcgattaccg ccatttcgat aagttcaatg agaccccctat ctacgagttt    1980
ggctacggct tgagctacac caccttcgaa ctctccgacc tccatgttca gccccctgaac    2040
```

```
gcgtcccaat acactcccac cagtggcatg actgaagctg caaagaactt tggtgaaatt    2100
ggcgatgcgt cggagtacgt gtatccggag gggctggaga ggatccatga gtttatctat    2160
ccctggatta actctaccga cctgaaggca tcgtctgacg attctaacta cggctgggaa    2220
gactccgagt catccccga aggcgccacg gatgggtctg cccagcccg tttgcccgct      2280 agcggtggtg ccggaggaaa ccccggtctg tatgaggatc ttttccgcgt ctctgtgaag    2340
gtcaagaaca cgggcaatgt cgccggtgat gaagttcctc agctgtacgt ttccctaggc    2400
ggcccgaatg agcccaaggt ggtgctgcgc aagtttgagc gtattcactt ggcccttcg     2460 caggaggtcg tgtggacaac gaccttaccc cgtcgtgacc ttgccaactg ggacgtttcg    2520
gctcaggact gggccgtcac tccttacccc aagacgatct acgttggaaa ctcctcacgg    2580
aaactgcccc tccaggtctc gctgcctaag gcccagtaa                           2619
```

```
<210> SEQ ID NO 26
<211> LENGTH: 28
<212> TYPE: DNA
<213> ORGANISM: Artificial sequence
<220> FEATURE:
<223> OTHER INFORMATION: synthetic DNA

<400> SEQUENCE: 26
gcggccgcat ggctgccttc ccggccta                                         28

<210> SEQ ID NO 27
<211> LENGTH: 34
<212> TYPE: DNA
<213> ORGANISM: Artificial sequence
<220> FEATURE:
<223> OTHER INFORMATION: synthetic DNA

<400> SEQUENCE: 27
gtcgacctac aaagtagaac atccctctcc aacc                                  34

<210> SEQ ID NO 28
<211> LENGTH: 29
<212> TYPE: DNA
<213> ORGANISM: Artificial sequence
<220> FEATURE:
<223> OTHER INFORMATION: synthetic DNA

<400> SEQUENCE: 28
gcggccgcat ggctgccttt ccggcctac                                        29

<210> SEQ ID NO 29
<211> LENGTH: 34
<212> TYPE: DNA
<213> ORGANISM: Artificial sequence
<220> FEATURE:
<223> OTHER INFORMATION: synthetic DNA

<400> SEQUENCE: 29
gtcgacctat aaagtagaac atccctcccc tact                                  34

<210> SEQ ID NO 30
<211> LENGTH: 29
<212> TYPE: DNA
<213> ORGANISM: Artificial sequence
<220> FEATURE:
<223> OTHER INFORMATION: synthetic DNA

<400> SEQUENCE: 30
agatctatga agcttggttg gatcgaggt                                        29
```

<210> SEQ ID NO 31
<211> LENGTH: 27
<212> TYPE: DNA
<213> ORGANISM: Artificial sequence
<220> FEATURE:
<223> OTHER INFORMATION: synthetic DNA

<400> SEQUENCE: 31
gtcgacttac tgggccttag gcagcga                                27

<210> SEQ ID NO 32
<211> LENGTH: 19
<212> TYPE: DNA
<213> ORGANISM: Artificial sequence
<220> FEATURE:
<223> OTHER INFORMATION: synthetic DNA

<400> SEQUENCE: 32
aattaattaa gagctagcg                                         19

<210> SEQ ID NO 33
<211> LENGTH: 19
<212> TYPE: DNA
<213> ORGANISM: Artificial sequence
<220> FEATURE:
<223> OTHER INFORMATION: synthetic DNA

<400> SEQUENCE: 33
ttaattctcg atcgcttaa                                         19

<210> SEQ ID NO 34
<211> LENGTH: 37
<212> TYPE: DNA
<213> ORGANISM: Artificial sequence
<220> FEATURE:
<223> OTHER INFORMATION: synthetic DNA

<400> SEQUENCE: 34
aagagctcga gtctctgaca tcaagagcct ctacaga                     37

<210> SEQ ID NO 35
<211> LENGTH: 40
<212> TYPE: DNA
<213> ORGANISM: Artificial sequence
<220> FEATURE:
<223> OTHER INFORMATION: synthetic DNA

<400> SEQUENCE: 35
gggtcgacct ataaagtaga acatccctcc cctactacac                  40

<210> SEQ ID NO 36
<211> LENGTH: 31
<212> TYPE: DNA
<213> ORGANISM: Artificial sequence
<220> FEATURE:
<223> OTHER INFORMATION: synthetic DNA

<400> SEQUENCE: 36
taagatctaa ggatgatctc gcgtactccc c                           31

<210> SEQ ID NO 37
<211> LENGTH: 55
<212> TYPE: DNA
<213> ORGANISM: Artificial sequence
<220> FEATURE:

<223> OTHER INFORMATION: synthetic DNA

<400> SEQUENCE: 37
taaatgttta aatctgttgt ttattcaatt ttagccgctt ctttggccaa tgcag    55

<210> SEQ ID NO 38
<211> LENGTH: 61
<212> TYPE: DNA
<213> ORGANISM: Artificial sequence
<220> FEATURE:
<223> OTHER INFORMATION: synthetic DNA

<400> SEQUENCE: 38
ctagctgcat tggccaaaga agcggctaaa attgaataaa caacagattt aaacatttaa    60
t    61

<210> SEQ ID NO 39
<211> LENGTH: 61
<212> TYPE: DNA
<213> ORGANISM: Artificial sequence
<220> FEATURE:
<223> OTHER INFORMATION: synthetic DNA

<400> SEQUENCE: 39
taaatgcttt tgcaagcttt cctttttcctt ttggctggtt ttgcagccaa aatatctgca    60
g    61

<210> SEQ ID NO 40
<211> LENGTH: 61
<212> TYPE: DNA
<213> ORGANISM: Artificial sequence
<220> FEATURE:
<223> OTHER INFORMATION: synthetic DNA

<400> SEQUENCE: 40
taaatgagat ttccttcaat ttttactgca gttttattcg cagcatcctc cgcattagct    60
g    61

<210> SEQ ID NO 41
<211> LENGTH: 61
<212> TYPE: DNA
<213> ORGANISM: Artificial sequence
<220> FEATURE:
<223> OTHER INFORMATION: synthetic DNA

<400> SEQUENCE: 41
taaatgagat ttccttcaat ttttactgca gttttattcg cagcatcctc cgcattagct    60
g    61

<210> SEQ ID NO 42
<211> LENGTH: 67
<212> TYPE: DNA
<213> ORGANISM: Artificial sequence
<220> FEATURE:
<223> OTHER INFORMATION: synthetic DNA

<400> SEQUENCE: 42
ctagcagcta atgcggagga tgctgcgaat aaaactgcag taaaaattga aggaaatctc    60
atttaat    67

<210> SEQ ID NO 43
<211> LENGTH: 57

<212> TYPE: DNA
<213> ORGANISM: Saccharomyces cerevisiae
<220> FEATURE:
<221> NAME/KEY: CDS
<222> LOCATION: (1)..(57)

<400> SEQUENCE: 43

```
atg aga ttt cct tca att ttt act gca gtt tta ttc gca gca tcc tcc      48
Met Arg Phe Pro Ser Ile Phe Thr Ala Val Leu Phe Ala Ala Ser Ser
1               5                   10                  15 gca tta gct                                                          57
Ala Leu Ala
```

<210> SEQ ID NO 44
<211> LENGTH: 19
<212> TYPE: PRT
<213> ORGANISM: Saccharomyces cerevisiae

<400> SEQUENCE: 44

```
Met Arg Phe Pro Ser Ile Phe Thr Ala Val Leu Phe Ala Ala Ser Ser
1               5                   10                  15

Ala Leu Ala
```

<210> SEQ ID NO 45
<211> LENGTH: 51
<212> TYPE: DNA
<213> ORGANISM: Saccharomyces cerevisiae
<220> FEATURE:
<221> NAME/KEY: CDS
<222> LOCATION: (1)..(51)

<400> SEQUENCE: 45

```
atg ttt aaa tct gtt gtt tat tca att tta gcc gct tct ttg gcc aat      48
Met Phe Lys Ser Val Val Tyr Ser Ile Leu Ala Ala Ser Leu Ala Asn
1               5                   10                  15 gca                                                                  51
Ala
```

<210> SEQ ID NO 46
<211> LENGTH: 17
<212> TYPE: PRT
<213> ORGANISM: Saccharomyces cerevisiae

<400> SEQUENCE: 46

```
Met Phe Lys Ser Val Val Tyr Ser Ile Leu Ala Ala Ser Leu Ala Asn
1               5                   10                  15

Ala
```

<210> SEQ ID NO 47
<211> LENGTH: 57
<212> TYPE: DNA
<213> ORGANISM: Saccharomyces cerevisiae
<220> FEATURE:
<221> NAME/KEY: CDS
<222> LOCATION: (1)..(57)

<400> SEQUENCE: 47

```
atg ctt ttg caa gct ttc ctt ttc ctt ttg gct ggt ttt gca gcc aaa      48
Met Leu Leu Gln Ala Phe Leu Phe Leu Leu Ala Gly Phe Ala Ala Lys
1               5                   10                  15 ata tct gca                                                          57
Ile Ser Ala
```

<210> SEQ ID NO 48

```
<211> LENGTH: 19
<212> TYPE: PRT
<213> ORGANISM: Saccharomyces cerevisiae

<400> SEQUENCE: 48

Met Leu Leu Gln Ala Phe Leu Phe Leu Leu Ala Gly Phe Ala Ala Lys
1               5                   10                  15

Ile Ser Ala

<210> SEQ ID NO 49
<211> LENGTH: 29
<212> TYPE: DNA
<213> ORGANISM: Artificial sequence
<220> FEATURE:
<223> OTHER INFORMATION: synthetic DNA

<400> SEQUENCE: 49
tactattagc tgaattgcca ctgctatcg                                       29

<210> SEQ ID NO 50
<211> LENGTH: 27
<212> TYPE: DNA
<213> ORGANISM: Artificial sequence
<220> FEATURE:
<223> OTHER INFORMATION: synthetic DNA

<400> SEQUENCE: 50
tctacaaccg ctaaatgttt ttgttcg                                         27
```